US009816140B2

(12) United States Patent
Barrangou et al.

(10) Patent No.: US 9,816,140 B2
(45) Date of Patent: *Nov. 14, 2017

(54) TAGGED MICROORGANISMS AND METHODS OF TAGGING

(75) Inventors: Rodolphe Barrangou, Madison, WI (US); Christophe Fremaux, Poitiers (FR); Philippe Horvath, Saint-Gervais-les-3-Clochers (FR); Dennis Romero, Oregon, WI (US)

(73) Assignee: DUPONT NUTRITION BIOSCIENCES APS (DK)

(*) Notice: Subject to any disclaimer, the term of this patent is extended or adjusted under 35 U.S.C. 154(b) by 923 days.

This patent is subject to a terminal disclaimer.

(21) Appl. No.: 12/225,852

(22) PCT Filed: May 18, 2007

(86) PCT No.: PCT/US2007/012039
§ 371 (c)(1),
(2), (4) Date: Nov. 23, 2009

(87) PCT Pub. No.: WO2007/136815
PCT Pub. Date: Nov. 29, 2007

(65) Prior Publication Data
US 2010/0104690 A1     Apr. 29, 2010

Related U.S. Application Data

(60) Provisional application No. 60/747,682, filed on May 19, 2006, provisional application No. 60/904,721, filed on Mar. 2, 2007.

(51) Int. Cl.
*C12Q 1/68* (2006.01)
*C12Q 1/70* (2006.01)

(52) U.S. Cl.
CPC .............. *C12Q 1/689* (2013.01); *C12Q 1/70* (2013.01)

(58) Field of Classification Search
None
See application file for complete search history.

(56) References Cited

U.S. PATENT DOCUMENTS

| | | | |
|---|---|---|---|
| 2,225,783 A | 12/1940 | Jensen et al. | |
| 3,024,116 A | 3/1962 | Engelland | |
| 3,403,032 A | 9/1968 | Etchells et al. | |
| 3,897,307 A | 7/1975 | Porubcan et al. | |
| 3,932,674 A | 1/1976 | Etchells | |
| 4,140,800 A | 2/1979 | Kline | |
| 4,205,132 A * | 5/1980 | Sandine et al. | 435/260 |
| 4,423,079 A | 12/1983 | Kline | |
| 5,538,864 A * | 7/1996 | Hill et al. | 435/69.1 |
| 5,888,725 A | 3/1999 | Sanders | |
| 5,895,648 A * | 4/1999 | Cavaliere Vesely et al. | 424/93.4 |
| 2010/0034924 A1 | 2/2010 | Fremaux | |
| 2010/0093617 A1 | 4/2010 | Barrangou et al. | |

FOREIGN PATENT DOCUMENTS

| | | |
|---|---|---|
| WO | WO 93/19603 A1 | 10/1993 |
| WO | 03/008631 | 1/2003 |
| WO | WO 2006/073445 A2 | 7/2006 |
| WO | WO 2007/025097 A2 | 3/2007 |
| WO | WO 2012/054726 | 10/2011 |

OTHER PUBLICATIONS

Priority Document U.S. Appl. No. 60/711,396 (Received at the International Bureau on Nov. 7, 2006).
Deveau et al., "Phage Response to CRISPR-Encoded Resistance in *Streptococcus thermophilus*," *Journal of Bacteriology*, vol. 190, No. 4, p. 1390-1400 (2008).
Barrangou, R. et al. "CRISPR Provides Acquired Resistance Against Viruses in Prokaryotes." *Science* 315(5819): 1709-1712, Mar. 23, 2007.
Bolotin, A. et al. "Clustered regularly interspaced short palindrome repeats (CRISPRs) have spacers of extrachromosomal origin." *Microbiology* 151(8): 2551-2561, Aug. 1, 2005.
Bolotin, A. et al. "Complete sequence and comparative genome analysis of the dairy bacterium *Streptococcus thermophilus*." *Nat. Biotechnol* 22(12): 1554-8, Dec. 2004.
Courtin, P. et al. "Interactions between microorganisms in a simple ecosystem: yogurt bacteria as a study model." *Le Lait* 84: 125-134, 2004.
van Embden, J.D.A. et al. "Genetic Variation and Evolutionary Origin of the Direct Repeat Locus of Mycobacterium tuberculosis Complex Bacteria." *J. Bacteriol.* 182(9): 2393-2401, May 1, 2000.
Groenen, P.M.A. et al. "Nature of DNA polymorphism in the direct repeat cluster of Mycobacterium tuberculosis; application for strain differentiation by a novel typing method." *Mol. Microbiol* 10(5): 1057-1065, 1993.
Haft, D.H. et al. "A Guild of 45 CRISPR-Associated (Cas) Protein Families and Multiple CRISPR/Cas Subtypes Exist in Prokaryotic Genomes." *PLoS Comput Biol* 1(6): e60, Nov. 11, 2005.
Hoe, N. et al. "Rapid molecular genetic subtyping of serotype M1 group A *Streptococcus* strains." *Emerging Infect. Dis* 5(2): 254-63, 1999.
Ishino, Y. et al. "Nucleotide sequence of the iap gene, responsible for alkaline phosphatase isozyme conversion in *Escherichia coli*, and identification of the gene product." *J. Bacteriol* 169(12): 5429-33, Dec. 1987.
Jansen, R. et al. "Identification of a Novel Family of Sequence Repeats among Prokaryotes." *OMICS: A Journal of Integrative Biology* 6(1): 23-33, 2002.

(Continued)

*Primary Examiner* — Oluwatosin Ogunbiyi

(57) ABSTRACT

The present invention provides methods for tagging and/or identifying microorganisms. In some preferred embodiments, the microorganisms are bacteria. In some particularly preferred embodiments, the bacteria are members of the genus *Streptococcus*, while in other embodiments, the bacteria are members of other genera. The present invention also provides microorganisms tagged using the methods set forth herein. In some preferred embodiments, the tagged microorganisms are bacteria. In some particularly preferred embodiments, the tagged bacteria are members of the genus *Streptococcus*, while in other embodiments, the tagged bacteria are members of other genera.

19 Claims, 3 Drawing Sheets

(56) References Cited

OTHER PUBLICATIONS

Jansen, R. et al. "Identification of genes that are associated with DNA repeats in prokaryotes." *Molecular Microbiology* 43(6): 1565-1575, 2002.
Lick, S. et al. "Optimized DNA extraction method for starter cultures from yoghurt." *Milchwissenschaft* 51(4): 183-186, 1996.
Masepohl, B. et al. "Long tandemly repeated repetitive (LTRR) sequences in the filamentous cyanobacterium *Anabaena* sp. PCC 7120." *Biochimica et Biophysica Acta (BBA)—Gene Structure and Expression* 1307(1): 26-30, Jun. 3, 1996.
Mojica, F.J.M. et al. "Biological significance of a family of regularly spaced repeats in the genomes of Archaea, Bacteria and mitochondria." *Molecular Microbiology* 36(1): 244-246, 2000.
Mojica, F.J.M. et al. "Intervening Sequences of Regularly Spaced Prokaryotic Repeats Derive from Foreign Genetic Elements." *Journal of Molecular Evolution* 60(2): 174-182, Feb. 17, 2005.
Mojica, F.J.M. et al. "Long stretches of short tandem repeats are present in the largest replicons of the Archaea Haloferax mediterranei and Haloferax volcanii and could be involved in replicon partitioning." *Molecular Microbiology* 17(1): 85-93, 1995.
Nakata, A. et al. "Unusual nucleotide arrangement with repeated sequences in the *Escherichia coli* K-12 chromosome." *J. Bacteriol* 171(6): 3553-6, Jun. 1989.
Pederson, C.S. "Fermented Sausage." In *Microbiology of Food Fermentations*, pp. 210-234. Westport, CT: AVI Publishing, 1979.
Pourcel, C. et al. "CRISPR elements in Yersinia pestis acquire new repeats by preferential uptake of bacteriophage DNA, and provide additional tools for evolutionary studies." *Microbiology* 151(3): 653-663, Mar. 1, 2005.
Rajagopal, S.N. et al. "Associative Growth and Proteolysis of *Streptococcus thermophilus* and Lactobacillus bulgaricus in Skim Milk." *J. Dairy Sci.* 73(4): 894-899, Apr. 1, 1990.
Suarez, A. et al. "Green fluorescent protein-based reporter systems for genetic analysis of bacteria including monocopy applications." *Gene* 196(1-2): 69-74, Sep. 1, 1997.
Viscardi, M. et al. "Selection of bacteriophage-resistant mutants of *Streptococcus thermophilus*." *Journal of Microbiological Methods* 55(1): 109-119, Oct. 2003.
Walsh, P.M. et al. "Bacterial Starter Cultures." In *Food Biotechnology*, edited by D. Knorr, pp. 538-539. New York: Marcel Dekker, 1987.
Wilmotte, A. et al. "Structure of the 16 S ribosomal RNA of the thermophilic cyanobacterium Chlorogloeopsis HTF ('Mastigocladus laminosus HTF') strain PCC7518, and phylogenetic analysis." *FEBS Letters* 317(1-2): 96-100, Feb. 8, 1993.
Database EMBL. "*Streptococcus thermophilus* strain DGCC7689 CRISPR1 locus genomic sequence." EBI accession No. EMBL:EF434458, Apr. 2, 2007.
Database EMBL. "*Streptococcus thermophilus* strain DGC7710 CRISPR1 locus genomic sequence." EBI accession No. EMBL:EF434469, Apr. 2, 2007.
CV or Christophe Fremaux Jan. 6, 2014; Group Manager in Research and Development Principal Senior Scientist.
http://oxforddictionaries.com/definition/english/encompass?q=encompass Accessed Aug. 12, 2013.
Deveau H et al., Annu. Rev. Microbiol., "CRISPR/Cas System and Its Role in Phage-Bacteria Interactions" 2010, 64 475-493.
Jansen et al., OMICS, "Identification of a Novel Family of Sequence RepRepeats long Prokaryotes" 2002, vol. No. 1, p. 23-35.
List of Bacteria genera—Wikipedia, accessed on Oct. 29, 2013.
List of Archea genera—Wikipedia, accessed on Oct. 29, 2013.
PCT/US2011/057102 (application published as WO2012/054726).
Assignment of U.S. Appl. No. 60/711,396 (one of the priority documents for WO2007025092).
CV of Dr Thomas Janzen.
CV of Eric Johansen PhD.
Applied and Environment Microbiology (2005) Instructions authors vol. 7, No. 1 pp. 1-19.
http://oxforddictionaries.com/definitions.com/definitiona/english/encomapss Accessed Jan. 30. 2014.
Excerpt from EP register (EP1916903B1) with handwritten additions Decision of the Opposition Division Oct. 31, 2012.
EPO Decision of Opposition Oct. 31, 2012 Application No. 06 802 307.6-1222/1 916 903/.
Lévesque C et al., Genomic Organization and Molecular Analysis of Virulent Bacteriophage 2972 Infecting an Exopolysaccharide-Producing *Streptococcus thermophilus* Strain, Applied and Environmental Microbiology, Jul. 2005, vol. 71, No. 7, p. 4057-4068.
Instructions to authors: applied and Environmental Microbiology.
U.S. Appl. No. 60/747,683, filed May 19, 2006, Horvath et al.
Bickle et al., "Biology of DNA Restriction," *Microbiological Reviews*, 1993, vol. 57, p. 434-450.
Mills S, et al., "CRISPR analysis of bacteriophage-insensitive mutants (BIIMs) of industrial *Streptococcus thermophilus*-implications for starter design," *Journal of Applied Microbiology*, 2010, vol. 108, p. 945-955.
Makarova K S et al., "A putative RNA-interference-based immune system in prokaryotes: computational analysis of the predicted enzymatic machinery, functional analogies with eukaryotice RNAi, and hypothetical mechanisms of action," *Biol. Direct*, 2006, vol. 1, p. 7 (DOI:10.1186/1745-6150-1-7).
Brudey K et al., "Mycobacterium tuberculosis complex genetic diversity: mining the fourth international spoligotyping database (SpolDB4) for classification, poputation genetics and epidemiology," *BMC Microbiology*, Mar. 6, 2006, doi: 10.1168/1471-2180-6-23.
Sturino et al., "Bacteriophage Defense Systems and Strategies of Lactic Acid Bacteria," *Adv. In Apply Microbial.*, 2004, vol. 56, p. 331-378.
Supporting Online Material for *Barrangou R et al., "CRISPR provides acquired resistance against viruses in prokaryotes", *Science*, 2007, vol. 315, No. 5819, p. 1702-1712.
Lucchini S et al., "Broad-Range Bacteriophage Resistance in *Streptococcus thermphilus* by Insertional Mutagenesis," *Virology*, 2000, vol. 275, p. 267-277.
Altschul S F et al., "Issues in searching molecular sequence databases," *Nature Genetics*, 1994, vol. 6, p. 119-129.
Moineau S, "Applications of phage resistance in lactic acid bacteria," *Antonie van Leuwenhoek*, 1999, vol. 76, p. 377-382.
Brouns SJJ et al., Small CRISPR RNAs Guide Antiviral Defense in Prokaryotes, Science, 2008, vol. 321, p. 960-964.
Deltcheva E et al., CRISPR RNA maturation by trans-encoded small RNA and host factor Rnase III, Nature, 2001 vol. 471, p. 602-606.
Garneau JE et al., The CRISPR/Cas bacterial immune system cleaves bacteriophage and plasmid DNA, Nature, Nov. 4, 2010, vol. 468, p. 67-71.
Gasiunas G et al., Cas9-crRNA ribonucleoprotein complex mediates specific DNA cleavage for adaptive immunity in bacteria, Proc. Natl. Acad. Sci. USA, Sep. 25, 2012;109(39):E2579-86.
Hale CR et al., RNA-Guided RNA Cleavage by CRISPR RNA-Cas Protein Complex, Cell. Nov. 25, 2009;139(5):945-956.
Horvath P et al., Comparative analysis of CRISPR loci in lactic acid bacteria genomes, International Journal of Food Microbiology, 2009, vol. 131, p. 62-70.
Horvath P et al., CRISPR/Cas, the Immune System of Bacteria and Archaea, Science, Jan. 8, 2010, vol. 327, 167-170.
Ibrahim M et al., A genome-wide survey of short coding sequences in *streptococci*, Microbiology, 2007, vol. 153, p. 3631-3644.
Jinek M et al., A programmable dual-RNA-guided DNA endonuclease in adaptive bacterial immunity, Science, Aug. 17, 2012;337(6096):816-21.
Labrie SJ et al., Bacteriophage resistance mechanisms, Nature Reviews Microbiology, May 2010;8(5):317-27 and published online Mar. 29, 2010.
Makarova K. S. et al., Evolution and classification of the CRISPR-Cas systems, Nature Reviews 2011 v9 p. 467-477.

(56) References Cited

OTHER PUBLICATIONS

Marraffini LA et al., CRISTPR Interference Limits Horizontal Gene Transfer in *Staphylococci* by Targeting DNA, Science, vol. 322, Dec. 19, 2008, p. 1843-1845.

Pougach K et al., Transcription, processing and function of CRISPR cassettes in *Esherichia coli*, Molecular Microbiology, Sep. 2010;77(6):1367-79.

Pul U et al., Identification and characterization of *E.coli* CRISPR-cas Promoters and their Silencing by H-NS, Molecular Microbiology, Mar. 2010;75(6):1495-1512.

Russell, W.M., and T. R. Klaenhammer, Efficient System for Directed integration into the Lactobacillus acidophilus and Lactobacillus gasseri Chromosomes via Homolgous Recombination, Applied and Environmental Microbiology 2001, vol. 67, No. 9, p. 4361-4364.

Sapranauskas R et al., The *Streptococcus thermophilus* CRISPR/Cas system provides immunity in *Escherichia coli*, Nucleic Acids Research, 2011, vol. 39, No. 21, p. 9275-9282.

Sashital D G et al., Mechanism of Foreign DNA Selection in a Bacterial Adaptive Immune System, Molecular Cell, 2012, vol. 46, p. 606-615.

Sinkunas T et al., Cas3 is a single-stranded DNA nuclease and ATP-dependent helicase in CRISPR/Cas immune system, EMBO Journal 2011, vol. 30, p. 1335-1342.

Westra ER et al., CRISPR Immunity Relies on the Consecutive Binding and Degradation of Negatively Supercoiled Invader DNA by Cascade and Cas3, Molecular Cell, 2012, vol. 46, p. 595-605.

Westra ER et al., H-NS-mediated repression of CRISPR-based immunity in *Escherichia coli* K12 can be relieved by the transcription activator LeuO, Molecular Microbiology, 2010, vol. 77, No. 6, p. 1380-1381.

NCBI GenBank EF529515 *Streptococcus* phage 858, downloaded Feb. 11, 2014.

Carvalho, et al., "Relevant factors for the preparation of freeze-dried lactic acid bacteria," International Dairy Journal (2004) vol. 14. No. 10 pp. 835-847.

* cited by examiner

FIGURE 5

TAGGED MICROORGANISMS AND METHODS OF TAGGING

The present application claims priority to U.S. Prov. Pat. Appln. Ser. No. 60/747,682, filed May 19, 2006, and U.S. Prov. Pat. Appln. Ser. No. 60/904,721, filed Mar. 2, 2007.

FIELD OF THE INVENTION

The present invention provides methods for tagging and/or identifying microorganisms. In some preferred embodiments, the microorganisms are bacteria. In some particularly preferred embodiments, the bacteria are members of the genus *Streptococcus*, while in other embodiments, the bacteria are members of other genera. The present invention also provides microorganisms tagged using the methods set forth herein. In some preferred embodiments, the tagged microorganisms are bacteria. In some particularly preferred embodiments, the tagged bacteria are members of the genus *Streptococcus*, while in other embodiments, the tagged bacteria are members of other genera.

BACKGROUND OF THE INVENTION

Microbial strains, especially those used as starter cultures for the fermented food/beverage industry are highly selected and characterized for specific functionalities. Typically, these starter cultures are commercially sold as live organisms and often remain viable in the end product. Thus, it is possible to isolate, identify and characterize the starter culture strains by culturing the microorganisms present in the end products. In addition, it is then possible to utilize these starter culture strains in other products, including competitive products. It is difficult to monitor the use of such strains by others, including competitors. Indeed, there is a need in the art for methods to easily tag cultures in order to identity their source(s) and monitor their use in various products.

SUMMARY OF THE INVENTION

The present invention provides methods for tagging and/or identifying microorganisms. In some preferred embodiments, the microorganisms are bacteria. In some particularly preferred embodiments, the bacteria are members of the genus *Streptococcus*, while in other embodiments, the bacteria are members of other genera. The present invention also provides microorganisms tagged using the methods set forth herein. In some preferred embodiments, the tagged microorganisms are bacteria. In some particularly preferred embodiments, the tagged bacteria are members of the genus *Streptococcus*, while in other embodiments, the tagged bacteria are members of other genera.

In some embodiments, the present invention provides methods for labelling or tagging a bacterium comprising the steps of: (a) exposing a parent bacterium to a bacteriophage; (b) selecting a bacteriophage insensitive mutant; (c) comparing a CRISPR locus or a portion thereof from the parent bacterium and the bacteriophage insensitive mutant; and (d) selecting a tagged bacterium comprising an additional repeat-spacer unit in the CRISPR locus that is not present in the parent bacterium. In some preferred embodiments, the tagged bacterium is obtained or obtainable by the method according to the present invention. In further embodiments, the present invention provides cell cultures comprising the tagged bacterium.

The present invention also provides food product and/or feed products comprising the tagged bacterium and/or cell cultures comprising at least one tagged bacterial species. In yet additional embodiments, the present invention provides processes for preparing food and/or feed products comprising the tagged bacteria and/or cell cultures comprising at least one tagged bacterial species. In some embodiments, the present invention provides methods for preparing food and/or feed comprising the step of adding the tagged bacterium or the cell culture to said food product or feed. In yet additional embodiments, the present invention provides food and/or feed obtained or obtainable using the methods of the present invention.

In additional embodiments, the present invention provides methods for generating CRISPR variants, comprising the steps of: (a) exposing a parent bacterium to a bacteriophage; (b) selecting a bacteriophage resistant bacterium; (c) comparing the CRISPR locus or a portion thereof from the parent bacterium and the bacteriophage insensitive mutant; (d) selecting a tagged bacterium comprising an additional repeat-spacer unit in the CRISPR locus that is not present in the parent bacterium; and (e) isolating and/or cloning and/or sequencing the additional repeat-spacer unit. The present invention also provides CRISPR variants obtained or obtainable using the methods of the present invention.

In some additional embodiments, the present invention also provides compositions and methods for the use of at least one nucleotide sequence obtained or obtainable from a bacteriophage for tagging and/or identifying a bacterium, wherein the phage nucleotide sequence is integrated within the CRISPR locus of the parent bacterium. In some alternative embodiments, the present invention provides methods and compositions for using a nucleotide sequence for labelling and/or identifying a bacterium, wherein the nucleotide sequence is obtained or obtainable by: (a) exposing a parent bacterium to a bacteriophage; (b) selecting a bacteriophage insensitive mutant; (c) comparing a CRISPR locus or a portion thereof from the parent bacterium and the bacteriophage insensitive mutant; and (d) selecting a tagged bacterium comprising an additional repeat-spacer unit in the CRISPR locus that is not present in the parent bacterium. In additional embodiments, the present invention also provides methods for identifying tagged bacteria, comprising the step of screening the bacteria for an additional repeat-spacer unit within a CRISPR locus of the bacterium.

In some further embodiments, the present invention provides methods for identifying a tagged bacterium comprising the steps of: (a) screening the bacterium for an additional repeat-spacer unit in a CRISPR locus; (b) determining the nucleotide sequence of the additional repeat-spacer unit; (c) comparing the nucleotide sequence of the additional repeat-spacer unit with a database of tagged bacteria obtained or obtainable by the method of the present invention; and (d) identifying a nucleotide sequence in the database of tagged bacteria that matches the additional repeat-spacer unit.

In some embodiments, the 5' end and/or the 3' end of the CRISPR locus of the parent bacterium is/are compared. In some particularly preferred embodiments, at least the first CRISPR repeat and/or the first CRISPR spacer (e.g., the first CRISPR spacer core) at the 5' end of the CRISPR locus is/are compared. In still further embodiments, at least the last CRISPR repeat and/or the last CRISPR spacer (e.g., the last CRISPR spacer core) at the 3' end of the CRISPR locus is/are compared. In additional preferred embodiments of the methods of the present invention, the methods comprise the step of selecting a tagged bacterium comprising an additional repeat-spacer unit at the 5' end and/or at the 3' end of the CRISPR locus that is not present in the parent bacterium. In some embodiments, the methods of the present invention comprise exposing the parent bacterium to two or more bacteriophage either simultaneously or sequentially.

In some further embodiments, the CRISPR locus or at least a portion thereof from the parent bacterium and the bacteriophage insensitive mutant are compared by amplifying the CRISPR locus or a portion thereof from the parent bacterium and/or the bacteriophage insensitive mutant. In some preferred embodiments, amplification is accomplished using PCR. In some additional embodiments, the CRISPR locus or at least a portion thereof from the parent bacterium and the bacteriophage insensitive mutant are compared by sequencing the CRISPR locus or a portion thereof from the parent bacterium and/or the bacteriophage insensitive mutant. In some particularly preferred embodiments, the CRISPR locus or at least a portion thereof from the parent bacterium and the bacteriophage insensitive mutant are compared by amplifying and then sequencing the CRISPR locus or a portion thereof from the parent bacterium and/or the bacteriophage insensitive mutant. In some embodiments, the additional repeat-spacer unit is at least 44 nucleotides in length. In some further embodiments, a tagged bacterium comprising two or three or more additional repeat-spacer units is selected. In some preferred embodiments, the additional repeat-spacer unit comprises at least one nucleotide sequence that has at least about 95% identity, or more preferably, about 100% identity to a CRISPR repeat in the CRISPR locus of the parent bacterium. In some alternative preferred embodiments, the additional repeat-spacer unit comprises at least one nucleotide sequence that has at least 95% identity, preferably, 100% identity to a nucleotide sequence in the genome of the bacteriophage used for the selection of the tagged bacterium.

In some alternative preferred embodiments, the additional repeat-spacer unit comprises a first nucleotide sequence that has at least about 95% identity, or more preferably, about 100% identity to a CRISPR repeat in the CRISPR locus of the parent bacterium and a second nucleotide sequence that has at least one nucleotide sequence that has at least about 95% identity, or more preferably, about 100% identity to a nucleotide sequence in the genome of the bacteriophage used for the selection of the tagged bacterium.

In some alternative preferred embodiments, the methods provided by the present invention for identifying a tagged bacterium comprise the additional step of comparing the additional repeat-spacer unit with a bacteriophage sequence database and/or a bacterial sequence database.

In some preferred embodiments, the parent bacterium is suitable for use as a starter culture, a probiotic culture and/or a dietary supplement. In some preferred embodiments, the parent bacterium is selected from the group of genera consisting of: *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Bifidobacterium, Brevibacterium, Propionibacterium, Laciococcus, Lactobacillus, Pediococcus, Leuconostoc* and *Oenococcus*. In some embodiments, the present invention finds use with cell cultures, including but not limited to starter cultures, probiotic cultures and/or dietary supplements.

In some further preferred embodiments, the bacteriophage is selected from the group of virus families consisting of: Corticoviridae, Cystoviridae, Inoviridae, Leviviridae, Microviridae, Myoviridae, Podoviridae, Siphoviridae, and Tectiviridae.

In some embodiments, the present invention provides *S. thermophilus* comprising a sequence obtained or obtainable from a bacteriophage, wherein said sequence comprises SEQ ID NO:3 and/or 4. In some embodiments, the present invention provides *S. thermophilus* comprising a sequence obtained or obtainable from a bacteriophage, wherein the sequence comprises SEQ ID NO:3 and/or 4 located downstream (e.g., directly downstream) of the first CRISPR repeat in at least one CRISPR locus. In yet further embodiments, the present invention provides *S. thermophilus* comprising a sequence obtained or obtainable from a bacteriophage, wherein the sequence comprises SEQ ID NO:9. In some preferred embodiments, the *S. thermophilus* comprises a sequence obtained or obtainable from a bacteriophage, wherein the sequence comprises SEQ ID NO:9 downstream (e.g., directly downstream) of the first CRISPR repeat in at least one CRISPR locus. In yet further embodiments, the present invention provides *S. thermophilus* comprising a sequence obtained or obtainable from a bacteriophage, wherein the sequence comprises SEQ ID NO:11. In still further embodiments, the *S. thermophilus* comprises a sequence obtained or obtainable from a bacteriophage, wherein said sequence comprises SEQ ID NO:11 downstream (e.g., directly downstream) of the first CRISPR repeat in at least one CRISPR locus.

The present invention provides methods for tagging a bacterium comprising the steps of: exposing at least one parent bacterium comprising at least a portion of a CRISPR locus to at least one exogenous nucleic acid sequence to produce at least one tagged bacterium comprising a modified CRISPR locus, wherein the modified CRISPR locus comprises at least one additional repeat-spacer unit than the CRISPR locus of the parent bacterium and wherein the additional repeat-spacer unit comprises a tag; and comparing at least a portion of the CRISPR locus of the parent bacterium and the modified CRISPR locus of said tagged bacterium. In some embodiments, the exogenous nucleic acid sequence is selected from bacteriophages, plasmids, megaplasmids, transposable elements, transposons, and insertion sequences. In some particularly preferred embodiments, the exogenous nucleic acid comprises at least a portion of the genome of at least one bacteriophage. In some alternative particularly preferred embodiments, the tagged bacterium is a bacteriophage insensitive mutant. In some additional embodiments, the 5' end and/or the 3' end of the CRISPR locus of the parent bacterium is compared with the modified CRISPR locus of the tagged bacterium. In additional embodiments, the 5' and/or the 3' end of at least the first CRISPR repeat and/or at least the first CRISPR spacer of the CRISPR locus of the parent bacterium is compared with the modified CRISPR locus of the tagged bacterium. In some further embodiments, the methods further comprise the step of selecting at least one tagged bacterium. In yet additional embodiments, the parent bacterium is simultaneously or sequentially exposed to two or more bacteriophages. In some preferred embodiments, the tagged bacterium comprises at least one additional repeat-spacer unit. In some alternative embodiments, at least a portion of the CRISPR locus of the parent bacterium and at least a portion of the modified CRISPR locus of the tagged bacterium are compared by amplifying at least a portion of the CRISPR locus and at least a portion of the modified CRISPR locus, to produce an amplified CRISPR locus sequence and an amplified modified CRISPR locus sequence. In some preferred embodiments, amplifying comprises the use of the polymerase chain reaction. In some alternative preferred embodiments, at least a portion of the CRISPR locus of the parent bacterium and at least a portion of the modified CRISPR locus of said the bacterium are compared by sequencing at least a portion of the CRISPR locus and at least a portion of the modified CRISPR locus. In some additional embodiments, the methods further comprise the step of sequencing the amplified CRISPR locus sequence and the amplified modified CRISPR sequence locus. In some preferred embodiments, the additional repeat-spacer unit comprises at least about 44 nucleotides. In some additional embodiments, the additional repeat-spacer unit comprises at least one nucleotide sequence that has at least 95% identity to a CRISPR repeat in the CRISPR locus of the parent bacterium. In some further embodiments, the additional repeat-spacer unit comprises at least one nucleotide sequence that has at least 95% identity to a nucleotide sequence in the genome of at least one bacteriophage. In yet additional embodiments, the tagged bacterium further comprises at least one additional nucleotide sequence that has at least 95% identity to a nucleotide sequence in the genome of at least one bacteriophage. In some preferred embodiments, the parent bacterium is an industrially useful culture. In some particularly preferred embodiments, the parent bacterium comprises a culture selected from starter cultures, probiotic cultures, and dietary supplement cultures. In some further particularly preferred embodiments, the parent bacterium is selected from *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Bifidobacterium, Brevibacterium, Propionibacterium, Lactococcus, Lactobacillus, Pediococcus, Leuconostoc* and *Oenococcus*. In some further embodiments, the at least one bacteriophage is selected from the group of virus families consisting of: Corticoviridae, Cystoviridae, Inoviridae, Leviviridae, Microviridae, Myoviridae, Podoviridae, Siphoviridae, and Tectiviridae.

The present invention also provides tagged bacteria obtained using the methods set forth herein. In some preferred embodiments, the tagged bacterium is an industrially useful culture. In some alternative embodiments, the present invention provides cell cultures comprising the tagged bacteria produced using the methods set forth herein. In some additional embodiments, the cell culture comprising tagged bacteria comprises an industrially useful culture. In some particularly preferred embodiments, the tagged bacterium comprises a culture selected from starter cultures, probiotic cultures and dietary supplement cultures. In yet additional embodiments, the present invention provides food and/or feed comprising tagged bacterium obtained using the methods set forth herein.

The present invention also provides methods for preparing food and/or feed comprising the use of tagged bacteria, wherein tagged bacteria are added to the food or feed. In some additional embodiments, the cell culture comprising tagged bacteria comprises an industrially useful culture. In some particularly preferred embodiments, the tagged bacterium comprises a culture selected from starter cultures, probiotic cultures and dietary supplement cultures. In yet additional embodiments, the present invention provides food and/or feed comprising tagged bacterium obtained using the methods set forth herein.

The present invention also provides methods for generating at least one CRISPR variant comprising a tag, comprising the steps of: exposing a parent bacterium comprising at least a portion of a CRISPR locus to at least one bacteriophage to produce a culture of bacteriophage resistant variant bacteria comprising a modified CRISPR locus; selecting bacteriophage resistant variant bacteria; comparing the CRISPR locus or a portion thereof of the parent bacterium and the modified CRISPR locus of the bacteriophage insensitive variant, to identify bacteriophage insensitive variants comprising at least one tag, wherein at least one tag comprises at least one additional nucleic acid fragment in the modified CRISPR locus that is absent from the CRISPR locus of the parent bacterium; selecting the bacteriophage insensitive variants comprising a tag; and analyzing at least one tag. In some preferred embodiments, the analysis is accomplished using any suitable method known in the art. In some particularly preferred embodiments, the analysis is selected from isolating, cloning and sequencing. The present invention also provides at least one CRISPR variant obtained using the methods set forth herein. In some additional embodiments, the present invention provides cell cultures comprising at least one CRISPR variant produced using the methods provided herein. In yet additional embodiments, the present invention provides food and/or feed comprising at least one CRISPR variant produced using the methods set forth herein. In some additional embodiments, at least one tag is integrated into the CRISPR locus of the parent bacterium to produce at least one CRISPR variant.

The present invention also provides methods for identifying a tagged bacterium comprising at least one CRISPR locus, comprising the steps of: screening a tagged bacterium the presence of a tag in the CRISPR locus; determining the nucleotide sequence of the tag; comparing the nucleotide sequence of the tag with nucleotide sequences present in at least one database; and identifying a nucleotide sequence in the database that shares homology with the tag. In some embodiments, the database comprises nucleotide sequences of tagged bacteria. In some further embodiments, the database is selected from bacteriophage sequence databases and bacterial sequence databases.

DESCRIPTION OF THE FIGURES

FIG. 5 provides a sequence comparison of part of the sequence of the CRISPR1 locus of the isolate obtained from the fermented milk product with the sequence of the CRISPR1 locus of DGCC7710 (SEQ ID NO:1), with the CRISPR1 consensus repeat sequence (SEQ ID NO:74) and with the sequence of the additional spacer sequence in $DGCC_{phi2972}^{S41}$ (SEQ ID NO:75). The leader sequence of CRISPR1 is shown in lowercase, the repeat sequences are boxed, and the other sequences correspond to spacer sequences.

DESCRIPTION OF THE INVENTION

Figure 1:
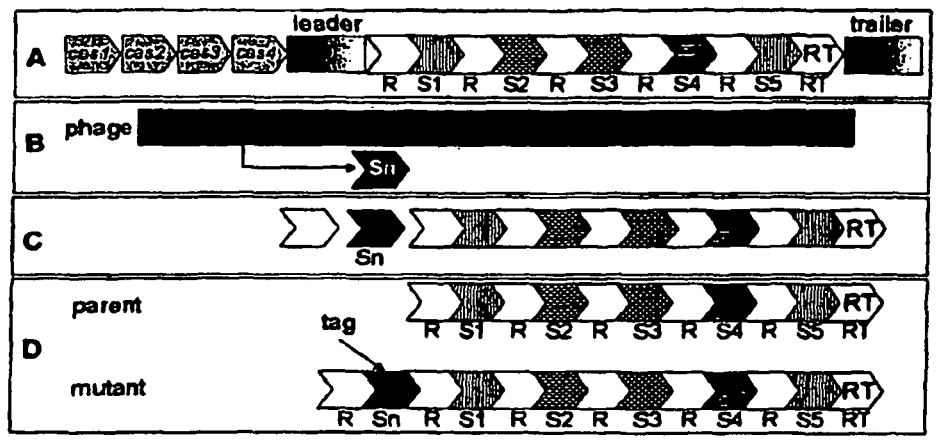
FIG. 1 illustrates one embodiment of the present invention in which a tagging sequence and a CRISPR repeat are integrated at one end of the CRISPR locus. Panel A shows a CRISPR locus and element including repeats (R), spacers (S), the upstream leader and downstream trailer, with the terminal repeat (RD adjacent to the trailer, and cas genes in the vicinity (4 cas genes named cas1 to cas4 in this example, not drawn to scale). cas genes can be on either end, or split and present on both ends. Cas genes may be located on any of the two DNA strands. Panel B shows a phage sequence in black, with a fragment of the sequence (Sn) being used as an additional spacer (i.e., tagging sequence). Panel C shows the insertion of a new spacer (Sn) (i.e., tagging sequence) at one end of the CRISPR locus (close to the leader in this example at the 5' end of the CRISPR locus), between two repeats. Panel D provides a comparison of the CRISPR locus content between the parent and the mutant bacterium (i.e., tagged bacterium), with a new spacer (Sn) (i.e., tagging sequence) integrated at one end of the CRISPR locus (close to the leader in this example), between repeats. The new spacer (Sn) constitutes the tagging sequence which is specific for the mutant bacterium (i.e., tagged bacterium). In some embodiments, this process results in the addition of one or more spacers from the phage sequence.
Figure 2:
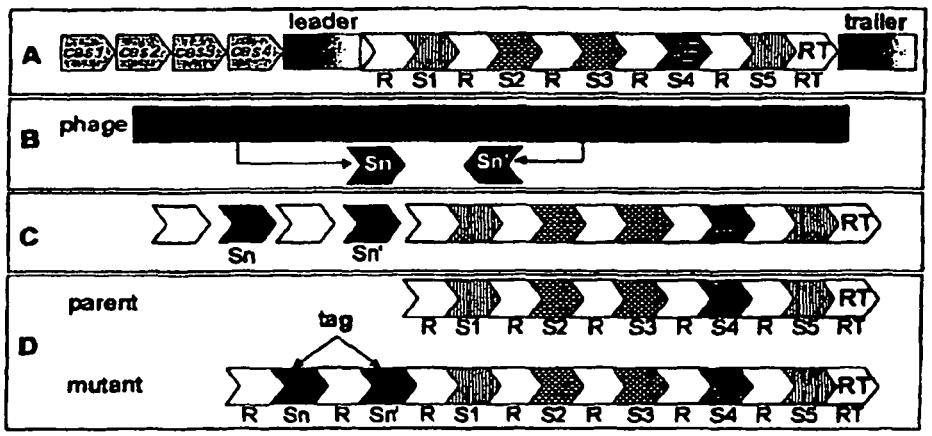
FIG. 2 illustrates one embodiment of the present invention in which two tagging sequences and two CRISPR repeats are integrated at one end of the CRISPR locus. Panel A shows a CRISPR locus and elements, including repeats (R), spacers (S), the upstream leader and downstream trailer, with the terminal repeat (RT) adjacent to the trailer, and cas genes in the vicinity (4 cas genes named cas1 to cas4 in this example, not drawn to scale). Cas genes can be on either end, or split and present on both ends. Cas genes may be located on any of the two DNA strands. Panel B shows a phage sequence in black, with two fragments of the sequence (Sn and Sn') being used as additional spacers (i.e., tagging sequences). Panel C illustrates insertion of the new spacers (i.e., tagging sequences) (Sn and Sn') at the same end of the CRISPR locus (close to the leader in this example at the 5' end), each in-between two repeats. Panel D provides a comparison of the CRISPR locus content between the parent and the mutant bacterium (i.e., tagged bacterium), with two new spacers (Sn and Sn') integrated at the same end of the CRISPR locus (close to the leader in this example at the 5' end), each in between repeats. The new spacers Sn and Sn' constitute the tagging sequence which is specific of the mutant. In some embodiments, this process results in the addition of one or more spacers from the phage sequence.

The present invention provides methods for tagging and/or identifying microorganisms. In some preferred embodiments, the microorganisms are bacteria. In some particularly preferred embodiments, the bacteria are members of the genus *Streptococcus*, while in other embodiments, the bacteria are members of other genera. The present invention also provides microorganisms tagged using the methods set forth herein. In some preferred embodiments, the tagged microorganisms are bacteria. In some particularly preferred embodiments, the tagged bacteria are members of the genus *Streptococcus*, while in other embodiments, the tagged bacteria are members of other genera.

There is a need for methods and compositions useful in the identification of specific bacterial strains, in order to determine their origin. Although it is feasible to insert a synthetic oligonucleotide into a strain to tag or label it using recombinant DNA technologies, the tagged strain would be considered to be a genetically modified organism and would be likely to face regulatory issues in commercial applications.

In addition, the preparation of cultures is labor intensive, occupying much space and equipment, and there is a considerable risk of contamination with spoilage bacteria and/or phages during the propagation steps. The failure of bacterial cultures due to bacteriophage (phage) infection and multiplication is a major problem with the industrial use of bacterial cultures. There are many different types of phages and new strains continue to emerge. Thus, there is a need for methods and compositions for tracking and monitoring bacteria used in such cultures.

When a bacterial population is infected with a virulent bacteriophage many of the cells are killed by the bacteriophage. However, spontaneous phage-resistant mutants are often produced. These bacteriophage-resistant bacteria correspond to a subpopulation of bacteria that are able to withstand and survive bacteriophage infection. These resistant bacteria are referred to herein as "bacteriophage resistant mutants," "bacteriophage insensitive mutants," "BIMs," "tagged bacteria," "tagged bacterium," "labelled bacteria," or "labelled bacterium."

As described herein, when a bacteriophage infects a bacterium, one or more sequences originating from the bacteriophage genome are integrated into (e.g., within) the CRISPR locus of the bacterium, while in other embodiments, integration occurs in other locations within the bacterium's genome. Indeed, in some embodiments, "bacteriophage resistant mutants"/"bacteriophage insensitive mutants"/"BIMs" have bacteriophage sequence integrated in CRISPR while in other embodiments, strains have other type of chromosomal mutation. However, it is intended that tagged bacteria are produced due to integration of phage sequence integration into CRISPR. Thus, the bacteriophage-derivable or derived sequence is new to the CRISPR locus of the bacterium and provides a "label" or "tag," which is identifiable by its location and/or sequence and/or adjacent sequence. It has also been found that a duplicated sequence (e.g., a duplicated CRISPR repeat) originating from the parent bacterium is also integrated iteratively, sequentially, simultaneously or substantially simultaneously along with the sequence originating from the bacteriophage genome.

In addition, in some embodiments, independent infection of a culture (e.g., a pure culture) of a given bacterial strain using the same virulent bacteriophage leads to the integration of one or more different bacteriophage sequences into the CRISPR locus of the bacterial strain. In some preferred embodiments, the integration of different bacteriophage sequences in the CRISPR locus of the bacterial strain is a random event. However, in some other embodiments, the integration is not a random occurrence. Once it is integrated it is maintained and thus becomes a robust means to tag and/or track a bacterium. Thus, the one or more sequences originating from the bacteriophage genome are not only new to the CRISPR locus of the parent bacterium but are also a tag that is unique to each bacterium. Thus, the present invention provides compositions and methods for tagging (i.e., labelling) and/or identifying a bacterium. Furthermore, the methods and compositions of the present invention are particularly advantageous because the method is a 'natural' method that does not result in a genetically modified organism. Accordingly, labelled or tagged bacteria prepared according to the methods of the present invention are not considered to be genetically modified, since the bacteria have been created by a natural biological process of bacteriophage infection.

The present invention provides methods for the use of a sequence obtained or obtainable from a bacteriophage (e.g., in the manufacture of a tagged bacterium) for tagging and/or identifying a bacterium, wherein the sequence is integrated at one end of the CRISPR locus of a parent bacterium. In some preferred embodiments, the present invention provides methods for the use of a sequence obtained or obtainable from a bacteriophage (e.g., in the manufacture of a tagged bacterium) for tagging and/or identifying a bacterium, wherein the sequence comprises: (i) at least one sequence that is homologous (e.g., identical) to a CRISPR repeat in the CRISPR locus of the bacterium; and (ii) a tagging sequence. In further embodiments, the present invention provides methods for the use of a sequence for tagging and/or identifying a bacterium (e.g., in the manufacture of a tagged bacterium), wherein the sequence is obtained or obtainable by: (a) exposing a parent bacterium to a bacteriophage; (b) selecting a bacteriophage insensitive mutant; (c) comparing the CRISPR locus or a portion thereof from the parent bacterium and the bacteriophage insensitive mutant; and (d) selecting a sequence in the CRISPR locus or a portion thereof of the bacteriophage insensitive mutant that is not present in the parent bacterium.

In some additional embodiments, the present invention provides nucleic acid sequences (e.g., recombinant or an isolated nucleic acid sequence) consisting essentially of at least one gene or protein. In some embodiments, the nucleic acid sequence is DNA, while in other embodiments, it is RNA. Nucleic acid from any suitable origin finds use in the present invention, including genomic, synthetic or recombinant nucleic acid (e.g., cDNA). However, in some particularly preferred embodiments, the sequence is a naturally-occurring nucleic acid sequence. In some embodiments, the nucleotide sequence is double-stranded, while in other embodiments, it is single-stranded. In some further embodiments, the nucleic acid sequence represents the sense strand, while in other embodiments it represents the antisense strand or combinations thereof. Recombinant nucleic acid sequences prepared using any suitable recombinant technique known the art find use in the present invention. In some preferred embodiments the target nucleic acid sequence is or is derived from a gene. In some particularly preferred embodiments, the nucleic acid sequence is an "exogenous nucleic acid sequence" which is introduced into a parent bacterium using any suitable method known in the art, including but not limited to natural and recombinant methods. In some most particularly preferred embodiments, the exogenous nucleic acid sequence comprises at least a portion of a bacteriophage genome. In some additional particularly preferred embodiments, the exogenous nucleic acid sequence is introduced into a parent bacterium through exposure of the bacterium to at least one bacteriophage.

In some embodiments, the nucleic acid sequence and the nucleic acids encompassed by the present invention are isolated or substantially purified. As used herein, the terms "isolated" or "substantially purified" refer to nucleic acid molecules, biologically active fragments, variants, homologues, or derivatives thereof that are substantially or essentially free from components normally found in association with the nucleic acid in its natural state. Such components include other cellular material, culture media from recombinant production, and various chemicals used in chemically synthesising the nucleic acids. In some embodiments, an "isolated" nucleic acid sequence or nucleic acid is typically free of nucleic acid sequences that flank the nucleic acid of interest in the genomic DNA of the organism from which the nucleic acid was derived (e.g., coding sequences present at the 5' or 3' ends). However, in some embodiments, the molecule includes some additional bases or moieties that do not deleteriously affect the basic characteristics of the composition.

The nucleic acid sequence(s) find use engineering cells (e.g., a recipient cell). In some embodiments, the nucleic acid sequence is inserted into the DNA (e.g., plasmid DNA or genomic DNA) of a recipient cell using any suitable method known in the art (e.g., homologous recombination). In other embodiments, nucleic acid sequence(s) find use as templates upon which to modify (e.g., mutate) the DNA of a cell (e.g., a recipient cell) such as plasmid DNA or genomic DNA, under conditions such that the nucleic acid sequence(s) are created in the DNA of the cell. In some preferred embodiments, the nucleic acid sequence(s) are cloned (e.g., into a construct, plasmid or a vector) which is then used to transform the cell using any suitable method known in the art.

The present invention provides methods and compositions utilizing variants, homologues, derivatives and fragments thereof. The term "variant" is used herein in reference to a naturally occurring polypeptide or nucleotide sequences which differs from a wild-type sequence. As used herein, the term "fragment," refers to a polypeptide or nucleotide sequence that comprises a fraction of a wild-type sequence. In some embodiments, fragments comprise one or more large contiguous sections of sequence or a plurality of small sections. In some embodiments, the sequence also comprises other elements. For example, in some embodiments, it is a fusion protein that includes another protein sequence. In some preferred embodiments, the sequence comprises at least about 50%, more preferably at least about 65%, more preferably at least about 80%, more preferably at least about 85%, more preferably at least 90%, more preferably at least 95%, more preferably at least 96%, more preferably at least about 97%, more preferably at least about 98%, or most preferably at least about 99% of the wild-type sequence.

In some particularly preferred embodiments, the fragment is a functional fragment. As used herein, a "functional fragment" of a molecule refers to a fragment retaining or possessing substantially the same biological activity as the intact molecule. In particularly preferred embodiments, functional fragments retain at least about 10%. In other embodiments, at least about 25%, about 50%, about 75%, about 80%, about 85%, about 90%, about 95%, about 96%, about 97%, about 98%, or about 99% of the biological activity of the intact molecule. In alternative embodiments, the fragment retains about 50%, more preferably about 60%, more preferably about 70%, more preferably about 80%, more preferably about 85%, more preferably about 90%, more preferably about 95%, more preferably about 96%, more preferably about 97%, more preferably about 98%, or most preferably about 99% activity of the wild-type polypeptide or nucleotide sequence.

As used herein, the term "homologue" refers to an entity having a certain homology with the subject amino acid sequences and the subject nucleotide sequences. As used particularly herein, the term "homology" is synonymous with "identity." In the present context, a homologous sequence is taken to include an amino acid sequence, which is at least about 75, about 85 or about 90% identical, preferably at least about 95%, about 96%, about 97%, about 98% or about 99% identical to the subject sequence. Although homology can also be considered in terms of similarity (i.e., amino acid residues having similar chemical properties/functions), in the context of the present invention it is preferred to express homology in terms of sequence identity. In some preferred embodiments, a homologous sequence comprises a nucleotide sequence, which is at least about 75, about 85 or about 90% identical, preferably at least about 95%, about 96%, about 97%, about 98%, or about 99% identical to the subject sequence (i.e., the sequence of interest used as a reference). In some embodiments, homology comparisons are conducted by eye, although other methods known in the art find use (e.g., with the aid of readily available sequence comparison programs). Commercially available computer programs are capable of calculating the percent homology (% homology) between two or more sequences, and thus find use in the present invention. Indeed methods and systems are readily commercially available for such analyses. Additional descriptions of some suitable methods, as well as methods and compositions suitable for substitutions, etc., are provided in U.S. Prov. Appln. Ser. No. 60/904,701, filed Mar. 2, 2007.

DETAILED DESCRIPTION OF THE INVENTION

The present invention provides methods for tagging and/or identifying microorganisms. In some preferred embodiments, the microorganisms are bacteria. In some particularly preferred embodiments, the bacteria are members of the genus *Streptococcus*, while in other embodiments, the bacteria are members of other genera. The present invention also provides microorganisms tagged using the methods set forth herein. In some preferred embodiments, the tagged microorganisms are bacteria. In some particularly preferred embodiments, the tagged bacteria are members of the genus *Streptococcus*, while in other embodiments, the tagged bacteria are members of other genera.

A. CRISPRs and CRISPR Loci

CRISPRs (Clustered Regularly Interspaced Short Palindromic Repeats); also known as SPIDRs—SPacer Interspersed Direct Repeats) constitute a family of recently described DNA loci that are usually specific to a particular bacterial species. The CRISPR locus is a distinct class of interspersed short sequence repeats (SSRs) that were first recognized in *E. coli* (Ishino et al., J. Bacteriol., 169:5429-5433 [1987]; and Nakata et al., J. Bacteriol. 171:3553-3556 [1989]). Similar interspersed SSRs have been identified in *Haloferax medilerranei, Streptococcus pyogenes, Anabaena*, and *Mycobacterium tuberculosis* (See, Groenen et al., Mol. Microbiol. 10:1057-1065 [1993]; Hoe et al., Emerg. Infect. Dis., 5:254-263 [1999]; Masepohl et al., Biochim. Biophys. Acta 1307:26-30 [1996]; and Mojica et al., *Mol. Microbiol.* 17:85-93 [1995]). The CRISPR loci differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol. 36:244-246 [2000]). The repeats are short elements that occur in clusters that are always regularly spaced by unique intervening sequences with a constant length (Mojica et al., [2000], supra). Although the repeat sequences are highly conserved between strains, the number of interspersed repeats and the sequences of the spacer regions differ from strain to strain (van Embden et al., J. Bacteriol., 182:2393-2401 [2000]).

CRISPR loci consist of short and highly conserved partially palindromic DNA repeats typically of 24 to 40 bp. These repeats have been reported to occur in a range from 1 to 249. Although isolated elements have been detected, they are generally arranged in clusters (up to about 20 or more per genome) of repeated units spaced by unique intervening 20-58 by sequences. To date, up to 20 distinct CRISPR loci have been found within a single chromosome. CRISPRs are generally homogenous within a given genome with most of them being identical. However, there are examples of heterogeneity in, for example, the Archaea (Mojica et al., [2000], supra).

As used herein, the term "CRISPR locus" refers to the DNA segment which includes all of the CRISPR repeats, starting with the first nucleotide of the first CRISPR repeat and ending with the last nucleotide of the last (terminal) CRISPR repeat. In some alternative embodiments, "at least a portion" of at least one CRISPR locus finds use. Thus, it is intended that the present invention encompass embodiments in which at least one entire CRISPR locus is used, as well as embodiments in which at least a portion (i.e., part of at least one CRISPR locus).

Although the biological function of CRISPR loci is unknown, some hypotheses have been proposed. For example, it has been proposed that they may be involved in the attachment of the chromosome to a cellular structure, or in the chromosome replication and replicon partitioning (Jansen et al., OMICS 6:23-33 [2002]; Jansen et al., Mol. Microbiol., 43:1565-1575 [2002]; and Pourcel et al., Microbiol., 151:653-663 [2005]). Mojica et al. (Mojica et al., J. Mol. Evol., 60:174-182 [2005]) hypothesize that CRISPR may be involved in conferring specific immunity against foreign DNA and Pourcel et al. (supra) hypothesize that CRISPRs are structures that are able to take up pieces of foreign DNA as part of a defense mechanism. Bolotin et al. (supra) suggest that the CRISPR spacer elements are the traces of past invasions by extrachromosomal elements, and hypothesize that they provide a cell with immunity against phage infection, and more generally foreign DNA expression, by coding an anti-sense RNA. Bolotin et al. (supra) also suggest that car genes are necessary for CRISPR formation. However, it is not intended that the present invention be limited to any particular mechanism, function, theory, nor means of action.

B. Identifying CRISPR Loci

Various methods for identifying CRISPR loci are known in the art. For example, Jensen et al. (Jensen et al., [2002], supra) describe a computer-based approach in which nucleotide sequences are searched for CRISPR motifs using the PATSCAN program at the server of the Mathematics and Computer Science Division at the Argonne National Laboratory, Argonne, Ill., USA. The algorithm that was used for identifying CRISPR motifs was p1=a . . . bc . . . d p1c . . . d p1c . . . dp1, where a and b were the lower and upper size limit of the repeat and p1 and c and d were the lower and upper size limit of the spacer sequences. The values of a, b, c and d may be varied from about 15 to about 70 bp at increments of about 5 bp. In some preferred embodiments, CRISPR loci are identified using dotplots (e.g., by using the Dotter computer program).

Any suitable method known in the art finds use in analyzing sequence similarity. For example, analysis may be performed using NCB1 BLAST with a microbial genomes database and GenBank, as known in the art. In addition, nucleotide sequences, including those provided herein are included in databases (e.g., GenBank or the JG1 genome website).

In additional embodiments, the methods of the present invention utilize amplification procedures (See e.g., Mojica et al., [2005], supra; and Pourcel et al., [2005], supra). Amplification of the desired region of DNA may be achieved by any method known in the art, including polymerase chain reaction (PCR). "Amplification" refers to the production of additional copies of a nucleic acid sequence. This is generally carried out using PCR technologies. The "polymerase chain reaction" ("PCR") is well-known to those in the art. In the present invention, oligonucleotide primers are designed for use in PCR. reactions to amplify all or part of a CRISPR locus. The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent, such as DNA polymerase and at a suitable temperature and pH). In some embodiments, the primer is single stranded for maximum efficiency in amplification, although in other embodiments, the primer is double stranded. In some embodiments, the primer is an oligodeoxyribonucleotide. The primer must be sufficiently long to prime the synthesis of extension products in the presence of the inducing agent. The exact length of the primers depends on many factors including temperature, source of primer, and the use of the method. PCR primers are typically at least about 10 nucleotides in length, and most typically at least about 20 nucleotides in length. Methods for designing and conducting PCR are well known in the art, and include, but are not limited to methods using paired primers, nested primers, single specific primers, degenerate primers, gene-specific primers, vector-specific primers, partially mismatched primers, etc.

In some preferred embodiments of the present invention, a CRISPR locus or a portion thereof from a parent bacterium and a tagged bacterium are compared using any suitable method known in the art. In some preferred embodiments of the present invention, the CRISPR locus or a portion thereof from the parent bacterium and the tagged bacterium are compared by amplifying the CRISPR locus or a portion thereof. In addition to well-known cycling amplification methods (e.g., PCR, ligase chain reaction, etc.), other methods, including but not limited to isothermal amplification methods find use in the present invention. Well-known isothermal amplification methods that find use in the present invention include, but are not limited to strand displacement amplification (SDA), Q-beta-replicase, nucleic acid-based sequence amplification (NASBA), and self-sustained sequence replication.

In some other preferred embodiments of the present invention, the CRISPR locus or a portion thereof from the parent bacterium and the tagged bacterium are compared by sequencing the CRISPR locus or a portion thereof from the parent bacterium and the tagged bacterium. In some alternative embodiments, they are compared by amplifying and then sequencing the CRISPR loci or a portion thereof. In some embodiments, one end of the CRISPR loci from parent and tagged bacteria are compared, while in other embodiments, both the 5' and 3' ends of the loci are compared. In some preferred embodiments, one end (e.g., the 5' end) of the CRISPR loci are compared. In yet other embodiments, at least the last CRISPR repeat at the 3' end of the CRISPR locus and/or at least the last CRISPR spacer (e.g., the last CRISPR spacer core) at the 3' end of the CRISPR locus and/or at least the first CRISPR repeat at the 5' end of the CRISPR locus and/or at least the first CRISPR spacer (e.g., the first CRISPR spacer core) at the 5' end of the CRISPR locus are compared. In some preferred embodiments, at least the first CRISPR repeat at the 5' end of the CRISPR locus and/or at least the first CRISPR spacer (e.g., the first CRISPR spacer core) at the 5' end of the CRISPR locus are compared. In some additional preferred embodiments, at least the last CRISPR spacer (e.g., the last CRISPR spacer core) at the 3' end of the CRISPR locus and/or at least the first CRISPR spacer (e.g., the first CRISPR spacer core) at the 5' end of the CRISPR locus are compared. In some further preferred embodiments, at least the first CRISPR spacer (e.g., the first CRISPR spacer core) at the 5' ends of the CRISPR loci is compared.

In some embodiments, the CRISPR loci comprise DNA, while in other embodiments, the CRISPR loci comprise RNA. In some embodiments, the nucleic acid is of genomic origin, while in other embodiments, it is of synthetic or recombinant origin. In some embodiments, the CRISPR loci are double-stranded, while in other embodiments, they are single-stranded, whether representing the sense or antisense strand or combinations thereof. In some embodiments, CRISPR loci are prepared by use of recombinant DNA techniques (e.g., recombinant DNA), as described herein.

In the context of the present invention, the CRISPR locus is oriented based on the 5'-3' orientation of the cas genes. The cas (CRISPR-associated) genes are usually neighbouring the CRISPR loci. For example, within the chromosome of S. thermophilus strain CNRZ1066, the CRISPR1 locus is located downstream to cas genes str0657, str0658, str0659, and str0660. The CRISPR1 locus is collinearly oriented to the cas genes. Thus, the cas genes are located upstream of CRISPR1. The non-coding sequence located between the stop codon of the last cas gene and the first nucleotide of the first CRISPR repeat is located upstream to CRISPR and is referred to herein as the "CRISPR leader." The CRISPR leader is located at the 5'end of the CRISPR locus. The non-coding sequence at the opposite side of the CRISPR locus is referred to herein as the "CRISPR trailer." The CRISPR trailer starts right after the last nucleotide of the last CRISPR repeat. This last CRISPR repeat is also referred to as a "terminal repeat." The CRISPR trailer and terminal repeats are located at the 3' end of the CRISPR locus. For example, CRISPR1 leader in strain CNRZ1066 has sequence 5'-CAAGGACAGTTATTGATTTTATAATCAC-TATGTGGGTATAAAAACGTCAAAATTTCATTTGA G-3' (SEQ ID NO:12), and the CRISPR trailer has the sequence 5'-TTGATTCAACATAAAAAGCCAGTTCAAT- TGAACTMGCTTT-3' (SEQ ID NO:13). The CRISPR leader corresponds to positions 625038 to 625100, and the CRISPR trailer corresponds to positions 627845 to 627885 in the genome of *S. thermophilus* CNRZ1066 (CP000024).

As used herein the term "portion thereof" in the context of a CRISPR locus means at least about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides or even about 100 or more nucleotides (e.g., at least about 44-98 nucleotides) of a CRISPR locus In some further embodiments, the term "portion thereof" in the context of a CRISPR locus means at least the first about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides, or about 100 or more nucleotides (e.g., at least about 44-98 nucleotides) downstream from the first nucleotide of the first CRISPR repeat at the 5' end of a CRISPR locus or upstream from the last nucleotide of the last CRISPR repeat at the 3' end of a CRISPR locus. In some preferred embodiments, the term "portion thereof" refers to the at least about the first 44 nucleotides downstream from the first nucleotide of the first CRISPR repeat at the 5' end of a CRISPR locus or at least about 44 nucleotides upstream from the last nucleotide of the last CRISPR repeat at the 3' end of a CRISPR locus.

In some embodiments, the minimum size of the duplicated sequence is about 24 nucleotides and minimum size of the tagging sequence is about 20 nucleotides. Thus, in some preferred embodiments, the term "portion thereof" in the context of a CRISPR locus, means at least 44 nucleotides.

In some embodiments, the maximum size of the duplicated sequence is about 40 nucleotides and the maximum size of the tagging sequence is about 58 nucleotides. Thus, in some embodiments, the term "portion thereof" when used in the context of a CRISPR locus means at least about 98 nucleotides. In some preferred embodiments, the term "portion thereof" in the context of a CRISPR locus means at least about 44-98 nucleotides.

The present invention also provides CRISPR variants, as well as methods for generating CRISPR variants. In further embodiments, CRISPR variants are isolated, cloned and/or sequenced using methods known in the art. In some embodiments, CRISPR variants find use as targets for detection and/or identification purposes, while in alternative embodiments, CRISPR variants find use in engineering resistance against nucleic acid molecules.

C. End of a CRISPR Locus

When comparing the CRISPR locus or a portion thereof from the parent bacterium and a tagged bacterium, at least about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides, or about 100 nucleotides (e.g., at least about 44-98 nucleotides) of a CRISPR locus are compared. In some preferred embodiments, at least about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides, or about 100 or more nucleotides (e.g., at least about 44-98 nucleotides) at one or both ends of a CRISPR locus are compared.

In some preferred embodiments, at least the first about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides or about 100 or more nucleotides (e.g., at least about 44-98 nucleotides) at the 5' end of a CRISPR locus or at the 3' end of a CRISPR locus are compared. In some preferred embodiments, at least the first about 44 nucleotides at the 5' end of a CRISPR locus or the last about 44 nucleotides at the 3' end of a CRISPR locus are compared.

In some embodiments, at least the first about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides, or about 100 or more nucleotides (e.g., at least about 44-98 nucleotides) downstream from the first nucleotide of the first CRISPR repeat at the 5' end of a CRISPR locus or upstream from the last nucleotide of the last CRISPR repeat at the 3' end of a CRISPR locus are compared. In some preferred embodiments, at least about the first 44 nucleotides downstream from the first nucleotide of the first CRISPR repeat at the 5' end of a CRISPR locus or about at least 44 nucleotides upstream from the last nucleotide of the last CRISPR repeat at the 3' end of a CRISPR locus are compared.

In some embodiments, the minimum size of the duplicated sequence is about 24 nucleotides and minimum size of the tagging sequence is about 20 nucleotides. In some preferred embodiments, at least 44 nucleotides are compared. In some alternative embodiments, the maximum size of the duplicated sequence is about 40 nucleotides and the maximum size of the tagging sequence is about 58 nucleotides. In some preferred embodiments, at least 98 nucleotides are compared. In some alternative preferred embodiments, at least about 44-98 nucleotides are compared.

D. CRISPR Repeat

As used herein, the term "CRISPR repeat" has the conventional meaning as used in the art (i.e., multiple short direct repeats, which show no or very little sequence variation within a given CRISPR locus). As used herein, in context, "CRISPR repeat" is synonymous with the term "CRISPR."

A CRISPR locus comprises one or more CRISPR repeats than there are CRISPR spacers. Thus, the CRISPR repeat corresponds to the repeated sequence within a CRISPR locus. For example, except for the terminal repeat, the typical repeat sequence of the *S. thermophilus* CRISPR1 sequence is:

(SEQ ID NO: 14)
5'-gttttttgtactctcaagatttaagtaactgtacaac-3'

Point variations of this repeat sequence have been observed for repeat sequences within a CRISPR locus of a given strain and for repeat sequences within a CRISPR locus of strains from a given species, but they are very rare. Compared to this typical repeat sequence, the terminal repeat sequence of a given CRISPR locus always shows the same variation at its 3' end. Point variations of this terminal repeat sequence have also been observed but they are rare. CRISPR repeats may naturally occur in the parent bacterium. GenBank accession numbers of CRISPR1 sequences include: CP000023, CP000024, DQ072985, DQ072986, DQ072987, DQ072988, DQ072989, DQ072990, DQ072991, DQ072992, DQ072993, DQ072994, DQ072995, DQ072996, D0072997, DQ072998, DQ072999, DQ073000, DQ073001, DQ073002, DQ073003, DQ073004, DQ073005, DQ073006, DQ073007, DQ073008, and AAGS01000003.

As described in further detail herein, a duplicated sequence derived, derivable, obtained or obtainable from a parent bacterium. In some preferred embodiments, the sequence comprises the genomic DNA of a parent bacterium. In some particularly preferred embodiments, the duplicated CRISPR repeat (e.g., in the same CRISPR locus) is integrated iteratively, sequentially, simultaneously or substantially simultaneously along with the tagging sequence into the parent bacterium to give rise to a tagged bacterium.

The number of nucleotides in a repeat is generally about 20 to about 40 base pairs (e.g., about 36 base pairs). However, it is not intended that the present invention be limited any particular range within about 20 and about 40 base pairs. Indeed, it is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

In additional embodiments, the number of repeats range from about 1 to about 250. However, it is not intended that the present invention be limited any particular range within about 1 and about 250 repeats. Indeed, as indicated above, it is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. Indeed, it is intended that this apply to all numerical ranges provided herein.

In some embodiments, the CRISPR repeats comprise DNA, while in other embodiments, the CRISPR repeats comprise RNA. In some embodiments, the nucleic acid is of genomic origin, while in other embodiments, it is of synthetic or recombinant origin. In some embodiments, the CRISPR repeat genes are double-stranded or single-stranded whether representing the sense or antisense strand or combinations thereof. In some embodiments, CRISPR repeat genes are prepared by use of recombinant DNA techniques (e.g., recombinant DNA), as described herein.

In some embodiments, one or more of the CRISPR repeats are used to engineer a cell (e.g., a recipient cell). For example, in some embodiments, the CRISPR repeat(s) are inserted into the DNA of a cell (e.g., plasmid and/or genomic DNA of a recipient cell), using any suitable method known in the art. In additional embodiments, the CRISPR repeat(s) find use as a template upon which to modify (e.g., mutate) the DNA of a cell (e.g., plasmid and/or genomic DNA of a recipient cell), such that CRISPR repeat(s) are created or engineered in the DNA of the cell. In additional embodiments, the CRISPR repeat(s) are present in at least one construct, at least one plasmid, and/or at least one vector, etc. In further embodiments, the CRISPR repeats are introduced into the cell using any suitable method known in the art.

In some further embodiments, one or more cas genes or proteins are used together with or in combination with one or more, preferably, two or more CRISPR repeats and optionally one or more CRISPR spacers. In some particularly preferred embodiments, the cas gene(s) or protein(s) and CRISPR repeat(s) form a functional combination as described below.

E. CRISPR Spacer

As used herein, "CRISPR spacer" encompasses non-repetitive spacer sequences that are located between repeats (i.e., CRISPR repeats) of CRISPR loci. In some embodiments of the present invention, a "CRISPR spacer" refers to the nucleic acid segment that is flanked by two CRISPR repeats. It has been found that CRISPR spacer sequences often have significant similarities to a variety of mobile DNA molecules (e.g., bacteriophages and plasmids). In some preferred embodiments, CRISPR spacers are located between two identical CRISPR repeats. In some embodiments, CRISPR spacers are identified by sequence analysis of the DNA stretches located in between two CRISPR repeats.

Interestingly, cells carrying these CRISPR spacers have been found unable to be infected by DNA molecules containing sequences homologous to the spacers (Mojica et al. [2005], supra). In most embodiments, the CRISPR spacer is naturally present between two identical multiple short direct repeats that are palindromic.

In some embodiments, the CRISPR spacer is homologous to the target nucleic acid or a transcription product thereof or an identified sequence. Although in some embodiments, homology is taken into consideration in terms of similarity, in the context of the present invention, in some preferred embodiments, homology is expressed in terms of sequence identity. In preferred embodiments, analysis of homologous sequences includes a CRISPR spacer, which in some embodiment is at least about 70, about 75, about 80, about 85, about 90%, about 91%, about 92%, about 93%, about 94%, about 95%, about 96%, about 97%, about 98% or about 99% identical to the target nucleic acid sequence or a transcription product thereof or an identified sequence (e.g., a sequence of interest). In some embodiments, the CRISPR spacer is 100% identical to the target nucleic acid sequence.

The number of CRISPR spacers at a given CRISPR loci or locus can vary between species. In some preferred embodiments, the number of spacers ranges from about 1 to about 248. However, it is not intended that the present invention be limited any particular range within about 1 and about 140 spacers. Indeed, as indicated above, it is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. Indeed, it is intended that this apply to all numerical ranges provided herein.

In some embodiments, CRISPR spacers are identified by sequence analysis as the DNA stretches located between two repeats.

As described herein, the present invention provides methods and compositions that facilitate the use of one or more cas genes or proteins in combination with one or more, preferably, two or more CRISPR repeats suitable to confer specificity of immunity to at least one CRISPR spacer in a recipient cella In some preferred embodiments, at least one cas genes or proteins and at least one CRISPR repeat are used in functional combinations to confer specificity of immunity to at least one CRISPR spacer in a cell.

As used herein, the term "specificity of immunity" means that immunity is conferred against a specific nucleic acid sequence or transcription product thereof, using a specific CRISPR spacer or pseudo-CRISPR spacer sequence. As indicated herein, a given CRISPR spacer does not confer resistance against any nucleic acid sequence or transcription product thereof but only to those sequences against which the CRISPR spacer or pseudo-CRISPR spacer is homologous (e.g., those that are 100% identical).

In some embodiments, the CRISPR spacer(s) are obtained from a donor organism that is different from the recipient cell. In some preferred embodiments, the donor and recipient cells are different bacterial strains, species, and/or genera. In some preferred embodiments, the at least one cas genes or proteins and/or at least one CRISPR repeats are obtained from a different organism than the recipient organism. In some preferred embodiments, at least two CRISPR repeats are transferred. In some preferred embodiments, the CRISPR spacers are obtained from an organism that is heterologous to the recipient or a further donor cell from which the at least one cas genes and/or proteins, and/or at least one CRISPR repeat are obtained. In some alternative preferred embodiments, the CRISPR spacers are obtained from an organism that is homologous to the recipient or a further donor cell from which the at least one cos genes and/or proteins, and/or at least one CRISPR repeat are obtained. In some preferred embodiments, the CRISPR spacer(s) is/are designed and produced using recombinant methods known in the art. Indeed, it is intended that the CRISPR spacers be produced using any suitable method known in the art.

In some embodiments, the CRISPR spacers are heterologous to the recipient cell from which at least one cas genes or proteins and/or the at least one (in some embodiments, preferably, two or more) CRISPR repeats are obtained. In some alternative embodiments, the CRISPR spacers are homologous to the recipient cell from which at least one cas genes or proteins and/or the at least one (in some embodiments, preferably, two or more) CRISPR repeats are obtained. Indeed, it is intended that any of the elements utilized in the methods be heterologous or homologous. In some embodiments, where multiple elements are used (e.g., any combination of CRISPR spacer(s), CRISPR repeat(s), cas gene(s), and Cas protein(s)), some elements are homologous with each other and some elements are heterologous to each other (e.g., in some embodiments, the CRISPR spacer(s) and cas genes are homologous, but the CRISPR repeat(s) is/are heterologous). Thus, in some embodiments, the CRISPR spacer is not naturally associated with the CRISPR repeat and/or cas genes and/or functional CRISPR repeat-cas gene combination. Indeed, it is intended that any combination of heterologous and homologous elements find use in the present invention. In yet additional embodiments, the donor and recipient cells are heterologous, while in further embodiments, they are homologous. It is also intended that the elements contained within the donor and recipient cells be homologous and/or heterologous. The elements (e.g., CRISPR spacers) are introduced into plasmid and/or genomic DNA of the recipient cell utilizing any suitable method known in the art.

In some preferred embodiments, at least one CRISPR spacer is used to engineer a cell (e.g., a recipient cell). In further embodiments, CRISPR spacers are used as a template upon which to modify (e.g., mutate) the plasmid and/or genomic DNA of a cell (e.g., a recipient cell), such that CRISPR spacers are created in the DNA of the cell. In some embodiments, the CRISPR spacer(s) is/are cloned into at least one construct, plasmid or other vector, with which the recipient cell is then transformed, using any suitable method known in the art. CRISPR spacers are flanked by two CRISPR repeats (i.e., a CRISPR spacer has at least one CRISPR repeat on each side).

Although it is not intended that the present invention be limited to any particular mechanism, theory nor hypothesis, it is contemplated that the further a given CRISPR spacer is from the 5' end of the CRISPR locus comprising the cas gene(s) and/or the leader sequence, the lower the resistance conferred by that CRISPR spacer is. Thus, in some embodiments of the present invention, one or more of the first 100 CRISPR spacers from the 5' end of the CRISPR locus are modified, in other embodiments, one or more of the first 50 CRISPR spacers from the 5' end of the CRISPR locus are modified, in additional embodiments, one or more of the first 40 CRISPR spacers from the 5' end of the CRISPR locus are modified, in still further embodiments, one or more of the first 30 CRISPR spacers from the 5' end of the CRISPR locus are modified, in yet additional embodiments, one or more of the first 20 CRISPR spacers from the 5' end of the CRISPR locus are modified, in still more embodiments, one or more of the first 15 CRISPR spacers from the 5' end of the CRISPR locus are modified, and in some preferred embodiments, one or more of the first 10 CRISPR spacers from the 5' end of the CRISPR locus are modified. As indicated herein, different bacteria have different numbers of CRISPR spacers, thus in some embodiments various spacers are modified.

F. CRISPR Spacer Core

In some embodiments, for a specific CRISPR type within a microbial species, the CRISPR spacer is represented by a defined predominant length, although the size may vary. CRISPR types described to date have been found to contain a predominant spacer length of between about 20 bp and about 58 bp.

As used herein, the term "CRISPR spacer core" refers to the length of the shortest observed spacer within a CRISPR type. Thus, for example, within *S. thermophilus* CRISPR1, the dominant spacer length is 30 bp, with a minority of spacers between 28 bp and 32 bp in size. Thus, in *S. thermophilus* CRISPR1, the CRISPR spacer core is defined as a continuous stretch of 28 bp.

In some preferred embodiments of the present invention, the CRISPR spacer core is homologous to the target nucleic acid, a transcription product thereof, or an identified sequence over the length of the core sequence. Although homology can also be considered in terms of similarity, in some preferred embodiments of the present invention, homology is expressed in terms of sequence identity. Thus, in some embodiments, a homologous sequence encompasses a CRISPR spacer core, which may be at least about 90% identical, or at least about 91, about 92, about 93, about 94, about 95, about 96, about 97, about 98 or about 99% identical to the target nucleic acid sequence, a transcription product thereof, or an identified sequence over the length of the core sequence. In some particularly preferred embodiments, the CRISPR spacer core is 100% identical to the target nucleic acid sequence, transcription product thereof, or an identified sequence over the length of the core sequence.

During the development of the present invention, the CRISPR sequences of various *S. thermophilus* strains, including closely related industrial strains and phage-resistant variants were analyzed. Differences in the number and type of spacers were observed primarily at the CRISPR1 locus. Notably, phage sensitivity appeared to be correlated with CRISPR1 spacer content. Specifically, the spacer content was nearly identical between parental strains and phage-resistant derivatives, except for additional spacers present in the latter. These findings suggested a potential relationship between the presence of additional spacers and the differences observed in the phage sensitivity of a given strain. This observation prompted the investigation of the origin and function of additional spacers present in phage-resistant mutants.

G. Pseudo-CRISPR Spacer

As used herein, the terms "pseudo-CRISPR spacer," "pro-spacer," and "proto-spacer" refer to a nucleic acid sequence present in an organism (e.g., a donor organism, including but not limited to bacteriophage), which is preferably essential for function and/or survival and/or replication and/or infectivity, etc., and which forms a CRISPR spacer sequence. In some embodiments, the pseudo-CRISPR spacers find use in producing CRISPR spacer sequences that are complementary to or homologous to the pseudo-CRISPR spacer.

In some embodiments, at least one pseudo-CRISPR spacers and CRISPR spacer(s) that is/are complementary or homologous to at least one pseudo-CRISPR spacer(s) are used to engineer a recipient cell. In some embodiments, the pseudo-CRISPR spacers or CRISPR spacer(s) that is/are complementary or homologous to the one or more pseudo-CRISPR spacer(s) are inserted into the plasmid and/or genomic DNA of a recipient cell using any suitable method known in the art.

In some additional embodiments, the pseudo-CRISPR spacers are used as a template upon which to modify (e.g., mutate) the plasmid and/or genomic DNA of a recipient cell, such that CRISPR spacers are created in the plasmid and/or genomic DNA of the cell. In some further embodiments, the pseudo-CRISPR spacers or CRISPR spacer(s) that is/are complementary or homologous to the one or more pseudo-CRISPR spacer(s) are cloned into a construct, plasmid and/or vector, etc. is/are introduced into the host cell using any suitable method known in the art.

H. Cas Proteins and cas Genes

As used herein, the term "cas gene" has the conventional meaning as used in the art and refers to one or more car genes that are generally coupled, associated or close to or in the vicinity of flanking CRISPR loci.

A comprehensive review of the Cas protein family is presented by Haft et al. (Haft et al., Comput. Biol., 1, 6 e60 [2005]). As described therein, 41 CRISPR-associated (cas) gene families are described, in addition to the four previously known gene families. As indicated, CRISPR systems belong to different classes, with different repeat patterns, sets of genes, and species ranges. Indeed, the number of cas genes at a given CRISPR locus can vary between species.

In some embodiments, one or more of the cas genes and/or proteins naturally occur in a recipient cell and one or more heterologous spacers is/are integrated or inserted in the CRISPR loci adjacent to the one or more of the cas genes or proteins.

In some embodiments, one or more of the cas genes and/or proteins is/are heterologous to the recipient cell and one or more of the spacers is/are homologous or heterologous. In some preferred embodiments, the spacers are integrated or inserted in the CRISPR loci adjacent to the one or more of the cas gene or proteins.

CRISPR loci are typically found in the vicinity of four genes named cas1 to cas4. The most common arrangement of these genes is cas3-cas4-cas1-cas2. The Cas3 protein appears to be a helicase, whereas Cas4 resembles the RecB family of exonucleases and contains a cysteine-rich motif, suggestive of DNA binding. Cas1 is generally highly basic and is the only Cas protein found consistently in all species that contain CRISPR loci. Cas2 remains to be characterized. cas1-4 are typically characterized by their close proximity to the CRISPR loci and their broad distribution across bacterial and archaeal species. Although not all cas1-4 genes associate with all CRISPR loci, they are all found in multiple subtypes.

In addition, there is another cluster of three genes associated with CRISPR structures in many bacterial species, named here as cas1B, cas5 and cas6 (See, Bolotin et al., [2005], supra). In some embodiments, the cas gene is selected from cas1, cas2, cas3, cas4, cas1B, cas5 and/or cas6. In some embodiments, the cas gene is cas1. In yet other embodiments, the cas gene is selected from cas1, cas2, cas3, cas4, cas1B, cas5 and/or cas6 fragments, variants, homologues and/or derivatives thereof. In some additional embodiments, a combination of two or more cas genes find use, any suitable combination. It is noted that the nomenclature of the cas genes is in flux. Thus, the text herein must be taken in context.

The term "Cas protein" also encompasses a plurality of Cas proteins (e.g., between about 2 and about 12 Cas proteins, more preferably, between about 3 and about 11 Cas proteins, more preferably, between about 4 and about 10 Cas proteins, more preferably, between about 4 and about 9 Cas proteins, more preferably, between about 4 and about 8 Cas proteins, and more preferably, between about 4 and about 7 proteins genes; such as 4, 5, 6, or 7 Cas proteins).

In some embodiments, the Cas proteins are encoded by cas genes comprising DNA, while in other embodiments, the cas comprise RNA. In some embodiments, the nucleic acid is of genomic origin, while in other embodiments, it is of synthetic or recombinant origin. In some embodiments, the cas genes encoding the Cas proteins are double-stranded or single-stranded whether representing the sense or antisense strand or combinations thereof. In some embodiments, cas genes are prepared by use of recombinant DNA techniques (e.g., recombinant DNA), as described herein. U.S. Provisional Appln. Ser. No. 60/907,721, filed Mar. 3,2007, incorporated herein by reference in its entirety.

I. Bacteriophage

As used herein, the term "bacteriophage" (or "phage") has its conventional meaning as understood in the art (i.e., a virus that selectively infects one or more bacterial species). Many bacteriophages are specific to a particular genus or species or strain of bacteria. In some preferred embodiments, the phages are capable of infecting parent bacteria and/or host cells. In some embodiments, bacteriophages are virulent to the parent bacterium. In some embodiments, the phage are lytic, while in other embodiments, the phage are lysogenic.

A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells.

A lysogenic bacteriophage is one capable of entering the lysogenic pathway, in which the bacteriophage becomes a dormant, passive part of the cell's genome through prior to completion of its lytic cycle.

Bacteriophages that find use in the present invention include, but are not limited to bacteriophages that belong to any of the following virus families: Corticoviridae, Cystoviridae, Inoviridae, Leviviridae, Microviridae, Myoviridae, Podoviridae, Siphoviridae, or Tectiviridae. In some embodiments, bacteriophage that infect bacteria that are pathogenic to plants and/or animals (including humans) find particular use.

In some particularly preferred embodiments, the bacteriophage of the present invention include, but are not limited to, those bacteriophage capable of infecting a bacterium that naturally comprises one or more CRISPR loci. CRISPR loci have been identified in more than 40 prokaryotes (See e.g., Jansen et al., Mol. Microbiol., 43:1565-1575 [2002]; and Mojica et al., [2005]) including, but not limited to *Aeropyrum*, *Pyrobaculum*, *Sulfolobus*, *Archaeoglobus*, *Halocarcula*, *Methanobacterium*, *Methanococcus*, *Methanosarcina*, *Methanopyrus*, *Pyrococcus*, *Picrophilus*, *Thermoplasma*, *Corynebacterium*, *Mycobacterium*, *Streptomyces*, *Aquifex*, *Porphyromonas*, *Chlorobium*, *Thermus*, *Bacillus*, *Listeria*, *Staphylococcus*, *Clostridium*, *Thermoanaerobacter*, *Mycoplasma*, *Fusobacterium*, *Azarcus*, *Chromobacterium*, *Neisseria*, *Nitrosomonas*, *Desulfovibrio*, *Geobacter*, *Myxococcus*, *Campylobacter*, *Wolinella*, *Acinetobacter*, *Erwinia*, *Escherichia*, *Legionella*, *Methylococcus*, *Pasteurella*, *Photobacterium*, *Salmonella*, *Xanthomonas*, *Yersinia*, *Treponema*, and *Thermotoga*.

In some embodiments, the bacteriophage include, but are not limited to, those bacteriophage capable of infecting bacteria belonging to the following genera: *Escherichia*, *Shigella*, *Salmonella*, *Erwinia*, *Yersinia*, *Bacillus*, *Vibrio*, *Legionella*, *Pseudomonas*, *Neisseria*, *Bordetella*, *Helicobacter*, *Listeria*, *Agrobacterium*, *Staphylococcus*, *Streptococcus*, *Enterococcus*, *Clostridium*, *Corynebacterium*, *Mycobacterium*, *Treponema*, *Borrelia*, *Francisella*, *Brucella* and *Xanthomonas*.

In yet additional embodiments, the bacteriophage include, but are not limited to, those bacteriophage capable of infecting (or transducing) lactic acid bacteria, *Bifidobacterium*, *Brevibacterium*, *Propionibacterium*, *Lactococcus*, *Streptococcus*, *Lactobacillus* (e.g., *L. acidophilus*), *Enterococcus*, *Pediococcus*, *Leuconostoc*, and *Oenococcus*.

In still further embodiments, the bacteriophage include, but are not limited to, those bacteriophage capable of infecting *Lactococcus lactis* (e.g., *L. lactis* subsp. *lactis* and *L. lactis* subsp. *cremoris*, and *L. lactis* subsp. *lactis* biovar *diacetylactis*), *Streptococcus thermophiles*, *Lactobacillus delbrueckii* subsp. *bulgaricus*, *Lactobacillus helveticus*, *Bifidobacterium lactis*, *Lactobacillus acidophilus*, *Lactobacillus casei*, *Bifidobacterium infantis*, *Lactobacillus paracasei*, *Lactobacillus salivarius*, *Lactobacillus plantarum*, *Lactobacillus reuteri*, *Lactobacillus gasseri*, *Lactobacillus johnsonii* or *Bifidobacterium longum*.

In some particularly preferred embodiments, the bacteriophages include, but are not limited to, those bacteriophages capable of infecting bacteria that comprise one or more heterologous CRISPR loci. In some embodiments, the bacteria comprise one or more heterologous CRISPR loci, and/or one or more heterologous cas genes, and/or one or more heterologous CRISPR repeats, and/or one or more heterologous CRISPR spacers.

Infection of bacteria by phage results from the injection or transfer of phage DNA into cells. In some embodiments, infection leads to expression (i.e., transcription and translation) of the bacteriophage nucleic acid within the cell and continuation of the bacteriophage life cycle. In some embodiments involving recombinant bacteriophage, recombinant sequences within the phage genome (e.g., reporter nucleic acids), are also expressed.

It has been found that CRISPR spacer sequences in prokaryotes often have significant similarities to a variety of DNA molecules, including such genetic elements as chromosomes, bacteriophages, and conjugative plasmids. It has been reported that cells carrying these CRISPR spacers are unable to be infected by DNA molecules containing sequences homologous to the spacers (See, Mojica et al., [2005]).

In some embodiments of the present invention, the parent bacteria are exposed (e.g., iteratively, sequentially, simultaneously or substantially simultaneously) to more than one bacteriophage. In some preferred embodiments, the bacteria are exposed to mixtures of one or more (e.g., several) different phages. In some alternative preferred embodiments, the parent bacteria are sensitive to each of the bacteriophages to which they are exposed.

In some embodiments, each of the tagging sequences from each of the bacteriophages and/or each of the duplicated sequences (e.g., the duplicated CRISPR repeat) from the parent bacterium integrate into the same CRISPR locus. In other embodiments, each of the tagging sequences and/or each of the duplicated sequences integrate at one or both ends of the same CRISPR locus. In yet additional embodiments, each of the tagging sequences and/or each of the duplicated sequences integrate at the 5' and/or the 3' end of the same CRISPR locus. In some preferred embodiments, each of the tagging sequences and/or each of the duplicated sequences integrate at the 5' end of the same CRISPR locus.

In some embodiments, each of the tagging sequences and/or each of the duplicated sequences from the parent bacteria integrate iteratively, simultaneously or substantially simultaneously. In embodiments in which each of the tagging sequences and/or each of the duplicated sequences are integrated sequentially, the first tagging sequence and/or the first duplicated sequence is integrated into the parent bacteria. A second tagging sequence from a second bacteriophage and/or another duplicated sequence are then integrated into the parent bacterium. In some preferred embodiments, the tagging sequence and/or the duplicated sequence integrate into the chromosomal DNA of the parent bacteria.

In some embodiments, each of the tagging sequences and/or each of the duplicated sequences integrate into one end (e.g., the 5' end) of the same CRISPR locus adjacent (i.e., next to) each other. Thus, in some embodiments, each of the tagging sequences and/or duplicated sequences integrate sequentially, whereby the first sequences are integrated into the parent bacterium at one end (e.g., within or at the 5' and/or the 3' end) of the CRISPR locus. In some preferred embodiments, a second tagging sequence and/or duplicated sequence is then integrated into the parent bacteria adjacent (e.g., directly adjacent) to the first pair of sequences. In some embodiments, the second sequences integrate into the parent bacterium adjacent (e.g., directly adjacent) to the 5' or the 3' end of the first sequences. In some preferred embodiments, the second sequences integrate into the parent bacterium adjacent (e.g., directly adjacent) to the 3' end of the first sequences. In embodiments in which additional sequences are provided, these are then integrated.

In some embodiments, each of the sequences integrate adjacent (i.e., next to) each other within or at the 3' end and/or at the 5' end of the same CRISPR locus of the parent bacteria. In some preferred embodiments, each of the sequences integrate adjacent (i.e., next to) each other at the 5' end of the same CRISPR locus of the parent bacteria. In some particularly preferred embodiments, each of the sequences integrate adjacent (i.e., next to) each other upstream of the 5' end of the CRISPR locus of the parent bacteria. In some alternatively preferred embodiments, each of the sequences integrate adjacent (i.e., next to) each other, in a location that is upstream of the 5' CRISPR repeat of the CRISPR locus of the parent bacteria. In some more particularly preferred embodiments, each of the sequences integrate adjacent (i.e., next to) each other upstream of the first 5' CRISPR repeat of the CRISPR locus of the parent bacterium.

J. Parent Bacteria

As used herein the terms "parent bacterium" "parent bacteria" and "parental strain" refer to any bacterium/bacteria/strains that is/are exposed to one or more virulent bacteriophage. In some particularly preferred embodiments, the parent bacteria are sensitive to the virulent phage. In some preferred embodiments, the parental strain is infected by the bacteriophage. In some particularly preferred embodiments, the infection by phage renders the parent bacterium/bacteria/strain or a subpopulation thereof insensitive to further infection by the bacteriophage. In some preferred embodiments, the infection of a "parent bacterium" by one or more bacteriophage results in the creation of a tagged strain that can be selected based on its insensitivity to the bacteriophage. In some preferred embodiments, "bacteriophage resistant mutant" are bacteria that are tagged or tagged according to the methods of the present invention. In some embodiments, the parent bacteria are wild-type bacterial strains. In some preferred embodiments, the parent bacteria are wild-type strains of bacteria that have not been previously infected with any bacteriophage. In some preferred embodiments, the parent bacteria are wild-type strains of bacteria that have not been previously tagged, while in some alternative embodiments, the patent bacteria are bacteriophage resistant mutants that have been previously tagged.

In some particularly preferred embodiments, the parent bacterium is selected from any bacterium that naturally comprises one or more CRISPR loci. CRISPR loci have been identified in more than 40 prokaryotes (Jansen et al. [2002) supra; Mojica et al., [2005], supra; and Haft et al., [2005], supra) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium. Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema* and *Thermotoga*.

In some embodiments, the parent bacterium comprises one or more heterologous CRISPR spacers, one or more heterologous CRISPR repeats, and/or one or more heterologous cas genes. In some alternative embodiments, the parent bacterium comprises one or more heterologous CRISPR loci, preferably, one or more complete CRISPR loci. In some further embodiments, the parent bacterium naturally comprises one or more CRISPR loci and also comprises one or more heterologous CRISPR spacers, one or more heterologous CRISPR repeats, and/or one or more heterologous cas genes. In some additional embodiments, the parent bacterium naturally comprises one or more CRISPR loci and also comprises one or more heterologous CRISPR loci, preferably, one or more complete CRISPR loci.

In some preferred embodiments, the phage-resistant subpopulation created by exposure of the parent bacteria to at least one phage is a pure culture. However, it is not intended that the present invention be limited to pure cultures of bacterial strains, variants, or phage. Indeed, it is intended that the present invention encompasses mixed cultures of cells and phage. In some embodiments, the mixed culture is a mix of different mutants corresponding to different integration events at the same and/or at different CRISPR loci.

Although it is not intended that the present invention be so limited, preferred parental bacterial genera are *Streptococcus* and *Lactobacillus*. Indeed, it is intended that any bacterial species will find use in the present invention, including but not limited to *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Bifidobacterium, Brevibacterium, Propionibacterium, Lactococcus, Lactobacillus, Enterococcus, Pediococcus, Leuconostoc, Oenococcus*, and/or *Xanthomonas*. In some embodiments, the parent bacteria are or are derived from lactic acid bacteria, including but not limited to *Bifidobacterium, Brevibacterium, Propionibacterium, Lactococcus, Streptococcus, Lactobacillus* (e.g., *L. acidophilus*), *Enterococcus, Pediococcus, Leuconostoc*, and/or *Oenococcus*. In further embodiments, the parent bacteria are or are derived from *Lactococcus lactis* (e.g., *L. lactis* subsp. *lactis* and *L. lactis* subsp. *cremoris*, and *L. lactis* subsp. *lactis* biovar *diacetylactis*), *L. delbrueckii* subsp. *bulgaricus, L. helveticus, L. acidophilus, L. casei, L. paracasei, L. salivarius, L. plantarum, L. reuteri, L. gasseri, L. johnsonii, Bifidobacterium lactis, B. infantis, B. longum*, and/or *Streptococcus thermophilus*.

In embodiments of the present invention, the parent bacterium is a "food-grade bacterium" (i.e., a bacterium that is used and generally regarded as safe for use in the preparation and/or production of food and/or feed). In some preferred embodiments, the parent bacterium is suitable for use as a starter culture, a probiotic culture, and/or a dietary supplement. In additional embodiments, the parent bacterium finds use in the fermentation of meat (e.g., beef, pork, lamb, and poultry) including, but not limited to, lactic acid bacteria, *Pediococcus cerevisiae, Lactobacillus plantarum, L. brevis, L. sakei, L. curvatus, Micrococcus* species, *Pediococcus pentosaceus, Staphylococcus xylosus, S. vitulinus* and mixtures thereof (See e.g., Knorr (ed.), *Food Biotechnology*, at 538-39 [1987]; and Pederson, *Microbiology of Fermented Foods*, at 210-34, 2d ed., [1979]; and U.S. Pat. No. 2,225,783, herein incorporated by reference in its entirety). In yet additional embodiments, he parent bacterium finds use in the fermentation of vegetables (e.g., carrots, cucumbers, tomatoes, peppers, and cabbage) including, but not limited to, *L. plantatum, L. brevis, Leuconostoc mesenteroides, Pediococcus pentosaceus*, and mixtures thereof (See e.g., Knorr, supra; Pederson, supra; and U.S. Pat. Nos. 3,024,116, 3,403,032, 3,932,674, and 3,897,307). In yet further embodiments, the parent bacterium finds use in the fermentation of dough formed from cereals (e.g., wheat, rye, rice, oats, barley, and corn). In still further embodiments, the parent bacterium finds use in the production of wine through fermentation of fruit juice (e.g., grape juice). In some additional embodiments, parent bacterium finds use in the fermentation of milk (e.g., *L. delbrueckii* subsp. *bulgaricus, L. acidophilus, S. thermophilus*, and mixtures thereof (See, Knorr, supra; and Pederson supra, at pages 105-35). In some preferred embodiments, the parent bacterium find use in the production of cheese, including but not limited to *L. delbrueckii* subsp. *bulgaricus. L. helveticus, L. lactis* subsp. *lactis, L lactis* subsp. *cremoris, L. lactis* subsp. *lactis biovar diacetylactis, S. thermophilus, Bifidobacterium Enterococcus*, etc., and mixtures thereof (See e.g., Knorr, supra, and Pederson, supra, at 135-51). In yet further embodiments, the parent bacterium finds use in the fermentation of eggs, including but not limited to *Pediococcus pentosaceus, Lactobacillus plantarum*, and mixtures thereof (See, Knorr, supra). In some embodiments, the parent bacterium is finds use in fermentation to produce various products, including but not limited to cheddar and cottage cheese (e.g., *L. lactis* subsp. *lactis, L. lactis* subsp. *cremoris*), yogurt (*L. delbrueckii* subsp. *bulgaricus*, and *S. thermophilus*), Swiss cheese (e.g., *S. thermophilus, L. lactis*, and *L. helveticus*), blue cheese (*Leuconostoc cremoris*), Italian cheese (*L. bulgaricus* and *S. thermophilus*), viili (*L. lactis* subsp. *cremoris, L. lactis* subsp. *lactis biovar diacetylactis, Leuconostoc cremoris*), yakult (*L. casei*), casein (*L. lactis* subsp. *cremoris*), natto (*Bacillus subtilis* var. *natto*), wine (*Leuconostoc oenos*), sake (*Leuconostoc mesenteroides*), polymyxin (*Bacillus polymyxa*), colistin (*Bacillus colistrium*), bacitracin (*Bacillus licheniformis*), L-Glutamic acid (*Brevibacterium lactofermentum* and *Microbacterium ammoniaphilum*), and acetone and butanol (*Clostridium acetobutyricum*, and *Clostridium saccharoperbutylacetonicum*). In some preferred embodiments, the parent bacterial species are selected from *S. thermophilus, L. delbrueckii* subsp. *bulgaricus* and/or *L. acidophilus*.

In yet additional embodiments, the parent bacteria find use in methods including but not limited to antibiotic production, amino acid production, solvent production, and the production of other economically useful materials. In still other embodiments the parent bacteria find use in cosmetic, therapeutic, and/or pharmaceutical compositions. In some embodiments the compositions have particular activities, including but not limited to regenerating the skin, including but not limited to anti-wrinkle properties, erasing old scars, repairing burn-damaged tissues, promoting skin healing, eliminating pigmentary spots, etc. In some embodiments, the compositions either promote or inhibit the growth of nails, hair or hairs. In some additional embodiments, the compositions comprise at least one microbial culture and/or tagged bacterium and/or a cell culture produced using the methods and compositions of the present invention In further embodiments, the parent bacteria are bacteriophage insensitive mutants. Thus, in some embodiments, the parent bacteria are insensitive to one or more bacteriophage. In some preferred embodiments, the parent bacterium is not a bacteriophage insensitive mutant for the bacteriophage that it is to be exposed to during use of the present invention.

K. Tagging Sequence

As used herein, the term "tagging sequence" refers to the portion of an "additional repeat-spacer unit" that is derived, derivable, obtained or obtainable from the genome of one or more bacteriophage(s)) that the parent bacterium is exposed to in accordance with the methods of the present invention and is used as a label or a tag (e.g., a unique label or a unique tag). In some preferred embodiments, the tagging sequence is at least about 20 nucleotides in length, while in some more preferred embodiments, the tagging sequence is from about 20 to about 58 nucleotides in length. However, in some alternative embodiments, a "tag" is generated using genetic elements from sources other than phage. For example, in some embodiments, the tag is provided by plasmids, transposable elements, isolated nucleic acid, etc. Indeed, in some embodiments, the tag is a unique, synthetic, non-functional sequence. Thus, it is not intended that the present invention be limited to nucleic acid tags that are generated solely from phage nucleic acid.

The tagging sequence is typically a sequence that is a naturally occurring sequence in the bacteriophage. Preferably, the tagging sequence has at least about 90%, about 95%, about 96%, about 97%, about 98%, or about 99% identity to the naturally occurring sequence in the bacteriophage (e.g., the genome of the bacteriophage from which it is derived, derivable, obtained or obtainable). In some highly preferred embodiments, the tagging sequence has 100% identity to the naturally occurring sequence in the bacteriophage(e.g., the genome of the bacteriophage from which it is derived, derivable, obtained or obtainable).

In some embodiments, the tagging sequence has less than about 40%, about 30%, about 20%, about 10%, about 5%, about 4%, about 3%, about 2%, about 1% or about 0% identity to any other CRISPR spacers or CRISPR spacer cores in the one or more CRISPR loci of the tagged bacterium. In some embodiments, the tagging sequence has less than about 40%, about 30%, about 20%, about 10%, about 5%, about 4%, about 3%, about 2%, about 1%, or about 0% identity to any other sequence in the one or more CRISPR loci of the tagged bacterium.

In some alternative embodiments, the tagging sequence is a sequence that is identical to a sequence (e.g., a CRISPR spacer) in the CRISPR locus of the bacterium. In some alternative embodiments, the tagging sequence is a sequence that is almost identical to a sequence (e.g., a CRISPR spacer) in the CRISPR locus of the bacterium in that it contains one or more single nucleotide polymorphisms (e.g., one or two single nucleotide polymorphisms).

In some embodiments, at least one tagging sequence is integrated into the parent bacterium. In some alternative embodiments, at least one duplicated sequence (e.g., a duplicated CRISPR repeat sequence) that is derived, derivable, obtained or obtainable from the parent bacterium's genome or one or more of the parent bacterium's plasmids (e.g., megaplasmids) is also integrated. In some particularly preferred embodiments, at least one duplicated sequence is copied or replicated from the genome of the parent bacterium. In some embodiments, the CRISPR repeat sequence in a CRISPR locus is duplicated and the tagging sequence is integrated in the bacterium's genome immediately after (e.g., downstream) the new duplicated CRISPR repeat. However, it is not intended that the present invention be limited to any specific mechanism or theory of action.

In some highly preferred embodiments, the at least one duplicated sequence is a CRISPR repeat sequence that has at least about 90%, about 95%, about 96%, about 97%, about 98%, or about 99% identity to the CRISPR repeats in the one or more CRISPR loci of the parent bacterium and/or tagged bacterium. In some particularly preferred embodiments, the at least one duplicated sequence is a CRISPR repeat sequence that has at least about 100% identity to the CRISPR repeats in the one or more CRISPR loci of the parent bacterium and/or tagged bacterium. In some embodiments, the duplicated sequence is at least about 24 nucleotides in length, while in some preferred embodiments, the duplicated sequence is between about 24 and about 40 nucleotides in length.

In some preferred embodiments, the at least one tagging sequence and the at least one duplicated sequence are integrated into the parent bacterium. In some embodiments, each time a tagging sequence is integrated into the genome of the parent bacterium, it is accompanied by the iterative, sequential, simultaneous or substantially simultaneous integration of at least one duplicated sequence. Accordingly, at least one pair of sequences comprising the tagging sequence and the duplicated sequence is integrated into the parent bacterium, thereby resulting in a tagged bacterium. However, it is not intended that the present invention be limited to any specific mechanism or means of action.

In some preferred embodiments, the at least one tagging sequence and the at least one duplicated sequence integrate adjacent to each other. In some particularly preferred embodiments, the at least one tagging sequence and the at least one duplicated sequence integrate directly adjacent to each other such that there are no intervening nucleotides between the sequences.

In some embodiments, the duplicated sequence is attached, linked or fused to one end (e.g., the 5' or the 3' end) of the tagging sequence. In some preferred embodiments, the duplicated sequence is attached, linked or fused to the 5' end of the tagging sequence. In some particularly preferred embodiments, fusion of a duplicated sequence with a tagging sequence forms a CRISPR spacer repeat unit. Accordingly, in some embodiments, following the integration of a CRISPR spacer repeat unit, the duplicated sequence is the first sequence at the 5' end of the CRISPR locus and the tagging sequence is the second (i.e., the next) sequence in the CRISPR locus, downstream of the duplicated sequence. In yet further preferred embodiments, the sequences within a CRISPR spacer repeat unit are directly attached, directly linked or directly fused such that there are no intervening nucleotides between the duplicated sequence and the tagging sequence.

In some particularly preferred embodiments, a CRISPR spacer repeat unit is integrated into the genome of the parent bacterium to produce a tagged bacterium. In some preferred embodiments, the duplicated sequence is derived, derivable, obtained or obtainable from the parent bacterium's genome. In some additional embodiments, the tagging sequence is derived, derivable, obtained or obtainable from the genome of the bacteriophage that is used to infect the parent bacterium.

In some further embodiments, multiple CRISPR spacer repeat units are integrated into the genome of the parent bacterium. In some embodiments, the multiple CRISPR spacer repeat units comprise a first CRISPR spacer repeat unit comprising a duplicated sequence and a tagging sequence and a second CRISPR spacer repeat unit comprising a second duplicated sequence and a second tagging sequence. In some preferred embodiments, the second duplicated sequence typically has the same sequence (e.g., greater than about 95%, about 96,%, about 97%, about 98%, about 99%, or about 100% identity) as the first duplicated sequence. In some embodiments, the tagging sequence typically has a different sequence (e.g., less than about 40%, about 30%, about 20%, about 10%, about 5%, about 4%, about 3%, about 2%, about 1% or about 0% identity) to the first tagging sequence. This is also the case in embodiments containing further integrated CRISPR spacer repeat unit sequences.

In some preferred embodiments, the configuration of the multiple CRISPR spacer repeat units is typically:
[duplicated sequence-tagging sequence]$_n$
wherein n=2, 3, 4, 5, or ≥6.

In some particularly preferred, embodiments, the configuration of the multiple CRISPR spacer repeat units is typically:
[CRISPR repeat-tagging sequence]$_n$
wherein n=2, 3, 4, 5, or ≥6.

In some preferred embodiments, the configuration of the multiple CRISPR spacer repeat units is:
5'-[duplicated sequence-tagging sequence]$_n$-3'
wherein n=2, 3, 4, 5,or ≥6.

In some particularly preferred embodiments, the configuration of the multiple CRISPR spacer repeat units is:
5'-[CRISPR repeat-tagging sequence]$_n$-3'
wherein n=2, 3, 4, 5, or ≥6.

In some preferred embodiments, multiple CRISPR spacer repeat units are integrated into the parent bacterium.

In some embodiments, the tagging sequence portion of the CRISPR spacer repeat unit is integrated adjacent to: (i) a duplicated sequence that is homologous (e.g., identical) to a naturally occurring sequence in the parent bacterium; (ii) a duplicated sequence that is homologous (e.g., identical) to a naturally occurring sequence in the CRISPR locus of the parent bacterium; or (iii) most preferably, a duplicated sequence that is homologous (e.g., identical) to a naturally occurring CRISPR repeat in the CRISPR locus of the parent bacterium.

Following each exposure of a parent bacterium to a given bacteriophage in independent experiments, the tagging sequence in each of the tagged bacterium is presented a different nucleotide sequence, thereby creating a sequence that was unique to each bacterium. Thus, upon exposure of a parent bacterium to a given bacteriophage, the tagging sequence that is integrated into a parent bacterium is selected from the genome of the bacteriophage. As indicated above, it is not intended that the present invention be limited to random integration events nor any particular mechanism nor means of action.

This surprising finding was used in the development of the present invention, as the selected tagging sequence provides a unique tag or label in the tagged bacterium. Surprisingly, it was also found that when the same parent bacterium is exposed to the same bacteriophage, the tagging sequence that is integrated in independent/distinct experiments is of a different sequence, thereby resulting in a unique label in the tagged bacterium following each exposure.

In some embodiments, a randomly selected tagging sequence is identified in the tagged bacterium by virtue of one or more of the following properties of the tagging sequence: (1) the location of the tagging sequence in the one or more CRISPR loci of the bacteriophage insensitive mutant (as indicated herein, the tagging sequence is typically located at one and/or both the 5' and/or 3' ends (more preferably, the 5' end) of the CRISPR locus of the tagged bacterium; (2) the tagging sequence has a high degree of homology or identity (e.g., 100% identity) to a sequence in the bacteriophage genome that the parent bacterium was exposed to; and/or (3) the tagging sequence is fused, linked or attached to (e.g., directly fused, linked or attached to) at least one sequence (e.g., a CRISPR repeat; i.e., a "CRISPR spacer repeat unit) that is duplicated from the genome of the parent bacterium. Typically, as described herein, this CRISPR spacer repeat unit is located at one and/or both ends (e.g., the 5' and/or 3' end; more preferably, the 5' end) of the CRISPR locus of the tagged bacterium. Thus, in some embodiments, CRISPR spacer repeat units integrates at both ends of the CRISPR locus of the parent bacterium such that the sequences are at the 5' end and the 3' end of the CRISPR locus. In some additional embodiments, one of the duplicated sequences is the first sequence at the 5' end of the CRISPR locus and the tagging sequence is located immediately downstream of the duplicated sequence. In some embodiments, the other duplicated sequence is the last sequence at the 3' end of the CRISPR locus and the tagging sequence is immediately upstream of the duplicated sequence.

In some preferred embodiments, the tagging sequence(s) and/or the duplicated sequence(s) of the CRISPR spacer repeat unit integrate at one end of the CRISPR locus of the parent bacterium such that the sequence(s) are at the 3' end of the CRISPR locus. In some further embodiments, the duplicated sequence is the last sequence at the 3' end of the CRISPR locus and the tagging sequence is located immediately upstream of the duplicated sequence. In some preferred embodiments, the tagging sequence(s) and/or the duplicated sequence(s) integrate at one end of the CRISPR locus of the parent bacterium such that the sequences are at the 5' end of the CRISPR locus. In some embodiments, the duplicated sequence is the first sequence at the 5' end of the CRISPR locus and the tagging sequence is immediately downstream of the duplicated sequence.

As described herein, the tagging sequence(s) is a strain specific tag in the sense that the tagging sequence that is integrated or inserted from the bacteriophage into the parent bacterium is different each time the parent bacterium (e.g., the same parent bacterium) is exposed to the bacteriophage (e.g., the same bacteriophage). Hence, the tagging sequence finds use as a unique tag for a given bacterial strain.

In some embodiments, the tagging sequence(s) and/or the duplicated sequence(s) integrate into one or more CRISPR loci. In some alternative embodiments, the tagging sequence(s) and/or the duplicated sequence(s) integrate into one or more different CRISPR loci. In further embodiments, two or more different tagging sequence(s) and/or duplicated sequence(s) integrate into one CRISPR locus. In yet additional embodiments, two or more different tagging sequence(s) and/or duplicated sequence(s) each integrate into two or more different CRISPR loci.

L. Tagged CRISPR Loci

The genome of *Streptococcus thermophilus* LMG18311 contains 3 CRISPR loci; the 36-bp repeated sequences are different in CRISPR1 (34 repeats), CRISPR2 (5 repeats), and CRISPR3 (a single sequence). Nevertheless, they are perfectly conserved within each locus. CRISPR1 and CRISPR2 repeats are respectively interspaced by 33 and 4 sequences of 30 bp in length. All these interspacing sequences are different from each other. They are also different from those found in strain CNRZ1066 (41 interspacing sequences within CRISPR1) and in strain LMD-9 (16 within CRISPR1 and 8 within CRISPR3), which both are *S. thermophilus*.

*Streptococcus thermophilus* strain DGCC7710 (deposited at the French "Collection Nationale de Cultures de Microorganismes" under number CNCM 1-2423) possesses at least 3 CRISPR loci: CRISPR1, CRISPR2, and CRISPR3. In strains CNRZ1066 and LMG18311 for which the complete genome sequence is known (Bolotin et al., [2004] supra), CRISPR1 is located at the same chromosomal locus: between str0660 (or stu0660) and str0661 (or stu0661). In strain DGCC7710, CRISPR1 is located between highly similar genes. CRISPR1 of strain DGCC7710 contains 33 repeats (including the terminal repeat), and thus 32 spacers. Each of these spacers are different from each other. While most of these spacers are new (i.e., not previously identified within CRISPR loci), four spacers close to the CRISPR1 trailer are identical to already known CRISPR1 spacers. These four include: the $28^{th}$ spacer of DGCC7710, which is 100% identical to the $31^{st}$ CRISPR1 spacer of strain CNRZ1575 (Genbank accession number DQ072991); the $30^{th}$ spacer of DGCC7710, which is 100% identical to the $27^{th}$ CRISPR1 spacer of strain CNRZ703 (Genbank accession number DQ072990); the $31^{st}$ spacer of DGCC7710, which is 100% identical to the $28^{th}$ CRISPR1 spacer of strain CNRZ703 (Genbank accession number DQ072990); and the $32^{nd}$ spacer of DGCC7710, which is 100% identical to the $30^{th}$ CRISPR1 spacer of strain CNRZ703 (Genbank accession number DQ072990). The CRISPR1 sequence (5'-3') of strain DGCC7710 is shown in SEQ ID NO:1.

*Streptococcus thermophilus* strain DGCC7778 was isolated as a natural phage resistant mutant using DGCC7710 as the parental strain, and phage D858 as the virulent phage. The CRISPR1 of strain DGCC7778 contains 35 repeats (including the terminal repeat), and thus 34 spacers. When compared to the CRISPR1 sequence of DGCC7710, the CRISPR1 sequence of DGCC7778 possesses two additional, adjacent, new spacers, as well as two additional repeats which flank the new spacers, at one end of the CRISPR locus (i.e., close to the leader). All of the other spacers of CRISPR1 locus are unchanged. The CRISPR1 sequence (5'-3') of strain DGCC7778 is shown in SEQ ID NO:2.

Thus, in the case of DGCC7778, the first spacer (5'-caacacattcaacagattaatgaagaatac-3' [SEQ ID NO:3] and the second spacer (5'-tccactcacgtacaaatagtgagtgtactc-3' [SEQ ID NO:4]) constitute the strain-specific tag which identifies this tagged strain. During the development of the present invention, it was shown that the sequence of both new spacers exists within the D858 phage genome. The sequence of the second new spacer is located between positions 25471 and 25442 bp (i.e., on the minus strand) of the D858 genome, with one mismatch (96.7% of identical nucleotides over 30 nucleotides). The sequence of the first spacer is located between positions 31481 and 31410 bp (i.e., on the plus strand) of the D858 genome (100% of identical nucleotides over 30 nucleotides). Although it is not intended that the present invention be limited to any particular mechanism nor theory, the fact that two new spacers present in the CRISPR1 locus of DGCC7778 are needed to confer to strain DGCC7778 resistance to phage D858, it is contemplated that spacer "2" was first inserted into the CRISPR1 locus of DGCC7710 (33 repeats and 32 spacers), at one end of this CRISPR locus, together with one repeat. This insertion gave rise to a bacteriophage insensitive mutant (intermediate strain), tagged with this additional new spacer (i.e., now bearing 34 repeats and 33 spacers). This spacer is derived from the D858 genome, but a replication error or reverse transcription error, likely occurred during the insertion process, leading to one point mutation. Due to the imperfect match (i.e., 1 mismatch) between this newly acquired spacer and the targeted phage sequence, the efficiency of resistance of this intermediate strain to phage D858 was low.

However, a second event of spacer insertion occurred in this intermediate strain (i.e., the strain more resistant to phage D858 than parental strain DGCC7710, but not "fully" resistant because of the mismatch), leading to the insertion of a second new spacer (the spacer "1" as found in DGCC7778) at the same end of CRISPR1 locus, together with one repeat. This second insertion gave rise to a new bacteriophage insensitive mutant, which was isolated and named DGCC7778. DGCC7778 is more resistant to D858 than the intermediate strain, and much more resistant than parental strain DGCC7710, due to the presence of spacer "1," which is 100% identical to the targeted phage sequence.

*Streptococcus thermophilus* strain DGCC7710-RH1 was isolated as a natural phage resistant mutant using DGCC7710 as the parent strain and phage D858 as the virulent phage. The CRISPR1 of strain DGCC7710-RH1 contains 34 repeats (including the terminal repeat), and 33 spacers. When compared to the CRISPR1 sequence of *Streptococcus thermophilus* strain DGCC7710, the CRISPR1 sequence of *Streptococcus thermophilus* strain DGCC7710-RH1 possesses one additional new spacer (i.e., tagging sequence) and one additional repeat which flanks the new spacer, at one end of the CRISPR locus (i.e., close to the leader, at the 5' end of the CRISPR locus). All the other spacers of CRISPR1 locus were unchanged. The CRISPR1 sequence (5'-3') of strain DGCC7710-RH1 is:

```
                                                                    (SEQ ID NO: 5)
caaggacagttattgattttataatcactatgtgggtataaaaacgtcaaaatttcatttgag GTTTTTGTACTCTCAAGATTTAAGTAACTGTACAACtcaacaattgcaacatcttataacccactt GTTTTTGTACTCTCAAGATTTAAGTAACTGTACAACtgtttgacagcaaatcaagattcgaattgt GTTTTTGTACTCTCAAGATTTAAGTAACTGTACAACaatgacgaggagctattggcacaacttaca GTTTTTGTACTCTCAAGATTTAAGTAACTGTACAACcgatttgacaatctgctgaccactgttatc GTTTTTGTACTCTCAAGATTTAAGTAACTGTACAACacacttggcaggcttattactcaacagcga GTTTTTGTACTCTCAAGATTTAAGTAACTGTACAACctgttccttgttcttttgttgtatcttttc GTTTTTGTACTCTCAAGATTTAAGTAACTGTACAACttcattcttccgttttgtttgcgaatcct GTTTTTGTACTCTCAAGATTTAAGTAACTGTACAACgctggcgaggaaacgaacaaggcctcaaca GTTTTTGTACTCTCAAGATTTAAGTAACTGTACAACcatagagtggaaaactagaaacagattcaa GTTTTTGTACTCTCAAGATTTAAGTAACTGTACAACataatgccgttgaattacacggcaaggtca GTTTTTGTACTCTCAAGATTTAAGTAACTGTACAACgagcgagctcgaaataatcttaattacaag GTTTTTGTACTCTCAAGATTTAAGTAACTGTACAACgttcgctagcgtcatgtggtaacgtattta GTTTTTGTACTCTCAAGATTTAAGTAACTGTACAACggcgtcccaatcctgattaatacttactcg GTTTTTGTACTCTCAAGATTTAAGTAACTGTACAACaacacagcaagacaagaggatgatgctatg GTTTTTGTACTCTCAAGATTTAAGTAACTGTACAACcgacacaagaacgtatgcaagagttcaag GTTTTTGTACTCTCAAGATTTAAGTAACTGTACAACacaattcttcatccggtaactgctcaagtg GTTTTTGTACTCTCAAGATTTAAGTAACTGTACAACaattaagggcatagaaagggagacaacatg GTTTTTGTACTCTCAAGATTTAAGTAACTGTACAACcgatatttaaaatcattttcataacttcat GTTTTTGTACTCTCAAGATTTAAGTAACTGTACAACgcagtatcagcaagcaagctgttagttact GTTTTTGTACTCTCAAGATTTAAGTAACTGTACAACataaactatgaaattttataattttaaga GTTTTTGTACTCTCAAGATTTAAGTAACTGTACAACaataatttatggtatagcttaatatcattg GTTTTTGTACTCTCAAGATTTAAGTAACTGTACAACtgcatcgagcacgttcgagtttaccgtttc GTTTTTGTACTCTCAAGATTTAAGTAACTGTACAACtctatatcgaggtcaactaacaattatgct GTTTTTGTACTCTCAAGATTTAAGTAACTGTACAACaatcgttcaaattctgttttaggtacattt GTTTTTGTACTCTCAAGATTTAAGTAACTGTACAACaatcaatacgacaagagttaaaatggtctt GTTTTTGTACTCTCAAGATTTAAGTAACTGTACAACgcttagctgtccaatccacgaacgtggatg GTTTTTGTACTCTCAAGATTTAAGTAACTGTACAACcaaccaacggtaacagctactttttacagt GTTTTTGTACTCTCAAGATTTAAGTAACTGTACAACataactgaaggataggagcttgtaaagtct GTTTTTGTACTCTCAAGATTTAAGTAACTGTACAACtaatgctacatctcaaaggatgatcccaga GTTTTTGTACTCTCAAGATTTAAGTAACTGTACAACaagtagttgatgacctctacaatggtttat GTTTTTGTACTCTCAAGATTTAAGTAACTGTACAACcctagaagcatttgagcgtatattgattg GTTTTTGTACTCTCAAGATTTAAGTAACTGTACAACaattttgccccttctttgcccttgactag
```

```
GTTTTTGTACTCTCAAGATTTAAGTAACTGTACAACaccattagcaatcatttgtgcccattgagt

GTTTTTGTACTCTCAAGATTTAAGTAACTGTACAGTttgattcaacataaaaagccagttcaattgaacttggcttt
```

The leader sequence of this CRISPR1 is:

5' caaggacagttattgatmataatcactatgtgggtataaaaaacgtcaaaaM-catttgag 3' (SEQ ID NO:6). The integrated sequence comprising CRISPR repeats is shown in upper case, while the CRISPR spacers are shown in lower case. In this sequence, the terminal repeat has the sequence 5' gttttgtactctcaagatt-taagtaactgtacagt 3' (SEQ ID NO:7), while the trailer sequence is has the sequence: 5' ttgattcaacataaaaagccagt-tcaattgaacttggcttt 3' (SEQ ID NO:8). Thus, for *S. thermophilus* strain DGCC7710-RH1, the spacer (5'-tcaacaattg-caacatcttataacccactt-3' [SEQ ID NO:9]) constitutes the strain-specific tagging sequence which identifies this mutant strain (i.e., the tagged bacterium). The sequence of the new spacer (i.e., the tagging sequence) is present within the D858 phage genome.

The sequence of the spacer is found between positions 31921 and 31950 bp (i.e., on the plus strand) of the D858 genome (and has 100% identity to the D858 genomic sequence over 30 nucleotides). The new spacer (i.e., the tagging sequence) that is integrated into the CRISPR1 locus of *S. thermophilus* strain DGCC7710-RH1 confers resistance to phage D858 to this strain.

*S. thermophilus* strain DGCC7710-RH2 was isolated as a natural phage resistant mutant using *S. thermophilus* strain DGCC7710 as the parental strain, and phage D858 as the virulent phage. The CRISPR1 of *S. thermophilus* strain DGCC7710-RH2 contains 34 repeats (including the terminal repeat) and 33 spacers. When compared to the CRISPR1 sequence of *S. thermophilus* strain DGCC7710, the CRISPR1 sequence of *S. thermophilus* strain DGCC7710-RH2 possesses one additional new spacer (i.e., tagging sequence) and one additional repeat which flanks the new spacer at one end of the CRISPR locus (i.e., close to the leader, at the 5' end of the CRISPR locus). All of the other spacers of CRISPR1 locus are unchanged. The CRISPR1 sequence (5'-3') of strain DGCC7710-RH2 is:

(SEQ ID NO: 10)
```
caaggacagttattgattttataatcactatgtgggtataaaaacgtcaaaatttcatttgag GTTTTTGTACTCTCAAGATTTAAGTAACTGTACAACttacgtttgaaaagaatatcaaatcaatga GTTTTTGTACTCTCAAGATTTAAGTAACTGTACAACtgtttgacagcaaatcaagattcgaattgt GTTTTTGTACTCTCAAGATTTAAGTAACTGTACAACaatgacgaggagctattggcacaacttaca GTTTTTGTACTCTCAAGATTTAAGTAACTGTACAACcgatttgacaatctgctgaccactgttatc GTTTTTGTACTCTCAAGATTTAAGTAACTGTACAACacacttggcaggcttattactcaacagcga GTTTTTGTACTCTCAAGATTTAAGTAACTGTACAACctgttccttgttcttttgttgtatcttttc GTTTTTGTACTCTCAAGATTTAAGTAACTGTACAACttcattcttccgttttgtttgcgaatcct GTTTTTGTACTCTCAAGATTTAAGTAACTGTACAACgctggcgaggaaacgaacaaggcctcaaca GTTTTTGTACTCTCAAGATTTAAGTAACTGTACAACcatagagtggaaaactagaaacagattcaa GTTTTTGTACTCTCAAGATTTAAGTAACTGTACAACataatgccgttgaattacacggcaaggtca GTTTTTGTACTCTCAAGATTTAAGTAACTGTACAACgagcgagctcgaaataatcttaattacaag GTTTTTGTACTCTCAAGATTTAAGTAACTGTACAACgttcgctagcgtcatgtggtaacgtattta GTTTTTGTACTCTCAAGATTTAAGTAACTGTACAACggcgtcccaatcctgattaatacttactcg GTTTTTGTACTCTCAAGATTTAAGTAACTGTACAACaacacagcaagacaagaggatgatgctatg GTTTTTGTACTCTCAAGATTTAAGTAACTGTACAACcgacacaagaacgtatgcaagagttcaag GTTTTTGTACTCTCAAGATTTAAGTAACTGTACAACacaattcttcatccggtaactgctcaagtg GTTTTTGTACTCTCAAGATTTAAGTAACTGTACAACaattaagggcatagaaagggagacaacatg GTTTTTGTACTCTCAAGATTTAAGTAACTGTACAACcgatatttaaaatcattttcataacttcat GTTTTTGTACTCTCAAGATTTAAGTAACTGTACAACgcagtatcagcaagcaagctgttagttact GTTTTTGTACTCTCAAGATTTAAGTAACTGTACAACataaactatgaaatttttataattttaaga GTTTTTGTACTCTCAAGATTTAAGTAACTGTACAACataatttatggtatagcttaatatcattg GTTTTTGTACTCTCAAGATTTAAGTAACTGTACAACtgcatcgagcacgttcgagtttaccgtttc GTTTTTGTACTCTCAAGATTTAAGTAACTGTACAACtctatatcgaggtcaactaacaattatgct GTTTTTGTACTCTCAAGATTTAAGTAACTGTACAACaatcgttcaaattctgttttaggtacattt
```

-continued

```
GTTTTTGTACTCTCAAGATTTAAGTAACTGTACAACaatcaatacgacaagagttaaaatggtctt

GTTTTTGTACTCTCAAGATTTAAGTAACTGTACAACgcttagctgtccaatccacgaacgtggatg

GTTTTTGTACTCTCAAGATTTAAGTAACTGTACAACcaaccaacggtaacagctacttttacagt

GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

GTTTTTGTACTCTCAAGATTTAAGTAACTGTACAACaagtagttgatgacctctacaatggtttat

GTTTTTGTACTCTCAAGATTTAAGTAACTGTACAACcctagaagcatttgagcgtatattgattg

GTTTTTGTACTCTCAAGATTTAAGTAACTGTACAACaattttgccccttctttgccccttgactag

GTTTTTGTACTCTCAAGATTTAAGTAACTGTACAACaccattagcaatcatttgtgcccattgagt

GTTTTTGTACTCTCAAGATTTAAGTAACTGTACAGTttgattcaacataaaaagccagttcaattgaacttggcttt
```

The leader sequence is 5'caaggacagttattgatittataatcactatgtgggtataaaaacgtcaaaatttcatttgag3' (SEQ ID NO:6). The integrated sequences comprising CRISPR repeats are shown in upper case, while the CRISPR spacer (i.e., tagging sequence) is shown in lower case. The terminal repeat has the sequence 5' gttmgtactctcaagamaagtaactgtacagt 3' (SEQ ID NO:7), and the trailer sequence has the sequence 5' ttgattcaacataaaaagccagttcaattgaacttggcttt 3' (SEQ ID NO:8). Thus, in the case of S. thermophiles strain DGCC7710-RH2, the spacer (5'-ttacgtttgaaaagaatatcaaatcaatga-3' [SEQ ID NO:11]) constitutes the strain-specific tag which identifies this mutant strain (i.e., tagged bacterium). It was also shown that the sequence of the new spacer exists within D858 phage genome. The sequence of the spacer is located between positions 17215 and 17244 bp (i.e., on the plus strand) of the D858 genome (and has 100% identity to the D858 genomic sequence over 30 nucleotides). The new spacer that is integrated into the CRISPR1 locus of S. thermophiles strain DGCC7710-RH2 confers to resistance to phage D858 to the strain.

In addition to the naturally developed tagged CRISPR loci described above, in some embodiments tagged bacteria are produced using recombinant DNA techniques as known in the art. For example, in some embodiments, synthetic oligonucleotides are produced and inserted into a culture of parent bacteria to produce tagged bacteria. It is also not intended that the present invention be limited to tagged CRISPR loci, as additional loci find use in tagging embodiments.

M. Typing

The present invention also provides methods and compositions for identifying (e.g., typing) a tagged bacterium. In some embodiments, identification involves amplification (e.g., using PCR) the CRISPR locus or a portion thereof. In some embodiments, a first primer is designed to hybridize to a sequence that is located upstream of the first CRISPR repeat of a CRISPR locus. For example, in some embodiments, the first primer hybridizes to part of the common leader sequence of the CRISPR locus. In alternative embodiments, the first primer hybridizes to a neighboring gene that is located upstream of the CRISPR locus. In some embodiments, a second primer hybridizes downstream from the first CRISPR spacer or the first CRISPR spacer core. In some embodiments, the second primer hybridizes in the trailer or even in a downstream neighboring gene. In some preferred embodiments, the second primer hybridizes within the CRISPR locus. In some alternative preferred embodiments, the second primer at least partially hybridizes to a downstream CRISPR spacer or CRISPR spacer core.

In some particularly preferred embodiments, following amplification, the tagging sequence is identified using any suitable method(s) known in the art. For example, in some embodiments, the tagging sequence is identified by determining the amplification product restriction pattern. Accordingly in some embodiments, once the DNA comprising the CRISPR locus or a portion thereof has been amplified, it is digested with one or more restriction enzymes.

In some additional preferred embodiments, the tagging sequences are identified using sequencing methods as known in the art. In still further embodiments, hybridization methods well known in the art find use in the present invention. In some embodiments, methods that encompass hybridization techniques known in the art for the detection and/or differentiation of bacterial strains find use, including but not limited to Southern blotting, shift mobility assays, sequencing assays using oligonucleotide arrays, spoligotyping, fluorescent in situ hybridization (FISH), heteroduplex tracking assays, and heteroduplex mobility analysis.

In some further preferred embodiments, the identified tagging sequence is compared with a sequences in at least one phage sequence database and/or at least one bacterial sequence database. In some embodiments, the tagging sequence matches with one or more sequences in the phage sequence database but not with sequences in the bacterial sequence database. It is contemplated that as new tagged bacteria are prepared using the methods provided herein, additional database(s) of labels will find use in the present invention.

N. Tagged Bacteria

As used herein, the terms "tagged bacteria," "tagged bacterium," "labelled bacteria" and "labelled bacterium" are all used interchangeably in reference to a parent bacterium or parent bacteria, in which one or more CRISPR loci or a portion thereof have been modified (e.g., mutated) in such a way that it is insensitive to the one or more bacteriophage to which it was exposed.

As described in further detail herein, in some embodiments, the tagged bacterium is exposed to more than one bacteriophage (e.g., either iteratively, sequentially or simultaneously), such that it accumulates one or more genomic modifications within one or more CRISPR loci in such a way that it becomes insensitive to each of the bacteriophages to which it has been exposed To infect cells, a bacteriophage injects or transfers its nucleic acid into the cell with the phage nucleic acid existing independently of the cell's genome. In some embodiments, infection results in the expression (i.e., transcription and translation) of the bacteriophage nucleic acid within the cell and continuation of the bacteriophage life cycle.

In some embodiments of the present invention, following exposure to the bacteriophage, the tagged bacterium has a reduced or no susceptibility to bacteriophage infection and/or multiplication when compared to the parent bacterium. As used herein, the term "reduced susceptibility to bacteriophage infection and/or multiplication" means that the level of bacteriophage infection and/or multiplication in the tagged bacterium does not cause a deleterious effect to the tagged bacterium.

Thus, in some embodiments of the present invention, a parent bacterium is not killed following exposure to the bacteriophage, due to mutation of the parent bacterium in such a way that it becomes insensitive to the bacteriophage.

In some embodiments, the tagged bacterium is insensitive or substantially insensitive to further infection and/or multiplication by the bacteriophage. In additional embodiments, the tagged bacterium is insensitive or substantially insensitive to one or more of the mechanisms that the bacteriophage uses to infect and/or multiply in a bacterium. In still further embodiments, the tagged bacterium is insensitive or substantially insensitive to all of the mechanisms that the bacteriophage uses to infect and/or multiply in a bacterium. In yet additional embodiments, the tagged bacterium develops one or more mechanisms that attenuate, inactivate or destroy the bacteriophage during the infection cycle. In some further embodiments, the present invention provides tagged strains selected by standard screening procedures that are known in the art to isolate bacteriophage insensitive mutants.

As indicated above, in addition to the naturally developed tagged CRISPR loci described above, in some embodiments tagged bacteria are produced using recombinant DNA techniques as known in the art. For example, in some embodiments, synthetic oligonucleotides are produced and inserted into a culture of parent bacteria to produce tagged bacteria. It is also not intended that the present invention be limited to tagged CRISPR loci, as additional loci find use in tagging embodiments.

O. Cultures

Cultures, in particular starter cultures, are used extensively in the food industry in the manufacture of fermented products including milk products (e.g., yogurt and cheese), meat products, bakery products, wine, and vegetable products. In particular, starter cultures find widespread use in the manufacture of many fermented milk, cheese and butter products. These bacterial starter cultures impart specific features to various dairy products by performing a number of functions. In some particularly preferred embodiments, the cultures used in the present invention are "industrially useful" cultures. As used herein, this term refers to any bacterial culture that finds use in any industry, including but not limited to the production of food, feed, cosmetics, pharmaceuticals, neutraceuticals, probiotics, enzymes, metabolites, etc. Indeed, it is not intended that the present invention be limited to any particular culture or industry, as the present invention finds use in numerous applications.

Commercial non-concentrated cultures of bacteria are referred to in industry as "mother cultures," and are propagated at the production site (e.g., a dairy), before being added to an edible starting material (e.g., milk), for fermentation. The starter culture propagated at the production site for inoculation into an edible starting material is referred to as the "bulk starter."

Suitable starter cultures for use in the present invention include any organism which is suitable for use in the food, cosmetic and/or pharmaceutical industry. In some preferred embodiments, the starter culture finds use in the dairy industry. Indeed, cultures of lactic acid bacteria are commonly used in the manufacture of fermented milk products (e.g., buttermilk, yogurt and sour cream), and in the manufacture of butter and cheese (e.g., brie, havarti, cheddar, Monterey jack, etc.).

As used herein the term "lactic acid bacteria" refers to Gram positive, microaerophillic or anaerobic bacteria which ferment sugar with the production of acids, including lactic acid as the predominantly produced acid, acetic acid, formic acid and propionic acid. The industrially most useful lactic acid bacteria include *Lactococcus* (e.g., *Lactococcus lactis*), *Lactobacillus*, *Bifidobacterium*, *Streptococcus*, *Leuconostoc*, *Pediococcus*, and *Propionibacterium* species. In some embodiments, the present invention provides starter cultures comprising at least one lactic acid bacteria species such as, *L. lactis*, *Lactobacillus delbrueckii* subsp. *bulgaricus* and *Streptococcus thermophilus* or combinations thereof. Lactic acid bacteria starter cultures are commonly used in the food industry as mixed strain cultures comprising one or more species. In some embodiments comprising mixed strain cultures (e.g., yogurt starter cultures) comprising strains of *Lactobacillus delbrueckii* subsp. *bulgaricus* and *Streptococcus thermophilus*, a symbiotic relationship exists between the species wherein the production of lactic acid is greater compared to cultures of single strain lactic acid bacteria (See e.g., Rajagopal et al., J. Dairy Sci., 73:894-899 [1990]).

In some particularly preferred embodiments, the starter culture is a lactic acid bacteria species, including but not limited to strains of *Bifidobacterium*, *Brevibacterium*, or *Propionibacterium*. Suitable starter cultures of the lactic acid bacteria group include, but are not limited to commonly used strains *Lactococcus*, *Streptococcus*, *Lactobacillus* (e.g., *Lactobacillus acidophilus*), *Enterococcus*, *Pediococcus*, *Leuconostoc*, and *Oenococcus*. *Lactococcus* species include, but are not limited to the widely used *Lactococcus lactis*, including *Lactococcus lactis* subsp. *lactis* and *Lactococcus lactis* subsp. *cremoris*, and *Lactococcus lactis* subsp. *lactis biovar*. Other lactic acid bacteria species include *Leuconostoc*, *Streptococcus thermophilus*, *Lactobacillus delbrueckii* subsp. *bulgaricus* and *Lactobacillus helveticus*. In addition, probiotic strains such as *Bifidobacterium lactis*, *Lactobacillus acidophilus*, *Lactobacillus casei* find use in flavor enhancement and provide health benefits. Thermophilic cultures of lactic acid bacteria commonly used in the manufacture of Italian cheeses such as Pasta filata or parmesan, include *S. thermophilus* and *L. delbrueckii* subsp *bulgaricus*. In some embodiments, other *Lactobacillus* species (e.g., *L. helveticus*) are added during manufacturing to obtain a desired flavor.

In some embodiments, the starter culture comprises or consists of a genetically modified strain (prepared according to the methods desired herein) of one of the above lactic acid bacteria strains or any other suitable starter culture strain. As known to those skilled in the art, the selection of organisms for the starter cultures used in the present invention depends on the particular type of products to be prepared and treated. Thus, for example, for cheese and butter manufacturing, mesophillic cultures of *Lactococcus* species, *Leuconostoc* species and *Lactobacillus* species find wide use, whereas thermophillic strains of *Streptococcus* species and of *Lactobacillus* species find wide use for yogurt and other fermented milk products.

In some embodiments, the starter culture is a dried starter, while in other embodiments, it is a concentrated starter, and in other embodiments, it is a frozen culture. In some preferred embodiments, the dried starter cultures comprise at least one lactic acid bacteria. In some embodiments, the starter culture is used for direct inoculation. In some preferred embodiments, the culture is a concentrated starter culture used for direct inoculation.

In some embodiments, the bacterial starter culture comprises one bacterial strain or species (i.e., it is a pure culture). Thus, in these embodiments, substantially all, or at least a significant portion of the bacterial starter culture comprises the same bacterial strain or species. However, in some alternative embodiments, the starter culture comprises more than one or several bacterial strains or species (i.e., it is a mixed culture, such as a defined mixed Starter cultures prepared using any suitable technique known in the art find use in the present invention (See e.g., U.S. Pat. No. 4,621,058). For example, starter cultures prepared by the introduction of an inoculum (e.g., a bacterial culture) to a growth medium, to produce an inoculated medium and incubating the inoculated medium to produce a starter culture. However, it is not intended that the present invention be limited to any particular method for preparing starter cultures.

Dried starter cultures prepared using any suitable technique known in the art find use in the present invention (See e.g., U.S. Pat. Nos. 4,423,079 and 4,140,800). In some embodiments, the dried starter cultures used in the present invention are solid preparations (e.g., tablets, pellets, capsules, dusts, granules and powders, any of which are wettable, spray-dried, freeze-dried or lyophilized in some embodiments). In some alternative embodiments, the dried starter cultures of the present invention are either a deep frozen pellet or freeze-dried powder. These dried starter cultures are prepared using any suitable method known in the art.

In some embodiments, the starter cultures used in the present invention comprise concentrates having substantially high concentrations of at least one bacterial species. In some preferred embodiments, the concentrates are diluted with water or resuspended in water or another suitable diluent (e.g., an appropriate growth medium, mineral oil, or vegetable oil), for use in the present invention. In some embodiments, the concentrated dried starter cultures of the present invention are prepared using methods well known in the art, including, but not limited to centrifugation, filtration or a combination of such techniques.

P. Products

The present invention finds use in the production of various products, including but not limited to food, feed, cosmetic products, and/or pharmaceutical products. Indeed, it is contemplated that any product prepared from or comprises a bacterial culture finds use in the present invention. These include, but are not limited to, fruits, legumes, fodder crops and vegetables including derived products, grain and grain-derived products, dairy foods and dairy-derived products, meat, poultry, seafood, cosmetics, enzymes, metabolites, and pharmaceutical products.

As used herein, the term "food" is used in a broad sense and includes feed, foodstuffs, food ingredients, food supplements, and functional foods. Although the term includes food for humans, it is intended that the term also encompass food for non-human animals (i.e., "feed"). However, in some preferred embodiments, the present invention provides food for human consumption. As used herein, the term "food ingredient" includes a formulation suitable for addition to foods. In some embodiments, the formulations are used at low levels in a wide variety of products that require, for example, acidifying or emulsifying. As used herein, the term "functional food" refers to foods that are capable of providing not only a nutritional effect and/or a taste satisfaction, but are also capable of delivering a further beneficial effect to consumer. In some embodiments the bacteria of the present invention comprise or are added to a food ingredient, supplement or functional food. It is contemplated that the food be provided in any suitable form, including but not limited to solutions, solids, gels, emulsions, etc., depending on the use and/or the mode of application and/or the mode of administration. Indeed, it is not intended that the present invention be limited to food in any particular form. In some embodiments, the bacteria of the present invention find use in the numerous preparation of food products, including but not limited to confectionery products, dairy products, meat products, poultry products, fish products, and bakery products. In some embodiments, the bacteria are used as ingredients in soft drinks, fruit juices, beverages comprising whey protein, health teas, cocoa drinks, milk drinks, lactic acid bacteria drinks, cheese, yogurt, drinking yogurt and wine. In some further embodiments, the present invention provides methods of preparing food, including methods that comprise admixing bacteria according to the present invention with a food ingredient (e.g., a starting material for a food). In some preferred embodiments, the food provided herein is a dairy product. In some particularly preferred embodiments, the dairy product is selected from yogurt, cheese (e.g., an acid curd cheese, a hard cheese, a semi-hard cheese, a cottage cheese), a buttermilk, quark, a sour cream, kefir, a fermented whey-based beverage, a koumiss, a milk drink and a yogurt drink.

As used herein, the terms "food" and "feed" include, but are not limited to raw and processed plant material, as well as non-plant material. It is intended that the food/feed be suitable for consumption by any animal, human or non-human. In some preferred embodiments, the food/feed find use with livestock (e.g., cattle, sheep, pigs, etc.), poultry (e.g., chickens and turkeys), fish, reptiles, or crustaceans. Indeed, it is not intended that the present invention be limited to food/feed for any particular organism.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); $H_2O$ (water); aa (amino acid); bp (base pair); kb (kilobase pair); kD (kilodaltons); g and gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); sec and s (seconds); min(s) (minute/minutes); hr(s) (hour/hours); MOI (multiplicity of infection); EOP (efficiency of plaquing); PFU (plaque-forming units); MgCl₂ (magnesium chloride); NaCl (sodium chloride); PAGE (polyacrylamide gel electrophoresis); PBS (phosphate buffered saline [150 mM NaCl, 10 mM sodium phosphate buffer, pH 7.2]); SDS (sodium dodecyl sulfate); Tris (tris(hydroxymethyl)aminomethane); w/v (weight to volume); v/v (volume to volume); Promega (Promega, Inc., Madison, Wis.); ATCC (American Type Culture Collection, Manassas, Va.); Difco (Difco Laboratories, Detroit, Mich.); GIBCO BRL or Gibco BRL (Life Technologies, Inc., Gaithersburg, Md.); and Sigma (Sigma Chemical Co., St. Louis, Mo.).

The present invention utilizes, unless otherwise indicated, conventional techniques of chemistry, molecular biology, microbiology, recombinant DNA and immunology, which are within the capabilities of a person of ordinary skill in the art. Such techniques are well known to those of skill in the art.

As used herein, DGCC7710 is also referred to as "WT"; DGCC7710RH1 is also referred to as "DGCC7710-RH1" and "RH1"; DGCC7710RH2 is also referred to as "DGCC7710-RH2" and "RH-2."

Example 1

Tagging of *Streptococcus thermophilus* DGCC7710 Using Bacteriophage D2972 by the Insertion of a Single Repeat-Spacer Unit Within CRISPR1

In this example, *S. thermophilus* strain DGCC7710 (deposited at the French "Collection Nationale de Cultures de Microorganismes" numbered CNCM 1-2423) was tagged by "natural" insertion within its CRISPR1 locus of an additional repeat-spacer unit with the spacer originating from bacteriophage D2972. The DGCC7710 CRISPR1 locus contains 33 repeats (including the terminal repeat) and 32 spacers (See, GenBank Accession Number: EF434469). Bacteriophage D2972 was isolated from a fermented dairy product using strain DGCC7710. Its genome has been fully sequenced (See, GenBank Accession Number: AY699705). The sequence of the DGCC7710 CRISPR1 locus is:

```
                                                                 (SEQ ID NO: 1)
           caaggacagttattgattttataatcactatgtgggtataaaaacgtcaaaatttcatttgag GTTTTTGTACTCTCAAGATTTAAGTAACTGTACAACtgtttgacagcaaatcaagattcgaattgt GTTTTTGTACTCTCAAGATTTAAGTAACTGTACAACaatgacgaggagctattggcacaacttaca GTTTTTGTACTCTCAAGATTTAAGTAACTGTACAACcgatttgacaatctgctgaccactgttatc GTTTTTGTACTCTCAAGATTTAAGTAACTGTACAACacacttggcaggcttattactcaacagcga GTTTTTGTACTCTCAAGATTTAAGTAACTGTACAACctgttccttgttcttttgttgtatcttttc GTTTTTGTACTCTCAAGATTTAAGTAACTGTACAACttcattcttccgttttttgtttgcgaatcct GTTTTTGTACTCTCAAGATTTAAGTAACTGTACAACgctggcgaggaaacgaacaaggcctcaaca GTTTTTGTACTCTCAAGATTTAAGTAACTGTACAACcatagagtggaaaactagaaacagattcaa GTTTTTGTACTCTCAAGATTTAAGTAACTGTACAACataatgccgttgaattacacggcaaggtca GTTTTTGTACTCTCAAGATTTAAGTAACTGTACAACgagcgagctcgaaataatcttaattacaag GTTTTTGTACTCTCAAGATTTAAGTAACTGTACAACgttcgctagcgtcatgtggtaacgtattta GTTTTTGTACTCTCAAGATTTAAGTAACTGTACAACggcgtcccaatcctgattaatacttactcg GTTTTTGTACTCTCAAGATTTAAGTAACTGTACAACaacacagcaagacaagaggatgatgctatg GTTTTTGTACTCTCAAGATTTAAGTAACTGTACAACcgacacaagaacgtatgcaagagttcaag GTTTTTGTACTCTCAAGATTTAAGTAACTGTACAACacaattcttcatccggtaactgctcaagtg GTTTTTGTACTCTCAAGATTTAAGTAACTGTACAACaattaagggcatagaaagggagacaacatg GTTTTTGTACTCTCAAGATTTAAGTAACTGTACAACcgatatttaaaatcattttcataacttcat GTTTTTGTACTCTCAAGATTTAAGTAACTGTACAACgcagtatcagcaagcaagctgttagttact GTTTTTGTACTCTCAAGATTTAAGTAACTGTACAACataaactatgaaattttataattttttaaga GTTTTTGTACTCTCAAGATTTAAGTAACTGTACAACaataatttatggtatagcttaatatcattg GTTTTTGTACTCTCAAGATTTAAGTAACTGTACAACtgcatcgagcacgttcgagtttaccgtttc GTTTTTGTACTCTCAAGATTTAAGTAACTGTACAACtctatatcgaggtcaactaacaattatgct GTTTTTGTACTCTCAAGATTTAAGTAACTGTACAACaatcgttcaaattctgttttaggtacattt GTTTTTGTACTCTCAAGATTTAAGTAACTGTACAACaatcaatacgacaagagttaaaatggtctt GTTTTTGTACTCTCAAGATTTAAGTAACTGTACAACgcttagctgtccaatccacgaacgtggatg GTTTTTGTACTCTCAAGATTTAAGTAACTGTACAACcaaccaacggtaacagctactttttacagt
```

-continued

```
GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

GTTTTTGTACTCTCAAGATTTAAGTAACTGTACAACaagtagttgatgacctctacaatggtttat

GTTTTTGTACTCTCAAGATTTAAGTAACTGTACAACacctagaagcatttgagcgtatattgattg

GTTTTTGTACTCTCAAGATTTAAGTAACTGTACAACaattttgcccctttctttgcccttgactag

GTTTTTGTACTCTCAAGATTTAAGTAACTGTACAACaccattagcaatcatttgtgcccattgagt

GTTTTTGTACTCTCAAGATTTAAGTAACTGTACAGTttgattcaacataaaaagccagttcaattg aacttggcttt
```

In the first step the parental strain (DGCC7710) was exposed to the donor bacteriophage (D2972). DGCC7710 was pre-cultivated in sterile milk-based medium (10% w/v of milk powder in water, sterilized for 20 min at 110° C.) at 42° C. for 6 hours. The pre-culture was used to inoculate 10 ml of sterile milk-based medium at about 0.05% (w/v). About $10^7$ bacteriophages D2972 were added to the inoculated milk-based medium (final bacteriophage count of about $10^6$ pfu/ml). The mixture was then cultivated at 42° C. for 16 hours. Following incubation, dilutions of the culture are plated on M17-glucose (0.5% w/v) medium in order to obtain isolated colonies after incubation at 42° C. for 24 hours. A number of colonies were picked and grown separately in sterile milk-based medium at 42° C. for 18 hours to provide a stock of isolates.

Figure 3:
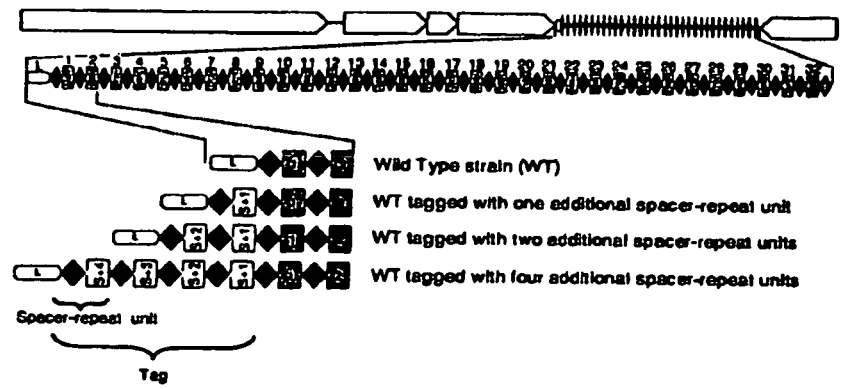
FIG. 3 provides a schematic representation of the CRISPR1 locus of *S. thermophilus* DGCC7710 and tagged variants. The CRISPR1 locus of DGCC7710(WT) is at the top. In this Figure, arrowed boxes represent genes in the vicinity of CRISPR1. The spacer-repeat region of WT is in the middle, with repeats (black diamonds), spacers (numbered gray boxes), leader (L, white box), and terminal repeat (T, black diamond) indicated. At the bottom, tagged variants are represented with 1, 2 or 4 added repeat-spacer units (black diamonds associated with S+n white box). The combination of the added repeat-spacer units represents the tag. In this Figure, the new numbering system of the cas genes is used. Previously, the cas genes were numbered cas 1, cas2, cas3, and cas4. Now, the cas genes are numbered cas5, cas1, cas6, and cas7. Thus, to correlate the designations in FIGS. 1 and 2, with those in FIGS. 3 and 4, cas1 in FIGS. 1 and 2 is referred to as cas5 in FIGS. 3 and 4; cas2 in FIGS. 1 and 2 is cas1 in FIGS. 3 and 4; cas3 in FIGS. 1 and 2 is cas6 in FIGS. 3 and 4; and cas4 in FIGS. 1 and 2 is cas7 in FIGS. 3 and 4.

Then, each tagged strain was identified through sequence analysis of their CRISPR1 loci. In this Example, a tagged strain is a variant of the parental strain, in which the variant contains an additional repeat-spacer unit within the CRISPR1 locus (See, FIG. 3). Typically, the spacer part of the additional unit is of approximately 30 nucleotides in size and its sequence is identical to a subsequence of the donor phage. Isolates were cultivated separately at 42° C. for 18 hours in M17-glucose medium. Cells were harvested and their DNA extracted. For each isolate, the region of the chromosome corresponding to the leader end of the CRISPR1 locus was amplified by PCR using the following primers: forward primer yc70 (5'-tgctgagacaacctagtctctc-3' [SEQ ID NO:15]; See, Bolotin et al., Microbiol., 151:2551-2561 [2005]); and reverse primer CR1-89R5 (5'-acaaaaacg-gaagaatgaagttg-3' [SEQ ID NO:16]). The PCR reaction mix (final volume of 25 µL) contained: Mg-free buffer 1× (Promega), $MgCl_2$ 2.5 mM, each of the four dNTP 2 mM, DNA 10 to 100 ng, each primer 0.2 µM, Taq polymerase 1.25 U (Promega). PCR cycling conditions were as following: pre-denaturation at 98° C. for 5 min, then 33 cycles alternating denaturation at 94° C. for 30 s, hybridization at 56° C. for 30 s, and elongation at 72° C. for 1 min; followed by a final elongation step at 72° C. for 4 min. The nucleic sequence of each PCR fragment was then determined using the "forward primer" and classical sequencing methodology, as known in the art. Each sequence was compared to that obtained for the parental strain to identify the presence of additional sequence.

Through independent experiments, multiple tagged strains were created from DGGC7710 using D2972 as a donor. Some of these tagged strains are described in Table 1-1. They all differ from the parental strain by a single additional repeat-spacer unit at the leader end of the CRISPR1 locus. In all cases, the spacer part of the additional unit is 100% identical to a sub-sequence of the donor bacteriophage D2972 (this sub-sequence of the donor bacteriophage is also referred to as a "pro-spacer"). Typically, the tagged strains described in this Example possess a CRISPR1 locus made of 34 repeats and 33 spacers; 32 spacers originate from the DGCC7710, the supplementary spacer originates from D2972.

TABLE 1-1

Description of Strains Tagged in CRISPR1 Locus
Derived From DGCC7710 Using D2972 as a Donor

| Tagged Strain | Parental Strain | Donor Phage | Inserted donor DNA Sequence | Location* |
|---|---|---|---|---|
| DGCC7710$_{phi2972}$$^{+S40}$ | DGCC7710 | D2972 | TCTGGAAAGCATATTGAGGGA GCTACTCTT (SEQ ID NO: 17) | 27974-28003 (+) |
| DGCC7710$_{phi2972}$$^{+S41}$ | DGCC7710 | D2972 | TCTAATCCCACTAGGAATAGT GGGTAGTAA (SEQ ID NO: 18) | 25693-25722 (+) |
| DGCC7710$_{phi2972}$$^{+S43}$ | DGCC7710 | D2972 | TTATAACATAACGGTTAGTTG GCCTCTAT (SEQ ID NO: 19) | 23410-23382 (−) |
| DGCC7710$_{phi2972}$$^{+S44}$ | DGCC7710 | D2972 | AAGGAGCTAGCCACATTTCCG CAATTGATA (SEQ ID NO: 20) | 23334-23363 (+) |
| DGCC7710$_{phi2972}$$^{+S45}$ | DGCC7710 | D2972 | CAGCTTGAAATGTTTATTGAA GCAGCAGTG (SEQ ID NO: 21) | 24624-24653 (+) |

TABLE 1-1-continued

Description of Strains Tagged in CRISPR1 Locus
Derived From DGCC7710 Using D2972 as a Donor

| Tagged Strain | Parental Strain | Donor Phage | Inserted donor DNA Sequence | Location* |
|---|---|---|---|---|
| DGCC7710$_{phi2972}$$^{+S46}$ | DGCC7710 | D2972 | AAATCAGTTTTTTGTTCAGAA ACTTGTTCT (SEQ ID NO: 22) | 25582-25611 (+) |

*(+/−): indicates the strand of the phage chromosome

Example 2

Tagging of Streptococcus thermophilus DGCC7710 Using Bacteriophage D858 by the Insertion of a Single Repeat-Spacer Unit Within CRISPR1

In this Example, S. thermophilus strain DGCC7710 was tagged by "natural" insertion within its CRISPR1 locus with an additional repeat-spacer unit wherein the spacer originated from bacteriophage D858. Bacteriophage D858 is was isolated from a fermented dairy product in strain DGCC7710. D858 is a bacteriophage belonging to the Siphoviridae family of viruses. Its genome sequence has been completely determined (GenBank Accession. Number: EF529515). This phage is virulent to S. thermophilus strain DGCC7710.
Its genome has been fully sequenced First, the parental strain (DGCC7710) was exposed to the donor bacteriophage (D858). DGCC7710 was pre-cultivated in sterile milk-based medium (10% w/v of milk powder in water, sterilized 20 min at 110° C.) at 42° C. for 6 hours. The pre-culture was used to inoculate 10 ml of sterile milk-based medium at about 0.05% (w/v). About $10^7$ D858 bacteriophages were added to the inoculated milk-based medium (final bacteriophage count of about $10^6$ pfu/ml). The mixture was then cultivated at 42° C. for 16 hours. Following incubation, dilutions of the culture were plated on M17-glucose (0.5% w/v) medium in order to obtain isolated colonies after incubation at 42° C. for 24 hours. A number of colonies were picked and grown separately in sterile milk-based medium at 42° C. for 18 hours to provide a stock of isolates.

Then, each tagged strain was identified through sequence analysis of their CRISPR1 locus. In this Example, a tagged strain is a variant of the parental strain that contains an additional repeat-spacer unit within its CRISPR1 locus (See, FIG. 3). Typically, the spacer part of the additional unit was approximately 30 nucleotides in size and its sequence was identical to a sub-sequence of the donor phage. Isolates were cultivated separately at 42° C. for 18 hours in M 17-glucose medium. Cells were harvested and their DNA extracted. For each isolate, the region of the chromosome corresponding to the leader end of the CRISPR1 locus was amplified by PCR using the following primers: forward primer yc70 (5'-tgct-gagacaacctagtctctc-3' [SEQ ID NO:15], Bolotin et al., [2005], supra); and reverse primer CR1-89R5 (5'-acaaaaacg-gaagaatgaagttg-3' [SEQ ID NO:20]). The PCR reaction mix (final volume of 25 μL) contained: Mg-free buffer 1× (Promega), MgCl$_2$ 2.5 mM, each of the four dNTP 2 mM, DNA 10 to 100 ng, each primer 0.2 μM, Taq polymerase 1.25 U (Promega). PCR cycling conditions were as following: pre-denaturation at 98° C. for 5 min, then 33 cycles alternating denaturation at 94° C. for 30 s, hybridisation at 56° C. for 30 s, and elongation at 72° C. for 1 min; followed by a final elongation step at 72° C. for 4 min. The nucleic sequence of each PCR fragment was then determined using the "forward primer" and classical sequencing methodology as known in the art. Each sequence was compared to that obtained for the parental strain to identify the presence of additional sequence.

One tagged strain created from DGCC7710 using D858 as a donor is described in Table 2-1. It differs from the parental strain by a single additional repeat-spacer unit at the leader end of the CRISPR1 locus. The spacer part of the additional unit is 100% identical to a sub-sequence of the donor bacteriophage D858.

TABLE 2-1

Description of Strains Tagged in CRISPR1 Locus,
Derived From DGCC7710 and Using D858 as a Donor

| Tagged Strain | Parental Strain | Donor Phage | Inserted Donor DNA Sequence | Location* |
|---|---|---|---|---|
| DGCC7710$_{phi858}$$^{+S42}$ | DGCC7710 | D858 | TCGATAAATCAGCCAAAGTATT AAGTGGTT (SEQ ID NO: 23) | 27560-27589 (+) |

*(+/−): indicates the strand of the phage chromosome

Example 3

Tagging of Streptococcus thermophilus DGCC7710 Using Bacteriophage D2972 by the Insertion of Multiple Repeat-Spacer Units Within CRISPR1

In this Example, S. thermophilus strain DGCC7710 was tagged by "natural" insertion within its CRISPR1 locus by the addition of multiple repeat-spacer units with the spacers originating from bacteriophage D2972.

First, the parental strain (DGCC7710) was exposed to the donor bacteriophage (D2972). DGCC7710 was pre-cultivated in sterile milk-based medium (10% w/v of milk powder in water, sterilized 20 min at 110° C.) at 42° C. for 6 hours. The pre-culture was used to inoculate 10 ml of sterile milk-based medium at about 0.05% (w/v). About 10⁷ D2972 bacteriophages were added to the inoculated milk-based medium (final bacteriophage count of about 10⁶ pfu/ml). The mixture was then cultivated at 42° C. for 16 hours. Following incubation, dilutions of the culture were plated on M17-glucose (0.5% w/v) medium in order to obtain isolated colonies after incubation at 42° C. for 24 hours. A number of colonies were picked and grown separately in sterile milk-based medium at 42° C. for 18 hours to provide a stock of isolates.

Then, each tagged strain was identified through sequence analysis of its CRISPR1 locus. In this Example, a tagged strain is a variant of the parental strain that contains multiple additional repeat-spacer units within its CRISPR1 locus (See, FIG. 3). Typically, the spacer part of each additional unit was approximately 30 nucleotides in size and its sequence was identical to a sub-sequence of the donor phage. Isolates were cultivated separately at 42° C. for 18 hours in M17-glucose medium. Cells were harvested and their DNA extracted. For each isolate, the region of the chromosome corresponding to the leader end of the CRISPR1 locus is amplified by PCR using the following primers: forward primer yc70 (5'-tgctgagacaacctagictctc-3' [SEQ ID NO:15], Bolotin et al., 2005, supra); reverse primer CR1-89R5 (5'-acaaaaacggaagaatgaagttg-3' [SEQ ID NO:16]). The PCR reaction mix (final volume of 25 μL) contained: Mg-free buffer 1× (Promega), MgCl₂ 2.5 mM, each of the four dNTP 2 mM, DNA 10 to 100 ng, each primer 0.2 μM, Taq polymerase 1.25 U (Promega). PCR cycling conditions were as following: pre-denaturation at 98° C. for 5 min, then 33 cycles alternating denaturation at 94° C. for 30 s, hybridization at 56° C. for 30 s, and elongation at 72° C. for 1 min; followed by a final elongation step at 72° C. for 4 min. The nucleic sequence of each PCR fragment was then determined using the "forward primer" and classical sequencing methodology as known in the art. Each sequence was compared to that obtained for the parental strain to identify the presence of additional sequence.

Through independent experiments, multiple tagged strains were created from DGCC7710 using D2972 as a donor. Some of these tagged strains are described in Table 3-1. They all differ from the parental strain by multiple additional repeat-spacer units at the leader end of the CRISPR1 locus. In all cases, the spacer part of each additional unit is 100% identical to a subsequence of the donor bacteriophage D2972.

TABLE 3-1

Description of Tagged Strains in CRISPR1 Locus
From DGCC7710 Using D2972 as a Donor

| Tagged Strain | Parental Strain | Donor Phage | Inserted Donor DNA Sequence | Location |
|---|---|---|---|---|
| DGCC7710$_{phi2972}^{+S46+S47}$ | DGCC7710 | D2972 | AAATCAGTTTTTTGTTCAGAAACTTG TTCT (SEQ ID NO: 24) TTGTCTATTACGACAACATGGAAGA TGAT (SEQ ID NO: 25) | 33045-33073 (+) 25582-25611 (+) |
| DGCC7710$_{phi2972}^{+S48+S49}$ | DGCC7710 | D2972 | TTTTGAGAAAGTCTTTAACGATGCA GTAGC (SEQ ID NO: 26) TAATAGTTTACCAAATCATCTTTATT CCAA (SEQ ID NO: 27) | 25967-25938 (−) 6008-6037 (+) |
| DGCC7710$_{phi2972}^{+S50+S51}$ | DGCC7710 | D2972 | GAAGTTGAAATAATTCGAGAAATAG AACTC (SEQ ID NO: 28) TGGAAACCAAGAAATGCAATAGAAT GGAAG (SEQ ID NO: 29) | 34105-34134 (+) 29246-29275 (+) |
| DGCC7710$_{phi2972}^{+S52+S4}$ | DGCC7710 | D2972 | CTGATTGTTAATGTACGAGGGCTCC AGCCA (SEQ ID NO: 30) CTCAGTCGTTACTGGTGAACCAGTTT CAAT (SEQ ID NO: 31) | 31582-31611 (+) 21732-21703 (−) |
| DGCC7710$_{phi2972}^{+S53+S54}$ | DGCC7710 | D2972 | TGTTTCAAGGTTTCGGGTCCAAGTAT CATT (SEQ ID NO: 32) TTTTCCGTCTTCTTTTTTAGCAAAGA TACG (SEQ ID NO: 33) | 29647-29618 (−) 16681-16652 (−) |
| DGCC7710$_{phi2972}^{+S61+S62}$ | DGCC7710 | D2972 | GATTCGTGGCGATATTCGTCTTACGT TTGA (SEQ ID NO: 34) ACATATCGACGTATCGTGATTATCCC ATT (SEQ ID NO: 35) | 31709-31737 (+) 17182-17211 (+) |
| DGCC7710$_{phi2972}^{+S55+S63+S41}$ | DGCC7710 | D2972 | CTGGAAAGCATATTGAGGGAGCTAC TCTT (SEQ ID NO: 36) GTATATCGAAGAACGACTGAAAGAG CTTGA (SEQ ID NO: 37) TCTAATCCCACTAGGAATAGTGGGT AGTAA (SEQ ID NO: 38) | 25693-25722 (+) 1114-1142 (+) 27381-27409 (+) |

*(+/−): indicates the strand of the phage chromosome

Example 4

Tagging of *Streptococcus thermophilus* DGCC7710 Using Bacteriophage D2972 by the Iterative Insertion of Repeat-Spacer Units Within CRISPR1

In this Example, *S. thermophilus* strain DGCC7710 was tagged by "natural" means through iterative insertion within its CRISPR1 locus of additional repeat-spacer units with the spacers originating from bacteriophage D2972 and from bacteriophages derived from D2972.

In the first iteration, the parental strain (DGCC7710) was exposed to the donor bacteriophage (D2972) and a tagged strain was isolated and characterized by using the same methodology as described in Example 1. Compared to DGCC7710, this tagged strain (named DGCC7710$_{phi2972}^{S6}$) possessed an additional repeat-spacer unit as described in Table 4 in its CRISPR1 locus Because of the insertion of an additional repeat-spacer unit in the CRISPR1 locus of strain DGCC7710$_{phi2972}^{S6}$, the donor bacteriophage D2972 was no longer virulent against DGCC7710$_{phi2972}^{S6}$, and cannot be used as a donor bacteriophage for this strain. This problem was overcome by the use of a mutated donor phage derived from D2972 that includes at least one specific modification within its genome (i.e., a "mutated phage"). This mutated phage was selected by exposing the donor bacteriophage to the tagged strain, such that a modification (i.e., mutation) of the parental phage renders it virulent for the tagged strain.

Next, strain DGCC7710$_{phi2972}^{S6}$ was exposed to the donor bacteriophage D4724 and a tagged strain was isolated and characterized using the methodology described in Example 1. Compared to DGCC7710 this tagged strain (named DGCC7710$_{phi2972}^{S6}$$_{phi4724}^{S15}$) possesses in its CRISPR1 locus 2 additional repeat-spacer units as described in Table 4-1.

For the purpose of a third iteration, a second mutated bacteriophage named D4733 was selected through challenging of DGCC7710$_{phi2972}^{S6}$$_{phi4724}^{S15}$ by D4724 using the same methodology as for obtaining D4724. Bacteriophage D4733 is virulent against DGCC7710$_{phi2972}^{S6}$$_{phi4724}^{S15}$. Upon exposure of virulent for DGCC7710$_{phi2972}^{S6}$$_{phi4724}^{S15}$ to the donor bacteriophage D4733, a tagged strain was isolated and characterized using the same methodology as described in Example 1. Compared to DGCC7710, this tagged strain, named DGCC7710$_{phi2972}^{S6}$$_{phi4724}^{S15}$$_{phi4733}^{S29}$, possessed 3 additional repeat-spacer units in its CRISPR1 locus as described in Table 4-1.

TABLE 4-1

Description of Iteratively Tagged Strains in CRISPR1 Locus from DGCC7710 Using D2972 and Mutated Phages D4724 and D4733 as Donor Bacteriophages

| Tagged Strain | Parental Strain | Donor Phage | Inserted Donor DNA Sequence | Location |
|---|---|---|---|---|
| DGCC7710$_{phi2972}^{+S6}$ | DGCC7710 | D2972 | GCCCTTCTAATTGGA TTACCTTCCGAGGTG (SEQ ID NO: 39) | 34521-34492 (−) |
| DGCC7710$_{phi2972}^{+S56}$$_{phi4724}^{+S20}$ | DGCC7710$_{phi2972}^{+S6}$ | D4724 | GCCCTTCTAATTGGA TTACCTTCCGAGGTG (SEQ ID NO: 40) TTATATCGAAGAACG ACTGAAAGAGCTTGA (SEQ ID NO: 41) | 34521-34492 (−) 1113-1142 (+) |
| DGCC7710$_{phi2972}^{+S6}$$_{phi4724}^{+S20}$$_{phi4733}^{+S29}$ | DGCC7710$_{phi2972}^{+S6}$$_{phi4724}^{+S20}$ | D4733 | GCCCTTCTAATTGGA TTACCTTCCGAGGTG (SEQ ID NO: 42) TTATATCGAAGAACG ACTGAAAGAGCTTGA (SEQ ID NO: 43) ATTGGCATGATTTCAA TTTTAATTGGGAT (SEQ ID NO: 44) | 34521-34492 (−) 1113-1142 (+) 32136-32164 (+) |

*(+/−): indicates the strand of the phage chromosome

DGCC7710$_{phi2972}^{S6}$ was pre-cultivated in milk-based medium at 42° C. for 18 hours. A milk-based medium was then inoculated with the pre-culture of DGCC7710$_{phi2972}^{S6}$ at a concentration of about 10$^6$ cfu/ml and with a suspension of D2972 at an MOI (multiplicity of infection) greater than 100. The culture was incubated at 42° C. for 18 hours, and then centrifuged for 10 min at 10,000×g. The supernatant was harvested and filtered using a 0.45 µm filter. Appropriate dilutions of the filtrated supernatant were used to inoculate a M17-glucose agar media seeded with a lawn of DGCC7710$_{phi2972}^{S6}$ using methods well known in the art. The seeded agar plates were incubated for 24 hours at 42° C. One isolated plaque was picked and cultivated on DGCC7710$_{phi2972}^{S6}$ in M17- glucose medium for 6 hours at 42° C. A suspension of this new bacteriophage named D4724 was obtained by filtering the culture through a 0.45 µm filter. The virulence of D4724 against DGCC7710$_{phi2972}^{S6}$ was verified.

Example 5

Tagging of *Streptococcus thermophilus* DGCC3198 Using Bacteriophage D4241 by the Insertion of a Single Repeat-Spacer Unit within CRISPR1

In this Example, *S. thermophilus* strain DGCC3198 (also known as LMD-9 and deposited at the American Type Culture Collection as ATCC BAA-365) was tagged by "natural" insertion within its CRISPR1 locus of an additional repeat-spacer unit with the spacer originating from bacteriophage D4241. The DGCC3198 CRISPR1 locus contains 17 repeats (including the terminal repeat) and 16 spacers (GenBank Accession Number: CP000419). Bacteriophage D4241 was isolated from a fermented dairy product using strain DGCC3198. The sequence of the DGCC3198 CRISPR1 locus is:

(SEQ ID NO: 45)
```
caagaacagttattgattttataatcactatgtgggtatgaaaatctcaaaaatcatttgag GTTTTTGTACTCTCAAGATTTAAGTAACTGTACAACatgatgatgaagtatcgtcatctactaac GTTTTTGTACTCTCAAGATTTAAGTAACTGTACAACcttcacctcaaatcttagagctggactaaa GTTTTTGTACTCTCAAGATTTAAGTAACTGTACAACatgtctgaaaaataaccgaccatcattact GTTTTTGTACTCTCAAGATTTAAGTAACTGTACAACgaagctcatcatgttaaggctaaaacctat GTTTTTGTACTCTCAAGATTTAAGTAACTGTACAACtagtctaaatagatttcttgcaccattgta GTTTTTGTACTCTCAAGATTTAAGTAACTGTACAACattcgtgaaaaatatcgtgaaataggcaa GTTTTTGTACTCTCAAGATTTAAGTAACTGTACAACtctaggctcatctaaagataaatcagtagc GTTTTTGTACTCTCAAGATTTAAGTAACTGTACAACtaaaaacatggggcggcggtaatagtgtaag GTTTTTGTACTCTCAAGATTTAAGTAACTGTACAACacaaccagcaaagagagcgccgacaacatt GTTTTTGTACTCTCAAGATTTAAGTAACTGTACAACtataacacaggtttagaggatgttatactt GTTTTTGTACTCTCAAGATTTAAGTAACTGTACAACctagaagctcaagcggtaaaagttgatggcg GTTTTTGTACTCTCAAGATTTAAGTAACTGTACAACctttgagggcaagccctcgccgttccattt GTTTTTGTACTCTCAAGATTTAAGTAACTGTACAACaactaccaagcaaatcagcaatcaataagt GTTTTTGTACTCTCAAGATTTAAGTAACTGTACAACctataagtgacaatcagcgtagggaatacg GTTTTTGTACTCTCAAGATTTAAGTAACTGTACAACatcagtgcggtatatttaccctagacgcta GTTTTTGTACTCTCAAGATTTAAGTAACTGTACAACaacagttactattaatcacgattccaacgg GTTTTTGTACTCTCAAGATTTAAGTAACTGTACAGTttgattcaacataaaaagccggttcaattg aacttggctttt
```

The parental strain (DGCC3198) was exposed to the donor bacteriophage (D4241) as described in Example 1.

Using the methods described in Example 1, isolates were obtained and further analyzed. PCR reactions and DNA sequence determination were performed as described in Example 1, except that the reverse primer used for the PCR was CR122-R3, with the following sequence: 5'-gctctaagatttgaggtgaagg-3' (SEQ ID NO:46).

Multiple tagged strains were created from DGCC3198 using D4241 as a donor. These tagged strains are described in Table 5-1. All of these tagged strains differ from the parental strain by a single additional repeat-spacer unit at the leader end of the CRISPR1 locus. For the 3 new spacer sequences described in Table 5-1, a homology search with sequences available from public database displayed the best homology scores with sub-sequences of the S. thermophilus bacteriophage DT1 (GenBank Accession Number AF085222), confirming that the new spacer sequence originated from the bacteriophage.

TABLE 5-1

Description of Tagged Strains in CRISPR1 Locus from DGCC3198 Using D4241 as Donor Bacteriophages

| Tagged Strain | Parental Strain | Donor Phage | Inserted Donor DNA Sequence |
|---|---|---|---|
| DGCC3198$_{phi4241}$$^{+S64}$ | DGCC3198 | D4241 | ACCAAGTAGCATTTGAGCAAAGATAGATTG (SEQ ID NO: 47) |
| DGCC3198$_{phi4241}$$^{+S65}$ | DGCC3198 | D4241 | TAGATCTCATGAGTGGCGACAGTGAGCTT (SEQ ID NO: 48) |
| DGCC3198$_{phi4241}$$^{+S66}$ | DGCC3198 | D4241 | TACCATCTTGGGATAGGTACTGGTCATGCC (SEQ ID NO: 49) |

Example 6

Tagging of Streptococcus thermophilus DGCC3198 Using Bacteriophage D4241 by the Insertion of a Single Repeat-Spacer Unit Within CRISPR3

In this Example, S. thermophilus strain DGCC3198 was tagged by "natural" insertion within its CRISPR3 locus of an additional repeat-spacer unit with the spacer originating from bacteriophage D4241. DGCC3198 CRISPR3 locus contains 9 repeats (including the terminal repeat) and 8 spacers (GenBank Accession Number: CP000419). The sequence of the DGCC3198 CRISPR3 locus is:

```
                                                                    (SEQ ID NO: 50)
taaattggtaataagtatagatagtcttgagttatttcaagactatcttttagtatttagtagtttctgtatgaagttgaatgggataatcattttgttagag agtagattataaggatttgatagaggaggaattaagttgcttgacatatgattattaagaaataatctaatatggtgacagtcacatcttgtctaaaacgttg atatataaggatttttaaggtataataaatataaaaatggaattattttgaagctgaagtcatgctgagattaatagtgcgattacgaaatctggtagaaaag atatcctacgagGTTTTAGAGCTGTGTTGTTTCGAATGGTTCCAAAACggtgaaaaaggttcactgtacgagtacttaGTTTTAG AGCTGTGTTGTTTCGAATGGTTCCAAAACtcaatgagtggtatccaagacgaaaacttaGTTTTAGAGCTGTGT TGTTTCGAATGGTTCCAAAACccttgtcgtggctctccatacgcccatataGTTTTAGAGCTGTGTTGTTTCGAA TGGTTCCAAAACtgtttgggaaaccgcagtagccatgattaaGTTTTAGAGCTGTGTTGTTTCGAATGGTTCCA AAACacagagtacaatattgtcctcattggagacacGTTTTAGAGCTGTGTTGTTTCGAATGGTTCCAAAACctcat attcgttagttgcttttgtcataaaGTTTTAGAGCTGTGTTGTTTCGAATGGTTCCAAAACagaactttatcaagataaaac tactttaaaGTTTTAGAGCTGTGTTGTTTCGAATGGTTCCAAAACatagtattaatttcattgaaaaataattgtGTTTT AGAGCTGTGTTGTTTCGAATGGTTCCAAAACtttgttatcacaattttcggttgacatctcttagaactcatcttatcataagg agtctagtattgaaatgtgagaagggac
```

The parental strain (DGCC3198) was exposed to the donor bacteriophage (D4241) as described in Example 1. Using the methods described in Example 1, isolates were obtained and further analyzed. PCR reactions and DNA sequence determination were performed as described in Example 1, except that CR3lead-F1 (5'-ctgagattaatagtgcgattacg-3'; SEQ ID NO:51) and CR3trail-R2 (5'-gctggatattcgtataacatgtc-3'; SEQ ID NO:52) were used.

One tagged strain was created from DGCC3198 using D4241 as a donor. This tagged strain is described in Table 6-1. This tagged strain differs from the parental strain by a single additional repeat-spacer unit at the leader end of the CRISPR3 locus. For the new spacer sequence described in Table 6, a homology search with sequences available from public database displayed the best homology scores with sub-sequences of the S. thermophiles bacteriophage DT1 and Sfi19 (GenBank Accession Number AF085222 and AF115102), confirming that the new spacer sequence originated from the bacteriophage.

the strain. Therefore, a specific PCR amplification method is designed that is specific to the tagged strain. A strain devoid of this unique oligonucleotide sequence results in no PCR amplified DNA, whereas PCR using the tagged strain DNA results in the amplification of a DNA fragment of a defined length.

To set up the specific PCR detection method, 2 primers are designed. One of the primers is the forward primer and is unspecific to the tagged strain but specific to a CRISPR locus; it is designated "CRISPR primer." In S. thermophilus, and depending on the tagged strain, the "CRISPR primer" is identical to a sequence within the CRISPR1 locus ("CRISPR1 primer") or within the CRISPR3 locus ("CRISPR3 primer") or within the CRISPR2 locus ("CRISPR2 primer"). The CRISPR primers are chosen among sequences that are conserved among strains of the species of interest. For S. thermophilus, the following primers are recommended: CRISPR1 primer, 5'-tgctgagacaac-ctagtctctc-3' (yc70, Bolotin et al., [2005], supra [SEQ ID

TABLE 6-1

Description of Tagged Strain in CRISPR3 Locus
From DGCC3198 Using D4241 as Donor Bacteriophages

| Tagged Strain | Parental Strain | Donor Phage | Inserted Donor DNA Sequence |
|---|---|---|---|
| DGCC3198$_{phi4241}^{+S67}$ | DGCC3198 | D4241 | 5'-tgcaatttccattagttcttgacgcccttt-3' (SEQ ID NO: 53) |

Example 7

PCR Method for Specific Detection of Tagged Strains

Figure 4:
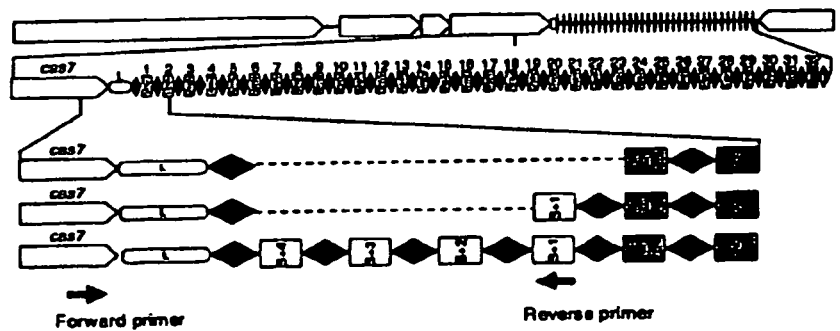
FIG. 4 provides a schematic representation of the CRISPR1 locus of *S. thermophilus* DCGG7710 and positioning of detection-PCR primers. The same symbols are used as in FIG. 3. The positions of the forward primer and reverse primer are indicated. Also, as indicated in the description of FIG. 3 above, the new numbering system of the cas genes is used. Previously, the cas genes were numbered cas1, cas2, cas3, and cas4. Now, the cas genes are numbered cas5, cas1, cas6, and cas7. Thus, to correlate the designations in FIGS. 1 and 2, with those in FIGS. 3 and 4, cas1 in FIGS. 1 and 2 is referred to as cas5 in FIGS. 3 and 4; cas2 in FIGS. 1 and 2 is cas1 in FIGS. 3 and 4; cas3 in FIGS. 1 and 2 is cas6 in FIGS. 3 and 4; and cas4 in FIGS. 1 and 2 is cas7 in FIGS. 3 and 4.

In this Example, PCR methods for specific detection of tagged strains are described. When a strain is naturally tagged by the addition of one or more unique oligonucleotide sequence(s) made of the added spacers in one or more of the CRISPR1 loci, it is necessary to be able to detect the tagged strains. The methods are based on the presence of sequences specific to the tagged strains that are inserted within a precisely identified region of the chromosome of NO:15]); CRISPR3 primer, 5'-ctgagattaatagtgcgattacg-3' (CR3lead-F1; SEQ ID NO:51). The second primer is the reverse primer and is specific to the tagged strain; it is designated "TAG primer". The TAG primers are complementary to one of the spacers of the added repeat-spacer units in the tagged strains. Preferably, the TAG primer is complementary to the spacer of the added repeat-spacer unit that is the more distal from the leader sequence of the CRISPR locus. FIG. 4 illustrates the location of the CRISPR primer and the TAG primer.

Table 7-1 provides examples of TAG primers for the detection of tagged strains listed in Example 1 to 6.

TABLE 7-1

Primers Used for the Detection of Tagged Strains Described in Example 1 to 6.

| Tagged Strain | CRISPR Primer | TAG Primer |
|---|---|---|
| DGCC7710$_{phi2972}$$^{+S40}$ | 5'-tgctgagacaacctagtctctc-3' (SEQ ID NO: 15) | 5'-aagagtagctccctcaatatgc-3' (SEQ ID NO: 54) |
| DGCC7710$_{phi2972}$$^{+S41}$ | 5'-tgctgagacaacctagtctctc-3' (SEQ ID NO: 15) | 5'-ttactacccactattcctagtg-3' (SEQ ID NO: 55) |
| DGCC7710$_{phi2972}$$^{+S43}$ | 5'-tgctgagacaacctagtctctc-3' (SEQ ID NO: 15) | 5'-atagaggccaactaaccgttat-3' (SEQ ID NO: 56) |
| DGCC7710$_{phi2972}$$^{+S44}$ | 5'-tgctgagacaacctagtctctc-3' (SEQ ID NO: 15) | 5'-tatcaattgcggaaatgtggct-3' (SEQ ID NO: 57) |
| DGCC7710$_{phi2972}$$^{+S45}$ | 5'-tgctgagacaacctagtctctc-3' (SEQ ID NO: 15) | 5'-cactgctgcttcaataaacatt-3' (SEQ ID NO: 58) |
| DGCC7710$_{phi2972}$$^{+S46}$ | 5'-tgctgagacaacctagtctctc-3' (SEQ ID NO: 15) | 5'-agaacaagtttctgaacaaaaa-3' (SEQ ID NO: 59) |
| DGCC7710$_{phi858}$$^{+S42}$ | 5'-tgctgagacaacctagtctctc-3' (SEQ ID NO: 15) | 5'-aaccacttaatactttggctga-3' (SEQ ID NO: 60) |
| DGCC7710$_{phi2972}$$^{+S46+S47}$ | 5'-tgctgagacaacctagtctctc-3' (SEQ ID NO: 15) | 5'-agaacaagtttctgaacaaaaa-3' (SEQ ID NO: 61) |
| DGCC7710$_{phi2972}$$^{+S48+S49}$ | 5'-tgctgagacaacctagtctctc-3' (SEQ ID NO: 15) | 5'-gctactgcatcgttaaagactt-3' (SEQ ID NO: 62) |
| DGCC7710$_{phi2972}$$^{+S50+S51}$ | 5'-tgctgagacaacctagtctctc-3' (SEQ ID NO: 15) | 5'-gagttctatttctcgaattatt-3' (SEQ ID NO: 63) |
| DGCC7710$_{phi2972}$$^{+S52+S4}$ | 5'-tgctgagacaacctagtctctc-3' (SEQ ID NO: 15) | 5'-tggctggagccctcgtacatta-3' (SEQ ID NO: 64) |
| DGCC7710$_{phi2972}$$^{+S53+S54}$ | 5'-tgctgagacaacctagtctctc-3' (SEQ ID NO: 15) | 5'-aatgatacttggacccgaaacc-3' (SEQ ID NO: 65) |
| DGCC7710$_{phi2972}$$^{+S61+S62}$ | 5'-tgctgagacaacctagtctctc-3' (SEQ ID NO: 15) | 5'-tcaaacgtaagacgaatatcgc-3' (SEQ ID NO: 66) |
| DGCC7710$_{phi2972}$$^{+S55+S63+S41}$ | 5'-tgctgagacaacctagtctctc-3' (SEQ ID NO: 15) | 5'-aagagtagctccctcaatatgc-3' (SEQ ID NO: 54) |
| DGCC7710$_{phi2972}$$^{+S6}$ | 5'-tgctgagacaacctagtctctc-3' (SEQ ID NO: 15) | 5'cacctcggaacctaatccaatt-3' (SEQ ID NO: 67) |
| DGCC7710$_{phi2972}$$^{+S6}$$_{phi4724}$$^{+S20}$ | 5'-tgctgagacaacctagtctctc-3' (SEQ ID NO: 15) | 5'-cacctcggaacctaatccaatt-3' (SEQ ID NO: 67) |
| DGCC7710$_{phi2972}$$^{+S6}$$_{phi4724}$$^{+S20}$$_{phi4733}$$^{+S29}$ | 5'-tgctgagacaacctagtctctc-3' (SEQ ID NO: 15) | 5'-cacctcggaacctaatccaatt-3' (SEQ ID NO: 67) |
| DGCC3198$_{phi4241}$$^{+S64}$ | 5'-tgctgagacaacctagtctctc-3' (SEQ ID NO: 15) | 5'-caatctatctttgctcaaatgc-3' (SEQ ID NO: 67) |
| DGCC3198$_{phi4241}$$^{+S65}$ | 5'-tgctgagacaacctagtctctc-3' (SEQ ID NO: 15) | 5'-aagctcactgtcgccactctag-3' (SEQ ID NO: 68) |
| DGCC3198$_{phi4241}$$^{+S66}$ | 5'-tgctgagacaacctagtctctc-3' (SEQ ID NO: 15) | 5'-ggcatgccagtacctatcccaa-3' (SEQ ID NO: 69) |
| DGCC3198$_{phi4241}$$^{+S67}$ | 5'-ctgagattaatagtgcgattacg-3' (SEQ ID NO: 51) | 5'-tcaagaactaatggaaattgcag-3' (SEQ ID NO: 70) |

In these experiments, the sample containing the strain to be detected was treated using any suitable method known in the art in order to sort the bacteria from the rest of the sample. As an example in case of yogurt or fresh dairy samples containing *S. thermophilus*, the sample was treated as described by Lick et al., (Lick et al., Milchwissenschaft 50:183-186 [1996]).

Depending on the amount of bacteria contained within the resulting material, *S. thermophilus* cells were amplified through cultivation in M17-glucose medium for 18 hours at 42° C. The DNA was then extracted from the bacteria and submitted to the specific PCR. The PCR primers (CRISPR primer and TAG primer) were chosen appropriately as described in Table 7-1. The PCR reaction mix (final volume of 25 µL) contained: Mg-free buffer 1× (Promega), MgCl$_2$ 2.5 mM, each of the four dNTP 2 mM, DNA 10 to 100 ng, each primer 0.2 µM, Taq polymerase 1.25 U (Promega). PCR cycling conditions were: pre-denaturation at 98° C. for 5 min, followed by 33 cycles alternating denaturation at 94° C. for 30 s, hybridization at 56° C. for 30 s, and elongation at 72° C. for 1 min; followed by a final elongation step at 72° C. for 4 min. In a control PCR, the extracted DNA was submitted to second PCR targeting 16S RNA genes using the following universal primers: BSF8-20, 5'-agagtttgatcctg-gctcag-3' (SEQ ID NO:71) and BSR1541-20, 5'-aaggaggt-gatccagccgca-3' (SEQ ID NO:72; See, Wilmotte et al., FEBS Lett., 317:96-100 [1993]).

The PCR reaction mix (final volume of 25 µL) contained: Mg-free buffer 1× (Promega), MgCl$_2$ 2.5 mM, each of the four dNTP 2 mM, DNA 10 to 100 ng, each primer 0.2 µM, Taq polymerase 1.25 U (Promega). PCR cycling conditions were as follows: pre-denaturation at 95° C. during 7 min, followed by 35 cycles of alternating denaturation at 95° C. during 1 min, hybridisation at 58° C. during 1 min 30s, and elongation at 72° C. for 2 mM 30 s; followed by a final elongation step at 72° C. for 5 min. The PCR amplification products were then analyzed using agarose (1%, w/v) gel electrophoresis and the size of the amplified DNA fragments was recorded. For each specific PCR, controls were made using DNA extracted from the parental strain (DGCC7710 or DGCC3198 depending on the tagged strain) and from one of the tagged strain (DGCC$_{phi2972}^{S6}$).

The results were presented in Table 7-2. Each of the PCR reactions was specific to the tested tagged strain, since PCR products of appropriate size were always obtained in control PCRs and specific PCRs only resulted in amplified DNA fragment when specific tagged strain DNA was used.

more of CRISPR loci and the partial sequence determination. This method finds use in various embodiments, as while the method described in Example 7 is useful for the detection of a tagged strain, it may not be sufficient for its formal identification. In addition in some cases, the nature of the tagged strain contained within the sample is not known. Thus, the specific PCR method cannot be used for its detection. Eventually, the tagged strain can be detected and identified through the analysis of the modified CRISPR locus.

*S. thermophilus* cells contained within a sample were extracted from the sample using suitable method known in the art and were plated at appropriate dilutions on agar M17-glucose agar then were incubated for 24 hours at 42° C. in order to obtained isolated colonies. One or more isolated colonies were then picked and grown in liquid M17-glucose medium for 18 hours at 42° C. From each culture, cells were harvested and their DNA extracted. For each isolate, the region of the chromosome corresponding to the CRISPR1 locus was amplified by PCR using the following primers: forward primer yc70 (5'-tgctgagacaac-ctagtctctc-3' [SEQ ID NO:15], Bolotin et al., [2005]; supra); and reverse primer SPIDR-dws (5'-taaacagagcctccctatcc-3' [SEQ ID NO:73]). The PCR reaction mix (final volume of 25 µL) contained: Mg-free buffer 1× (Promega), MgCl$_2$ 2.5 mM, each of the four dNTP 2 mM, DNA 10 to 100 ng, each primer 0.2 µM, Tag polymerase 1.25 U (Promega). PCR cycling conditions were as follows: pre-denaturation at 98° C. for 5 min, followed by 33 cycles alternating denaturation

TABLE 7-2

Size of the PCR Products Obtained Through Specific PCR and Control PCR on Tagged Strain DNA, Parental Strain DNA and DGCC$_{phi2972}^{S6}$ DNA

| Specific PCR$^c$ | Specific Tagged Strain DNA | | DGCC$_{phi2972}^{S6}$ DNA | | Parental Strain DNA | |
|---|---|---|---|---|---|---|
| | Specific PCR$^a$ | Control PCR$^a$ | Specific PCR$^a$ | Control PCR$^a$ | Specific PCR$^a$ | Control PCR$^a$ |
| DGCC7710$_{phi2972}^{+S40}$ | 240 | 1530 | 0 | 1530 | 0$^b$ | 1530 |
| DGCC7710$_{phi2972}^{+S41}$ | 240 | 1530 | 0 | 1530 | 0 | 1530 |
| DGCC7710$_{phi2972}^{+S43}$ | 240 | 1530 | 0 | 1530 | 0 | 1530 |
| DGCC7710$_{phi2972}^{+S44}$ | 240 | 1530 | 0 | 1530 | 0 | 1530 |
| DGCC7710$_{phi2972}^{+S45}$ | 240 | 1530 | 0 | 1530 | 0 | 1530 |
| DGCC7710$_{phi2972}^{+S46}$ | 240 | 1530 | 0 | 1530 | 0 | 1530 |
| DGCC7710$_{phi858}^{+S42}$ | 240 | 1530 | 0 | 1530 | 0 | 1530 |
| DGCC7710$_{phi2972}^{+S46+S47}$ | 310 | 1530 | 0 | 1530 | 0 | 1530 |
| DGCC7710$_{phi2972}^{+S48+S49}$ | 310 | 1530 | 0 | 1530 | 0 | 1530 |
| DGCC7710$_{phi2972}^{+S50+S51}$ | 310 | 1530 | 0 | 1530 | 0 | 1530 |
| DGCC7710$_{phi2972}^{+S52+S4}$ | 310 | 1530 | 0 | 1530 | 0 | 1530 |
| DGCC7710$_{phi2972}^{+S53+S54}$ | 310 | 1530 | 0 | 1530 | 0 | 1530 |
| DGCC7710$_{phi2972}^{+S61+S62}$ | 310 | 1530 | 0 | 1530 | 0 | 1530 |
| DGCC7710$_{phi2972}^{+S55+S63+S41}$ | 370 | 1530 | 0 | 1530 | 0 | 1530 |
| DGCC7710$_{phi2972}^{+S6}$ | 240 | 1530 | 240 | 1530 | 0 | 1530 |
| DGCC7710$_{phi2972}^{+S6}$ $_{phi4724}^{+S20}$ | 310 | 1530 | 0 | 1530 | 0 | 1530 |
| DGCC7710$_{phi2972}^{+S6}$ $_{phi4724}^{+S20}$ $_{phi4733}^{+S29}$ | 370 | 1530 | 0 | 1530 | 0 | 1530 |
| DGCC3198$_{phi4241}^{+S64}$ | 240 | 1530 | 0 | 1530 | 0 | 1530 |
| DGCC3198$_{phi4241}^{+S65}$ | 240 | 1530 | 0 | 1530 | 0 | 1530 |
| DGCC3198$_{phi4241}^{+S66}$ | 240 | 1530 | 0 | 1530 | 0 | 1530 |
| DGCC3198$_{phi4241}^{+S67}$ | 105 | 1530 | 0 | 1530 | 0 | 1530 |

$^a$approximate size of the amplified fragment in base pairs;
$^b$0 means no PCR fragment detected;
$^c$using the specific PCR primer as mentioned in Table 7-1.

Example 8

Method for the Identification of Tagged Strains

In this Example, a method is described for detecting the presence of tagged strains in a sample and to identify their nature. This is done through the PCR amplification of one or at 94° C. for 30 s, hybridization at 56° C. for 30 s, and elongation at 72° C. for 1 min; followed by a final elongation step at 72° C. for 4 min. In some cases, the region corresponding to the CRISPR3 locus was amplified using the following primers: CR3lead-F1, 5'-ctgagattaatagtgcgattacg-3' (SEQ ID NO:51) and CR3trail-R2, 5'-gctggatattcg-tataacatgtc-3' (SEQ ID NO:52). The nucleic acid sequence of each PCR fragment was then determined using the "forward primer" and classical sequencing methodology, as known in the art. Each sequence was then compared to sequences of CRISPR loci available in databases.

Figure 5:
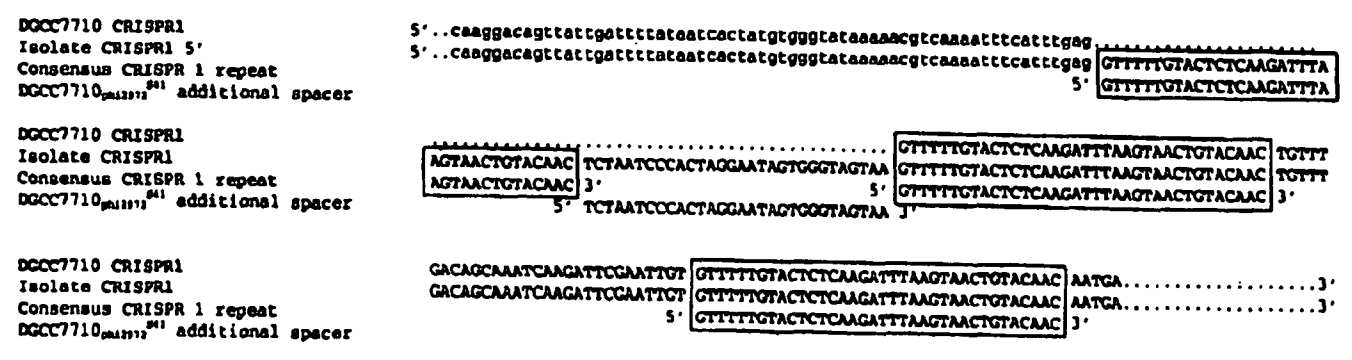

In one experiment, the CRISPR1 locus from an isolate obtained from a fermented milk product was submitted to PCR and the resulting amplicon was submitted to sequencing. The sequence was compared to that of sequences available in databases. FIG. 5 provides the results of the comparison. It appeared that the sequence was 100% identical to that of strain DGCC7710, with one additional sequence of 66 nucleotides. This 66 nucleotide sequence is made of 36 nucleotides in its 5'end that are identical to that of the repeats in the *S. thermophilus* CRISPR1 locus and the 30 remaining nucleotide sequence is identical to a subsequence of the bacteriophage D2972. Moreover, this 66 nucleotide-additional sequence was located immediately downstream of the leader sequence of CRISPR1. Consequently, the CRISPR1 locus of the isolate contains the CRISPR1 locus of DGCC7710 with one additional repeat-spacer unit as described in FIG. 3. In addition, the 30 remaining nucleotide sequence was also identical to the additional spacer sequence of the tagged strain $DGCC_{phi2972}^{S41}$. This conclusively indicated that the isolate obtained from the fermented milk product was the tagged strain $DGCC_{phi2972}^{S41}$.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A labelled bacterium comprising two or more additional repeat-spacer units integrated into a clustered regularly spaced short palindromic repeat (CRISPR) locus, as compared to the CRISPR locus of a parent bacterium from which the labelled bacterium is derived, wherein said spacer is a label, wherein said labelled bacterium is obtained or obtainable by a method comprising the steps of:
   (a) exposing the parent bacterium to a bacteriophage the parent bacterium is sensitive to;
   (b) selecting a bacteriophage insensitive mutant;
   (c) comparing a CRISPR locus or a portion thereof from the parent bacterium and the bacteriophage insensitive mutant; and
   (d) selecting a labelled bacterium comprising an additional repeat-spacer unit in the CRISPR locus that is not present in the CRISPR locus of the parent bacterium;
   wherein said method comprises exposing the parent bacterium to two or more bacteriophages the parent bacteria is sensitive to, either simultaneously or sequentially and wherein a labelled bacterium comprising two or more additional repeat-spacer units is selected; and wherein the labelled bacterium is insensitive to said two or more bacteriophages.

2. A cell culture comprising a labelled bacterium according to claim 1.

3. The cell culture according to claim 2, wherein said cell culture is a starter culture, a probiotic culture or a dietary supplement.

4. A food product or feed comprising the labelled bacterium according to claim 1.

5. A process for preparing a food product or feed comprising the step of adding the labelled bacterium according to claim 1 or the cell culture according to claim 2 or claim 3 to said food product or feed.

6. The labelled bacterium according to claim 1, wherein the parent bacterium is selected from the group of genera consisting of: *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Bifidobacterium, Brevibacterium, Propionibacterium, Lactococcus, Lactobacillus, Pediococcus, Leuconostoc* and *Oenococcus*.

7. The labelled bacterium according to claim 1 wherein the parent bacterium is *Streptococcus thennophilus*.

8. A dairy product comprising the labelled bacterium according to claim 1.

9. A starter culture comprising a labelled bacterium comprising two or more additional repeat-spacer units integrated into a clustered regularly spaced short palindromic repeat (CRISPR) locus, as compared to the CRISPR locus of a parent bacterium from which the labelled bacterium is derived, wherein said spacer is a label, wherein said labelled bacterium is obtained or obtainable by a method comprising the steps of:
   (a) exposing the parent bacterium to a bacteriophage the parent bacterium is sensitive to;
   (b) selecting a bacteriophage insensitive mutant;
   (c) comparing a CRISPR locus or a portion thereof from the parent bacterium and the bacteriophage insensitive mutant; and
   (d) selecting a labelled bacterium comprising an additional repeat-spacer unit in the CRISPR locus that is not present in the CRISPR locus of the parent bacterium;
   wherein said method comprises exposing the parent bacterium to two or more bacteriophages the parent bacterium is sensitive to, either simultaneously or sequentially and wherein a labelled bacterium comprising two or more additional repeat-spacer units is selected; and
   wherein the labelled bacterium is insensitive to said two or more bacteriophages.

10. The starter culture according to claim 9, wherein the starter culture is a defined mixed culture.

11. A probiotic culture comprising a labelled bacterium comprising two or more additional repeat-spacer units integrated into a clustered regularly spaced short palindromic repeat (CRISPR) locus, as compared to the CRISPR locus of a parent bacterium from which the labelled bacterium is derived, wherein said spacer is a label, wherein said labelled bacterium is obtained or obtainable by a method comprising the steps of:
   (a) exposing the parent bacterium to a bacteriophage the parent bacterium is sensitive to;
   (b) selecting a bacteriophage insensitive mutant;
   (c) comparing a CRISPR locus or a portion thereof from the parent bacterium and the bacteriophage insensitive mutant; and
   (d) selecting a labelled bacterium comprising an additional repeat-spacer unit in the CRISPR locus that is not present in the CRISPR locus of the parent bacterium;
   wherein said method comprises exposing the parent bacterium to two or more bacteriophages the parent bacterium is sensitive to, either simultaneously or sequentially and wherein a labelled bacterium comprising two or more additional repeat-spacer units is selected; and
   wherein the labelled bacterium is insensitive to said two or more bacteriophages.

12. A dietary supplement culture comprising a labelled bacterium comprising two or more additional repeat-spacer units integrated into a clustered regularly spaced short palindromic repeat (CRISPR) locus, as compared to the CRISPR locus of a parent bacterium from which the labelled bacterium is derived, wherein said spacer is a label, wherein said labelled bacterium is obtained or obtainable by a method comprising the steps of:
   (a) exposing the parent bacterium to a bacteriophage the parent bacterium is sensitive to;
   (b) selecting a bacteriophage insensitive mutant;
   (c) comparing a CRISPR locus or a portion thereof from the parent bacterium and the bacteriophage insensitive mutant; and
   (d) selecting a labelled bacterium comprising an additional repeat-spacer unit in the CRISPR locus that is not present in the CRISPR locus of the parent bacterium;
   wherein said method comprises exposing the parent bacterium to two or more bacteriophages the parent bacterium is sensitive to, either simultaneously or sequentially and wherein a labelled bacterium comprising two or more additional repeat-spacer units is selected; and
   wherein the labelled bacterium is insensitive to said two or more bacteriophage.

13. A frozen starter culture comprising a labelled bacterium comprising two or more additional repeat-spacer units integrated into a clustered regularly spaced short palindromic repeat (CRISPR) locus, as compared to the CRISPR locus of a parent bacterium from which the labelled bacterium is derived, wherein said spacer is a label, wherein said labelled bacterium is obtained or obtainable by a method comprising the steps of:
   (a) exposing the parent bacterium to a bacteriophage the parent bacterium is sensitive to;
   (b) selecting a bacteriophage insensitive mutant;
   (c) comparing a CRISPR locus or a portion thereof from the parent bacterium and the bacteriophage insensitive mutant; and
   (d) selecting a labelled bacterium comprising an additional repeat-spacer unit in the CRISPR locus that is not present in the CRISPR locus of the parent bacterium;
   wherein said method comprises exposing the parent bacterium to two or more bacteriophages the parent bacterium is sensitive to, either simultaneously or sequentially and wherein a labelled bacterium comprising two or more additional repeat-spacer units is selected; and
   wherein the labelled bacterium is insensitive to said two or more bacteriophages.

14. A dried starter culture comprising a labelled bacterium comprising two or more additional repeat-spacer units integrated into a clustered regularly spaced short palindromic repeat (CRISPR) locus, as compared to the CRISPR locus of a parent bacterium from which the labelled bacterium is derived, wherein said spacer is a label, wherein said labelled bacterium is obtained or obtainable by a method comprising the steps of:
   (a) exposing the parent bacterium to a bacteriophage the parent bacterium is sensitive to;
   (b) selecting a bacteriophage insensitive mutant;
   (c) comparing a CRISPR locus or a portion thereof from the parent bacterium and the bacteriophage insensitive mutant; and
   (d) selecting a labelled bacterium comprising an additional repeat-spacer unit in the CRISPR locus that is not present in the CRISPR locus of the parent bacterium;
   wherein said method comprises exposing the parent bacterium to two or more bacteriophages the parent bacterium is sensitive to, either simultaneously or sequentially and wherein a labelled bacterium comprising two or more additional repeat-spacer units is selected; and
   wherein the labelled bacterium is insensitive to said two or more bacteriophages.

15. A freeze dried starter culture comprising a labelled bacterium comprising two or more additional repeat-spacer units integrated into a clustered regularly spaced short palindromic repeat (CRISPR) locus, as compared to the CRISPR locus of a parent bacterium from which the labelled bacterium is derived, wherein said labelled bacterium is obtained or obtainable by a method comprising the steps of:
   (a) exposing the parent bacterium to a bacteriophage the parent bacterium is sensitive to;

(b) selecting a bacteriophage insensitive mutant;
(c) comparing a CRISPR locus or a portion thereof from the parent bacterium and the bacteriophage insensitive mutant; and
(d) selecting a labelled bacterium comprising an additional repeat-spacer unit in the CRISPR locus that is not present in the CRISPR locus of the parent bacterium;
wherein said method comprises exposing the parent bacterium to two or more bacteriophages the parent bacterium is sensitive to either simultaneously or sequentially and wherein a labelled bacterium comprising two or more additional repeat-spacer units is selected; and
wherein the labelled bacterium is insensitive to said two or more bacteriophages.

16. The labelled bacterium according to claim 1, wherein the two or more additional repeat-spacer units are integrated at the 5' end of the CRISPR locus.

17. The labelled bacterium according to claim 1, wherein the two or more additional repeat-spacer units are integrated at the 3' end of the CRISPR locus.

18. The labelled bacterium according to claim 1, wherein the two or more additional repeat-spacer units are integrated into one CRISPR locus.

19. The labelled bacterium according to claim 1, wherein the two or more additional repeat-spacer units are integrated into several CRISPR loci.

* * * * *

SEQUENCE LISTING

<160> NUMBER OF SEQ ID NOS: 75

<210> SEQ ID NO 1
<211> LENGTH: 2251
<212> TYPE: DNA
<213> ORGANISM: Streptococcus thermophilus

<400> SEQUENCE: 1

```
caaggacagt tattgatttt ataatcacta tgtgggtata aaaacgtcaa aatttcattt      60 gaggttttttg tactctcaag atttaagtaa ctgtacaact gtttgacagc aaatcaagat     120
tcgaattgtc tttttgtact ctcaagattt aagtaactgt acaacaatga cgaggagcta     180
ttggcacaac ttacagtttt tgtactctca agatttaagt aactgtacaa ccgatttgac     240
aatctgctga ccactgttat cgtttttgta ctctcaagat ttaagtaact gtacaacaca     300
cttggcaggc ttattactca acagcgagtt tttgtactct caagatttaa gtaactgtac     360
aacctgttcc ttgttctttt gttgtatctt ttcgtttttg tactctcaag atttaagtaa     420
ctgtacaact tcattcttcc gttttttgttt gcgaatcctg tttttgtact ctcaagattt     480
aagtaactgt acaacgctgg cgaggaaacg aacaaggcct caacagtttt tgtactctca     540
agatttaagt aactgtacaa ccatagagtg gaaaactaga aacagattca agtttttgta     600
ctctcaagat ttaagtaact gtacaacata atgccgttga attacacggc aaggtcagtt     660
tttgtactct caagatttaa gtaactgtac aacgagcgag ctcgaaataa tcttaattac     720
aaggtttttg tactctcaag atttaagtaa ctgtacaacg ttcgctagcg tcatgtggta     780
acgtatttag tttttgtact ctcaagattt aagtaactgt acaacggcgt cccaatcctg     840
```

```
attaatactt actcggtttt tgtactctca agatttaagt aactgtacaa caacacagca      900
agacaagagg atgatgctat ggttttgta ctctcaagat ttaagtaact gtacaaccga      960
cacaagaacg tatgcaagag ttcaaggttt ttgtactctc aagatttaag taactgtaca    1020
acacaattct tcatccggta actgctcaag tggttttgt actctcaaga tttaagtaac     1080
tgtacaacaa ttaagggcat agaaagggag acaacatggt ttttgtactc tcaagattta    1140
agtaactgta caaccgatat ttaaaatcat tttcataact tcatgttttt gtactctcaa    1200
gatttaagta actgtacaac gcagtatcag caagcaagct gttagttact gttttgtac     1260
tctcaagatt taagtaactg tacaacataa actatgaaat tttataattt ttaagagttt    1320
ttgtactctc aagatttaag taactgtaca acaataattt atggtatagc ttaatatcat    1380
tggttttgt actctcaaga tttaagtaac tgtacaactg catcgagcac gttcgagttt     1440
accgtttcgt ttttgtactc tcaagattta agtaactgta caactctata tcgaggtcaa    1500
ctaacaatta tgctgttttt gtactctcaa gatttaagta actgtacaac aatcgttcaa    1560
attctgtttt aggtacattt gttttgtac tctcaagatt taagtaactg tacaacaatc     1620
aatacgacaa gagttaaaat ggtcttgttt tgtactctc aagatttaag taactgtaca     1680
acgcttagct gtccaatcca cgaacgtgga tggttttgt actctcaaga tttaagtaac     1740
tgtacaacca accaacggta acagctactt tttacagtgt ttttgtactc tcaagattta    1800
agtaactgta caacataact gaaggatagg agcttgtaaa gtctgttttt gtactctcaa    1860
gatttaagta actgtacaac taatgctaca tctcaaagga tgatcccaga gtttttgtac    1920
tctcaagatt taagtaactg tacaacaagt agttgatgac ctctacaatg gtttatgttt    1980
ttgtactctc aagatttaag taactgtaca acacctagaa gcatttgagc gtatattgat    2040
tggttttgt actctcaaga tttaagtaac tgtacaacaa ttttgcccct tctttgcccc     2100
ttgactaggt ttttgtactc tcaagattta agtaactgta caacaccatt agcaatcatt    2160
tgtgcccatt gagtgttttt gtactctcaa gatttaagta actgtacagt ttgattcaac    2220
ataaaaagcc agttcaattg aacttggctt t                                    2251

<210> SEQ ID NO 2
<211> LENGTH: 2357
<212> TYPE: DNA
<213> ORGANISM: Streptococcus thermophilus

<400> SEQUENCE: 2
actatgtggg tataaaaacg tcaaaatttc atttgaggtt tttgtactct caagatttaa     60
gtaactgtac aaccaacaca ttcaacagat taatgaagaa tacgttttg tactctcaag     120
atttaagtaa ctgtacaact ccactcacgt acaaatagtg agtgtactcg ttttgtact    180
ctcaagattt aagtaactgt acaactgttt gacagcaaat caagattcga attgtgtttt    240
tgtactctca agatttaagt aactgtacaa caatgacgag gagctattgg cacaacttac    300
agttttgta ctctcaagat ttaagtaact gtacaaccga tttgacaatc tgctgaccac    360
tgttatcgtt tttgtactct caagatttaa gtaactgtac aacacacttg gcaggcttat     420
tactcaacag cgagttttg tactctcaag atttaagtaa ctgtacaacc tgttccttgt    480
tcttttgttg tatcttttcg ttttgtact ctcaagattt aagtaactgt acaacttcat    540
tcttccgttt ttgtttgcga atcctgtttt tgtactctca agatttaagt aactgtacaa    600
cgctggcgag gaaacgaaca aggcctcaac agttttgta ctctcaagat ttaagtaact    660
```

-continued

```
gtacaaccat agagtggaaa actagaaaca gattcaagtt tttgtactct caagatttaa    720
gtaactgtac aacataatgc cgttgaatta cacggcaagg tcagttttg tactctcaag    780
atttaagtaa ctgtacaacg agcgagctcg aaataatctt aattcaagg ttttttgtact   840
ctcaagattt aagtaactgt acaacgttcg ctagcgtcat gtggtaacgt atttagtttt   900
tgtactctca agatttaagt aactgtacaa cggcgtccca atcctgatta atacttactc   960
ggttttgta ctctcaagat ttaagtaact gtacaacaac acagcaagac aagaggatga   1020
tgctatggtt tttgtactct caagatttaa gtaactgtac aaccgacaca gaacgtatg   1080
caagagttca aggtttttgt actctcaaga tttaagtaac tgtacaacac aattcttcat   1140
ccggtaactg ctcaagtggt ttttgtactc tcaagattta agtaactgta caacaattaa   1200
gggcatagaa agggagacaa catggttttt gtactctcaa gatttaagta actgtacaac   1260
cgatatttaa aatcattttc ataacttcat gttttttgtac tctcaagatt taagtaactg   1320
tacaacgcag tatcagcaag caagctgtta gttactgttt ttgtactctc aagatttaag   1380
taactgtaca acataaacta tgaaatttta aattttttaa gagttttgt actctcaaga   1440
tttaagtaac tgtacaacaa taattatgg tatagcttaa tatcattggt ttttgtactc    1500
tcaagattta agtaactgta caactgcatc gagcacgttc gagtttaccg tttcgttttt   1560
gtactctcaa gatttaagta actgtacaac tctatatcga ggtcaactaa caattatgct   1620
gttttgtac tctcaagatt taagtaactg tacaacaatc gttcaaattc tgttttaggt   1680
acatttgttt ttgtactctc aagatttaag taactgtaca acaatcaata cgacaagagt   1740
taaaatggtc ttgttttgt actctcaaga tttaagtaac tgtacaacgc ttagctgtcc   1800
aatccacgaa cgtggatggt ttttgtactc tcaagattta agtaactgta caaccaacca   1860
acggtaacag ctactttta cagtgttttt gtactctcaa gatttaagta actgtacaac   1920
ataactgaag gataggagct tgtaaagtct gttttgtac tctcaagatt taagtaactg   1980
tacaactaat gctacatctc aaaggatgat cccagagttt ttgtactctc aagatttaag   2040
taactgtaca acaagtagtt gatgacctct acaatggttt atgttttgt actctcaaga   2100
tttaagtaac tgtacaacac ctagaagcat ttgagcgtat attgattggt ttttgtactc   2160
tcaagattta agtaactgta caacaattt gccccttctt tgccccttga ctaggttttt   2220
gtactctcaa gatttaagta actgtacaac accattagca atcatttgtg cccattgagt   2280
gttttgtac tctcaagatt taagtaactg tacagtttga ttcaacataa aaagccagtt   2340
caattgaact tggcttt                                                  2357
```

<210> SEQ ID NO 3
<211> LENGTH: 30
<212> TYPE: DNA
<213> ORGANISM: Streptococcus thermophilus

<400> SEQUENCE: 3

```
caacacattc aacagattaa tgaagaatac                                    30
```

<210> SEQ ID NO 4
<211> LENGTH: 30
<212> TYPE: DNA
<213> ORGANISM: Streptococcus thermophilus

<400> SEQUENCE: 4

```
tccactcacg tacaaatagt gagtgtactc                                    30
```

<210> SEQ ID NO 5
<211> LENGTH: 2317
<212> TYPE: DNA
<213> ORGANISM: Streptococcus thermophilus

<400> SEQUENCE: 5

| | | | | | |
|---|---|---|---|---|---|
| caaggacagt | tattgatttt | ataatcacta | tgtgggtata | aaaacgtcaa | aatttcattt | 60 |
| gaggttttg | tactctcaag | atttaagtaa | ctgtacaact | caacaattgc | aacatcttat | 120 |
| aacccacttg | tttttgtact | ctcaagattt | aagtaactgt | acaactgttt | gacagcaaat | 180 |
| caagattcga | attgtgtttt | tgtactctca | agatttaagt | aactgtacaa | caatgacgag | 240 |
| gagctattgg | cacaacttac | agtttttgta | ctctcaagat | ttaagtaact | gtacaaccga | 300 |
| tttgacaatc | tgctgaccac | tgttatcgtt | tttgtactct | caagatttaa | gtaactgtac | 360 |
| aacacacttg | gcaggcttat | tactcaacag | cgagttttg | tactctcaag | atttaagtaa | 420 |
| ctgtacaacc | tgttccttgt | tcttttgttg | tatcttttcg | tttttgtact | ctcaagattt | 480 |
| aagtaactgt | acaacttcat | tcttccgttt | tgtttgcga | atcctgtttt | tgtactctca | 540 |
| agatttaagt | aactgtacaa | cgctggcgag | gaaacgaaca | aggcctcaac | agttttgta | 600 |
| ctctcaagat | ttaagtaact | gtacaaccat | agagtggaaa | actagaaaca | gattcaagtt | 660 |
| tttgtactct | caagatttaa | gtaactgtac | aacataatgc | cgttgaatta | cacggcaagg | 720 |
| tcagttttg | tactctcaag | atttaagtaa | ctgtacaacg | agcgagctcg | aaataatctt | 780 |
| aattacaagg | tttttgtact | ctcaagattt | aagtaactgt | acaacgttcg | ctagcgtcat | 840 |
| gtggtaacgt | atttagtttt | tgtactctca | agatttaagt | aactgtacaa | cggcgtccca | 900 |
| atcctgatta | atacttactc | ggttttgta | ctctcaagat | ttaagtaact | gtacaacaac | 960 |
| acagcaagac | aagaggatga | tgctatggtt | tttgtactct | caagatttaa | gtaactgtac | 1020 |
| aaccgacaca | agaacgtatg | caagagttca | aggttttgt | actctcaaga | tttaagtaac | 1080 |
| tgtacaacac | aattcttcat | ccggtaactg | ctcaagtggt | tttgtactc | tcaagattta | 1140 |
| agtaactgta | caacaattaa | gggcatagaa | agggagacaa | catggttttt | gtactctcaa | 1200 |
| gatttaagta | actgtacaac | cgatatttaa | aatcattttc | ataacttcat | gttttgtac | 1260 |
| tctcaagatt | taagtaactg | tacaacgcag | tatcagcaag | caagctgtta | gttactgttt | 1320 |
| ttgtactctc | aagatttaag | taactgtaca | acataaacta | tgaaatttta | taatttttaa | 1380 |
| gagttttgt | actctcaaga | tttaagtaac | tgtacaacaa | taatttatgg | tatagcttaa | 1440 |
| tatcattggt | ttttgtactc | tcaagattta | agtaactgta | caactgcatc | gagcacgttc | 1500 |
| gagtttaccg | tttcgttttt | gtactctcaa | gatttaagta | actgtacaac | tctatatcga | 1560 |
| ggtcaactaa | caattatgct | gttttgtac | tctcaagatt | taagtaactg | tacaacaatc | 1620 |
| gttcaaattc | tgttttaggt | acatttgttt | ttgtactctc | aagatttaag | taactgtaca | 1680 |
| acaatcaata | cgacaagagt | taaatggtc | ttgttttgt | actctcaaga | tttaagtaac | 1740 |
| tgtacaacgc | ttagctgtcc | aatccacgaa | cgtggatggt | ttttgtactc | tcaagattta | 1800 |
| agtaactgta | caaccaacca | acggtaacag | ctacttttta | cagtgttttt | gtactctcaa | 1860 |
| gatttaagta | actgtacaac | ataactgaag | gataggagct | tgtaaagtct | gtttttgtac | 1920 |
| tctcaagatt | taagtaactg | tacaactaat | gctacatctc | aaaggatgat | cccagagttt | 1980 |
| ttgtactctc | aagatttaag | taactgtaca | acaagtagtt | gatgacctct | acaatggttt | 2040 |
| atgttttgt | actctcaaga | tttaagtaac | tgtacaacac | ctagaagcat | tgagcgtat | 2100 |
| attgattggt | ttttgtactc | tcaagattta | agtaactgta | caacaatttt | gccccttctt | 2160 |

```
tgccccttga ctaggttttt gtactctcaa gatttaagta actgtacaac accattagca    2220
atcatttgtg cccattgagt gttttttgtac tctcaagatt taagtaactg tacagtttga    2280
ttcaacataa aaagccagtt caattgaact tggcttt                               2317

<210> SEQ ID NO 6
<211> LENGTH: 63
<212> TYPE: DNA
<213> ORGANISM: Streptococcus thermophilus

<400> SEQUENCE: 6
caaggacagt tattgatttt ataatcacta tgtgggtata aaaacgtcaa aatttcattt    60
gag                                                                   63

<210> SEQ ID NO 7
<211> LENGTH: 36
<212> TYPE: DNA
<213> ORGANISM: Streptococcus thermophilus

<400> SEQUENCE: 7
gtttttgtac tctcaagatt taagtaactg tacagt                               36

<210> SEQ ID NO 8
<211> LENGTH: 41
<212> TYPE: DNA
<213> ORGANISM: Streptococcus thermophilus

<400> SEQUENCE: 8
ttgattcaac ataaaaagcc agttcaattg aacttggctt t                         41

<210> SEQ ID NO 9
<211> LENGTH: 30
<212> TYPE: DNA
<213> ORGANISM: Streptococcus thermophilus

<400> SEQUENCE: 9
tcaacaattg caacatctta taacccactt                                      30

<210> SEQ ID NO 10
<211> LENGTH: 2317
<212> TYPE: DNA
<213> ORGANISM: Streptococcus thermophilus

<400> SEQUENCE: 10
caaggacagt tattgatttt ataatcacta tgtgggtata aaaacgtcaa aatttcattt    60 gaggttttg tactctcaag atttaagtaa ctgtacaact tacgtttgaa agaatatca      120 aatcaatgag ttttttgtact ctcaagattt aagtaactgt acaactgttt gacagcaaat   180
caagattcga attgtgtttt tgtactctca agatttaagt aactgtacaa caatgacgag   240
gagctattgg cacaacttac agttttttgta ctctcaagat ttaagtaact gtacaaccga   300
tttgacaatc tgctgaccac tgttatcgtt tttgtactct caagatttaa gtaactgtac   360
aacacacttg gcaggcttat tactcaacag cgagttttttg tactctcaag atttaagtaa   420
ctgtacaacc tgttccttgt tcttttgttg tatcttttcg tttttgtact ctcaagattt   480
aagtaactgt acaacttcat tcttccgttt tgtttgcga atcctgtttt tgtactctca   540
agatttaagt aactgtacaa cgctggcgag gaaacgaaca aggcctcaac agttttttgta   600 ctctcaagat ttaagtaact gtacaaccat agagtggaaa actagaaaca gattcaagtt   660
tttgtactct caagatttaa gtaactgtac aacataatgc cgttgaatta cacggcaagg   720
```

```
tcagttttig  tactctcaag  atttaagtaa  ctgtacaacg  agcgagctcg  aaataatctt      780
aattacaagg  tttttgtact  ctcaagattt  aagtaactgt  acaacgttcg  ctagcgtcat      840
gtggtaacgt  atttagtttt  tgtactctca  agatttaagt  aactgtacaa  cggcgtccca      900
atcctgatta  atacttactc  ggttttigta  ctctcaagat  ttaagtaact  gtacaacaac      960
acagcaagac  aagaggatga  tgctatggtt  tttgtactct  caagatttaa  gtaactgtac     1020
aaccgacaca  agaacgtatg  caagagttca  aggtttttgt  actctcaaga  tttaagtaac     1080
tgtacaacac  aattcttcat  ccggtaactg  ctcaagtggt  ttttgtactc  tcaagattta     1140
agtaactgta  caacaattaa  gggcatagaa  agggagacaa  catggttttt  gtactctcaa     1200
gatttaagta  actgtacaac  cgatatttaa  aatcattttc  ataacttcat  gttttigtac     1260 tctcaagatt  taagtaactg  tacaacgcag  atcagcaag  caagctgtta  gttactgttt     1320
ttgtactctc  aagatttaag  taactgtaca  acataaacta  tgaaatttta  aattttttaa     1380 gagttttigt  actctcaaga  tttaagtaac  tgtacaacaa  taatttatgg  tatagcttaa     1440
tatcattggt  ttttgtactc  tcaagattta  agtaactgta  caactgcatc  gagcacgttc     1500
gagtttaccg  tttcgttttt  gtactctcaa  gatttaagta  actgtacaac  tctatatcga     1560
ggtcaactaa  caattatgct  gttittgtac  tctcaagatt  taagtaactg  tacaacaatc     1620
gttcaaattc  tgttttaggt  acatttgttt  ttgtactctc  aagatttaag  taactgtaca     1680
acaatcaata  cgacaagagt  aaaatggtc  ttgttttigt  actctcaaga  tttaagtaac     1740
tgtacaacgc  ttagctgtcc  aatccacgaa  cgtggatggt  ttttgtactc  tcaagattta     1800
agtaactgta  caaccaacca  acggtaacag  ctactttta  cagtgttttt  gtactctcaa     1860
gatttaagta  actgtacaac  ataactgaag  ataggagct  tgtaaagtct  gttttigtac     1920 tctcaagatt  taagtaactg  tacaactaat  gctacatctc  aaaggatgat  cccagagttt     1980
ttgtactctc  aagatttaag  taactgtaca  acaagtagtt  gatgacctct  acaatggttt     2040
atgtttttgt  actctcaaga  tttaagtaac  tgtacaacac  ctagaagcat  ttgagcgtat     2100
attgattggt  ttttgtactc  tcaagattta  agtaactgta  caacaatttt  gcccctict     2160 tgccccttga  ctaggttttt  gtactctcaa  gatttaagta  actgtacaac  accattagca     2220
atcatttgtg  cccattgagt  gttttigtac  tctcaagatt  taagtaactg  tacagtttga     2280
ttcaacataa  aaagccagtt  caattgaact  tggcttt                                2317

<210> SEQ ID NO 11
<211> LENGTH: 30
<212> TYPE: DNA
<213> ORGANISM: Streptococcus thermophilus

<400> SEQUENCE: 11
ttacgtttga  aaagaatatc  aaatcaatga                                           30

<210> SEQ ID NO 12
<211> LENGTH: 63
<212> TYPE: DNA
<213> ORGANISM: Streptococcus thermophilus

<400> SEQUENCE: 12
caaggacagt  tattgatttt  ataatcacta  tgtgggtata  aaaacgtcaa  aatttcattt       60
gag                                                                          63

<210> SEQ ID NO 13
```

```
<211> LENGTH: 41
<212> TYPE: DNA
<213> ORGANISM: Streptococcus thermophilus

<400> SEQUENCE: 13
ttgattcaac ataaaaagcc agttcaattg aacttggctt t                                41

<210> SEQ ID NO 14
<211> LENGTH: 36
<212> TYPE: DNA
<213> ORGANISM: Streptococcus thermophilus

<400> SEQUENCE: 14
gtttttgtac tctcaagatt taagtaactg tacaac                                      36

<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15
tgctgagaca acctagtctc tc                                                     22

<210> SEQ ID NO 16
<211> LENGTH: 23
<212> TYPE: DNA
<213> ORGANISM: Artificial
<220> FEATURE:
<223> OTHER INFORMATION: primer

<400> SEQUENCE: 16
acaaaaacgg aagaatgaag ttg                                                    23

<210> SEQ ID NO 17
<211> LENGTH: 30
<212> TYPE: DNA
<213> ORGANISM: Streptococcus phage D2972

<400> SEQUENCE: 17
tctggaaagc atattgaggg agctactctt                                             30

<210> SEQ ID NO 18
<211> LENGTH: 30
<212> TYPE: DNA
<213> ORGANISM: Streptococcus phage D2972

<400> SEQUENCE: 18
tctaatccca ctaggaatag tgggtagtaa                                             30

<210> SEQ ID NO 19
<211> LENGTH: 29
<212> TYPE: DNA
<213> ORGANISM: Streptococcus phage D2972

<400> SEQUENCE: 19
ttataacata acggttagtt ggcctctat                                              29

<210> SEQ ID NO 20
<211> LENGTH: 30
<212> TYPE: DNA
<213> ORGANISM: Streptococcus phage D2972

<400> SEQUENCE: 20
```
aaggagctag ccacatttcc gcaattgata                                30

<210> SEQ ID NO 21
<211> LENGTH: 30
<212> TYPE: DNA
<213> ORGANISM: Streptococcus phage D2972

<400> SEQUENCE: 21
cagcttgaaa tgtttattga agcagcagtg                                30

<210> SEQ ID NO 22
<211> LENGTH: 30
<212> TYPE: DNA
<213> ORGANISM: Streptococcus phage D2972

<400> SEQUENCE: 22
aaatcagttt tttgttcaga aacttgttct                                30

<210> SEQ ID NO 23
<211> LENGTH: 30
<212> TYPE: DNA
<213> ORGANISM: Streptococcus phage D858

<400> SEQUENCE: 23
tcgataaatc agccaaagta ttaagtggtt                                30

<210> SEQ ID NO 24
<211> LENGTH: 30
<212> TYPE: DNA
<213> ORGANISM: Streptococcus phage D2972

<400> SEQUENCE: 24
aaatcagttt tttgttcaga aacttgttct                                30

<210> SEQ ID NO 25
<211> LENGTH: 29
<212> TYPE: DNA
<213> ORGANISM: Streptococcus phage D2972

<400> SEQUENCE: 25
ttgtctatta cgacaacatg gaagatgat                                 29

<210> SEQ ID NO 26
<211> LENGTH: 30
<212> TYPE: DNA
<213> ORGANISM: Streptococcus phage D2972

<400> SEQUENCE: 26
ttttgagaaa gtctttaacg atgcagtagc                                30

<210> SEQ ID NO 27
<211> LENGTH: 30
<212> TYPE: DNA
<213> ORGANISM: Streptococcus phage D2972

<400> SEQUENCE: 27
taatagttta ccaaatcatc tttattccaa                                30

<210> SEQ ID NO 28
<211> LENGTH: 30
<212> TYPE: DNA
<213> ORGANISM: Streptococcus phage D2972

<400> SEQUENCE: 28
gaagttgaaa taattcgaga aatagaactc                                    30

<210> SEQ ID NO 29
<211> LENGTH: 30
<212> TYPE: DNA
<213> ORGANISM: Streptococcus phage D2972

<400> SEQUENCE: 29
tggaaaccaa gaaatgcaat agaatggaag                                    30

<210> SEQ ID NO 30
<211> LENGTH: 30
<212> TYPE: DNA
<213> ORGANISM: Streptococcus phage D2972

<400> SEQUENCE: 30
ctgattgtta atgtacgagg gctccagcca                                    30

<210> SEQ ID NO 31
<211> LENGTH: 30
<212> TYPE: DNA
<213> ORGANISM: Streptococcus phage D2972

<400> SEQUENCE: 31
ctcagtcgtt actggtgaac cagtttcaat                                    30

<210> SEQ ID NO 32
<211> LENGTH: 30
<212> TYPE: DNA
<213> ORGANISM: Streptococcus phage D2972

<400> SEQUENCE: 32
tgtttcaagg tttcgggtcc aagtatcatt                                    30

<210> SEQ ID NO 33
<211> LENGTH: 30
<212> TYPE: DNA
<213> ORGANISM: Streptococcus phage D2972

<400> SEQUENCE: 33
ttttccgtct tctttttag caaagatacg                                     30

<210> SEQ ID NO 34
<211> LENGTH: 30
<212> TYPE: DNA
<213> ORGANISM: Streptococcus phage D2972

<400> SEQUENCE: 34
gattcgtggc gatattcgtc ttacgtttga                                    30

<210> SEQ ID NO 35
<211> LENGTH: 29
<212> TYPE: DNA
<213> ORGANISM: Streptococcus phage D2972

<400> SEQUENCE: 35
acatatcgac gtatcgtgat tatcccatt                                     29

<210> SEQ ID NO 36
<211> LENGTH: 29
<212> TYPE: DNA
<213> ORGANISM: Streptococcus phage D2972

<400> SEQUENCE: 36
ctggaaagca tattgaggga gctactctt                              29

<210> SEQ ID NO 37
<211> LENGTH: 30
<212> TYPE: DNA
<213> ORGANISM: Streptococcus phage D2972

<400> SEQUENCE: 37
gtatatcgaa gaacgactga aagagcttga                             30

<210> SEQ ID NO 38
<211> LENGTH: 30
<212> TYPE: DNA
<213> ORGANISM: Streptococcus phage D2972

<400> SEQUENCE: 38
tctaatccca ctaggaatag tgggtagtaa                             30

<210> SEQ ID NO 39
<211> LENGTH: 30
<212> TYPE: DNA
<213> ORGANISM: Streptococcus phage D2972

<400> SEQUENCE: 39
gcccttctaa ttggattacc ttccgaggtg                             30

<210> SEQ ID NO 40
<211> LENGTH: 30
<212> TYPE: DNA
<213> ORGANISM: Artificial
<220> FEATURE:
<223> OTHER INFORMATION: synthetic phage

<400> SEQUENCE: 40
gcccttctaa ttggattacc ttccgaggtg                             30

<210> SEQ ID NO 41
<211> LENGTH: 30
<212> TYPE: DNA
<213> ORGANISM: Artificial
<220> FEATURE:
<223> OTHER INFORMATION: synthetic phage

<400> SEQUENCE: 41
ttatatcgaa gaacgactga aagagcttga                             30

<210> SEQ ID NO 42
<211> LENGTH: 30
<212> TYPE: DNA
<213> ORGANISM: Artificial
<220> FEATURE:
<223> OTHER INFORMATION: synthetic phage

<400> SEQUENCE: 42
gcccttctaa ttggattacc ttccgaggtg                             30

<210> SEQ ID NO 43
<211> LENGTH: 30
<212> TYPE: DNA
<213> ORGANISM: Artificial
<220> FEATURE:
<223> OTHER INFORMATION: synthetic phage

```
<400> SEQUENCE: 43
ttatatcgaa gaacgactga aagagcttga                                      30

<210> SEQ ID NO 44
<211> LENGTH: 29
<212> TYPE: DNA
<213> ORGANISM: Artificial
<220> FEATURE:
<223> OTHER INFORMATION: synthetic phage

<400> SEQUENCE: 44
attggcatga tttcaatttt aattgggat                                       29

<210> SEQ ID NO 45
<211> LENGTH: 1196
<212> TYPE: DNA
<213> ORGANISM: Streptococcus thermophilus

<400> SEQUENCE: 45
caagaacagt tattgatttt ataatcacta tgtgggtatg aaaatctcaa aaatcatttg     60 aggttttgt  actctcaaga tttaagtaac tgtacaacat gatgatgaag tatcgtcatc    120
tactaacgtt tttgtactct caagatttaa gtaactgtac aaccttcacc tcaaatctta    180
gagctggact aaagttttg  tactctcaag atttaagtaa ctgtacaaca tgtctgaaaa    240
ataaccgacc atcattactg tttttgtact ctcaagattt aagtaactgt acaacgaagc    300
tcatcatgtt aaggctaaaa cctatgtttt tgtactctca agatttaagt aactgtacaa    360
ctagtctaaa tagatttctt gcaccattgt agttttgta  ctctcaagat ttaagtaact    420
gtacaacatt cgtgaaaaaa tatcgtgaaa taggcaagtt tttgtactct caagatttaa    480
gtaactgtac aactctaggc tcatctaaag ataaatcagt agcgttttg  tactctcaag    540 atttaagtaa ctgtacaact aaaaacatgg ggcggcggta atagtgtaag gttttgtac    600 tctcaagatt taagtaactg tacaacacaa ccagcaaaga gagcgccgac aacattgttt    660
ttgtactctc aagatttaag taactgtaca actataacac aggtttagag gatgttatac    720 ttgttttgt  actctcaaga tttaagtaac tgtacaacct agaagctcaa gcggtaaaag    780
ttgatggcgg ttttgtact  ctcaagattt aagtaactgt acaacctttg agggcaagcc    840
ctcgccgttc catttgtttt tgtactctca agatttaagt aactgtacaa caactaccaa    900
gcaaatcagc aatcaataag tgttttgta  ctctcaagat ttaagtaact gtacaaccta    960
taagtgacaa tcagcgtagg gaatacggtt tttgtactct caagatttaa gtaactgtac   1020
aacatcagtg cggtatattt accctagacg ctagttttg  tactctcaag atttaagtaa   1080
ctgtacaaca acagttacta ttaatcacga ttccaacggg tttttgtact ctcaagattt   1140
aagtaactgt acagtttgat tcaacataaa aagccggttc aattgaactt ggcttt       1196

<210> SEQ ID NO 46
<211> LENGTH: 22
<212> TYPE: DNA
<213> ORGANISM: Artificial
<220> FEATURE:
<223> OTHER INFORMATION: primer

<400> SEQUENCE: 46
gctctaagat ttgaggtgaa gg                                              22

<210> SEQ ID NO 47
<211> LENGTH: 30
```

```
<212> TYPE: DNA
<213> ORGANISM: Streptococcus phage D4241

<400> SEQUENCE: 47
accaagtagc atttgagcaa agatagattg                                        30

<210> SEQ ID NO 48
<211> LENGTH: 29
<212> TYPE: DNA
<213> ORGANISM: Streptococcus phage D4241

<400> SEQUENCE: 48
tagatctcat gagtggcgac agtgagctt                                         29

<210> SEQ ID NO 49
<211> LENGTH: 30
<212> TYPE: DNA
<213> ORGANISM: Streptococcus phage D4241

<400> SEQUENCE: 49
taccatcttg ggataggtac tggtcatgcc                                        30

<210> SEQ ID NO 50
<211> LENGTH: 970
<212> TYPE: DNA
<213> ORGANISM: Streptococcus thermophilus

<400> SEQUENCE: 50
taaattggta ataagtatag atagtcttga gttatttcaa gactatcttt tagtattttag      60 tagtttctgt atgaagttga atgggataat cattttgtta gagagtagat tataaggatt     120
tgatagagga ggaattaagt tgcttgacat atgattatta agaaataatc taatatggtg     180
acagtcacat cttgtctaaa acgttgatat ataaggattt ttaaggtata ataaatataa     240
aaatggaatt attttgaagc tgaagtcatg ctgagattaa tagtgcgatt acgaaatctg     300
gtagaaaaga tatcctacga ggttttagag ctgtgttgtt tcgaatggtt ccaaaacggt     360
gaaaaaggtt cactgtacga gtacttagtt ttagagctgt gttgtttcga atggttccaa     420
aactcaatga gtggtatcca agacgaaaac ttagtttag agctgtgttg tttcgaatgg     480
ttccaaaacc cttgtcgtgg ctctccatac gcccatatag ttttagagct gtgttgtttc     540
gaatggttcc aaaactgttt gggaaaccgc agtagccatg attaagtttt agagctgtgt     600
tgtttcgaat ggttccaaaa cacagagtac aatattgtcc tcattggaga cacgttttag     660
agctgtgttg tttcgaatgg ttccaaaacc tcatattcgt tagttgcttt tgtcataaag     720
ttttagagct gtgttgtttc gaatggttcc aaaacagaac tttatcaaga taaaactact     780
ttaaagtttt agagctgtgt tgtttcgaat ggttccaaaa catagtatta atttcattga     840 aaataattg tgttttagag ctgtgttgtt tcgaatggtt ccaaaacttt gttatcaca      900 attttcggtt gacatctctt agaactcatc ttatcataaa ggagtctagt attgaaatgt     960
gagaagggac                                                             970

<210> SEQ ID NO 51
<211> LENGTH: 23
<212> TYPE: DNA
<213> ORGANISM: Artificial
<220> FEATURE:
<223> OTHER INFORMATION: primer

<400> SEQUENCE: 51
```
ctgagattaa tagtgcgatt acg                                               23

<210> SEQ ID NO 52
<211> LENGTH: 23
<212> TYPE: DNA
<213> ORGANISM: Artificial
<220> FEATURE:
<223> OTHER INFORMATION: primer

<400> SEQUENCE: 52
gctggatatt cgtataacat gtc                                               23

<210> SEQ ID NO 53
<211> LENGTH: 30
<212> TYPE: DNA
<213> ORGANISM: Streptococcus phage D4241

<400> SEQUENCE: 53
tgcaatttcc attagttctt gacgcccttt                                        30

<210> SEQ ID NO 54
<211> LENGTH: 22
<212> TYPE: DNA
<213> ORGANISM: Artificial
<220> FEATURE:
<223> OTHER INFORMATION: primer

<400> SEQUENCE: 54
aagagtagct ccctcaatat gc                                                22

<210> SEQ ID NO 55
<211> LENGTH: 22
<212> TYPE: DNA
<213> ORGANISM: Artificial
<220> FEATURE:
<223> OTHER INFORMATION: primer

<400> SEQUENCE: 55
ttactaccca ctattcctag tg                                                22

<210> SEQ ID NO 56
<211> LENGTH: 22
<212> TYPE: DNA
<213> ORGANISM: Artificial
<220> FEATURE:
<223> OTHER INFORMATION: primer

<400> SEQUENCE: 56
atagaggcca actaaccgtt at                                                22

<210> SEQ ID NO 57
<211> LENGTH: 22
<212> TYPE: DNA
<213> ORGANISM: Artificial
<220> FEATURE:
<223> OTHER INFORMATION: primer

<400> SEQUENCE: 57
tatcaattgc ggaaatgtgg ct                                                22

<210> SEQ ID NO 58
<211> LENGTH: 22
<212> TYPE: DNA
<213> ORGANISM: Artificial
<220> FEATURE:
<223> OTHER INFORMATION: primer

<400> SEQUENCE: 58
cactgctgct tcaataaaca tt          22

<210> SEQ ID NO 59
<211> LENGTH: 22
<212> TYPE: DNA
<213> ORGANISM: Artificial
<220> FEATURE:
<223> OTHER INFORMATION: primer

<400> SEQUENCE: 59
agaacaagtt tctgaacaaa aa          22

<210> SEQ ID NO 60
<211> LENGTH: 22
<212> TYPE: DNA
<213> ORGANISM: Artificial
<220> FEATURE:
<223> OTHER INFORMATION: primer

<400> SEQUENCE: 60
aaccacttaa tactttggct ga          22

<210> SEQ ID NO 61
<211> LENGTH: 22
<212> TYPE: DNA
<213> ORGANISM: Artificial
<220> FEATURE:
<223> OTHER INFORMATION: primer

<400> SEQUENCE: 61
agaacaagtt tctgaacaaa aa          22

<210> SEQ ID NO 62
<211> LENGTH: 22
<212> TYPE: DNA
<213> ORGANISM: Artificial
<220> FEATURE:
<223> OTHER INFORMATION: primer

<400> SEQUENCE: 62
gctactgcat cgttaaagac tt          22

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
gagttctatt tctcgaatta tt          22

<210> SEQ ID NO 64
<211> LENGTH: 22
<212> TYPE: DNA
<213> ORGANISM: Artificial
<220> FEATURE:
<223> OTHER INFORMATION: primer

<400> SEQUENCE: 64
tggctggagc cctcgtacat ta          22

<210> SEQ ID NO 65

```
<211> LENGTH: 22
<212> TYPE: DNA
<213> ORGANISM: Artificial
<220> FEATURE:
<223> OTHER INFORMATION: primer

<400> SEQUENCE: 65
aatgatactt ggacccgaaa cc                                              22

<210> SEQ ID NO 66
<211> LENGTH: 22
<212> TYPE: DNA
<213> ORGANISM: Artificial
<220> FEATURE:
<223> OTHER INFORMATION: primer

<400> SEQUENCE: 66
tcaaacgtaa gacgaatatc gc                                              22

<210> SEQ ID NO 67
<211> LENGTH: 22
<212> TYPE: DNA
<213> ORGANISM: Artificial
<220> FEATURE:
<223> OTHER INFORMATION: primer

<400> SEQUENCE: 67
cacctcggaa cctaatccaa tt                                              22

<210> SEQ ID NO 68
<211> LENGTH: 22
<212> TYPE: DNA
<213> ORGANISM: Artificial
<220> FEATURE:
<223> OTHER INFORMATION: primer

<400> SEQUENCE: 68
aagctcactg tcgccactct ag                                              22

<210> SEQ ID NO 69
<211> LENGTH: 22
<212> TYPE: DNA
<213> ORGANISM: Artificial
<220> FEATURE:
<223> OTHER INFORMATION: primer

<400> SEQUENCE: 69
ggcatgccag tacctatccc aa                                              22

<210> SEQ ID NO 70
<211> LENGTH: 23
<212> TYPE: DNA
<213> ORGANISM: Artificial
<220> FEATURE:
<223> OTHER INFORMATION: primer

<400> SEQUENCE: 70
tcaagaacta atggaaattg cag                                             23

<210> SEQ ID NO 71
<211> LENGTH: 20
<212> TYPE: DNA
<213> ORGANISM: Artificial
<220> FEATURE:
<223> OTHER INFORMATION: primer

<400> SEQUENCE: 71
```

```
agagtttgat cctggctcag                                               20

<210> SEQ ID NO 72
<211> LENGTH: 20
<212> TYPE: DNA
<213> ORGANISM: Artificial
<220> FEATURE:
<223> OTHER INFORMATION: primer

<400> SEQUENCE: 72
aaggaggtga tccagccgca                                               20

<210> SEQ ID NO 73
<211> LENGTH: 20
<212> TYPE: DNA
<213> ORGANISM: Artificial
<220> FEATURE:
<223> OTHER INFORMATION: primer

<400> SEQUENCE: 73
taaacagagc ctccctatcc                                               20

<210> SEQ ID NO 74
<211> LENGTH: 36
<212> TYPE: DNA
<213> ORGANISM: Streptococcus thermophilus

<400> SEQUENCE: 74
gtttttgtac tctcaagatt taagtaactg tacaac                             36

<210> SEQ ID NO 75
<211> LENGTH: 30
<212> TYPE: DNA
<213> ORGANISM: Artificial
<220> FEATURE:
<223> OTHER INFORMATION: synthetic Streptococcus thermophilus CRISPR1
      sequence with additional spacer

<400> SEQUENCE: 75
tctaatccca ctaggaatag tgggtagtaa                                    30
```